United States Patent
Fung et al.

(10) Patent No.: US 10,405,919 B2
(45) Date of Patent: Sep. 10, 2019

(54) METHODS AND DEVICES FOR TREATING ATRIAL FIBRILLATION

(71) Applicant: SentreHEART, Inc., Redwood City, CA (US)

(72) Inventors: Gregory W. Fung, Redwood Shores, CA (US); Russell A. Seiber, Redwood City, CA (US); Robert Strasser, Mountain View, CA (US); Arnold M. Escano, San Jose, CA (US); Ryan Douglas Helmuth, Saratoga, CA (US)

(73) Assignee: SentreHEART, Inc., Redwood City, CA (US)

( * ) Notice: Subject to any disclaimer, the term of this patent is extended or adjusted under 35 U.S.C. 154(b) by 730 days.

(21) Appl. No.: 14/799,419

(22) Filed: Jul. 14, 2015

(65) Prior Publication Data
US 2016/0008061 A1    Jan. 14, 2016

Related U.S. Application Data

(63) Continuation of application No. 13/086,389, filed on Apr. 13, 2011.
(Continued)

(51) Int. Cl.
*A61B 18/14* (2006.01)
*A61B 18/24* (2006.01)
(Continued)

(52) U.S. Cl.
CPC ........ *A61B 18/1492* (2013.01); *A61B 17/122* (2013.01); *A61B 17/12013* (2013.01);
(Continued)

(58) Field of Classification Search
CPC .......... A61B 2018/00345; A61B 2018/00351; A61B 2018/00357; A61B 2018/00363;
(Continued)

(56) References Cited

U.S. PATENT DOCUMENTS

| 3,496,932 A | 2/1970 | Prisk et al. |
| 3,677,597 A | 7/1972 | Stipek |

(Continued)

FOREIGN PATENT DOCUMENTS

| CN | 2624615 Y | 7/2004 |
| CN | 101242785 A | 8/2008 |

(Continued)

OTHER PUBLICATIONS

Extended European Search Report dated Jul. 10, 2015, for European Patent Application No. 15153029.2, filed on Mar. 25, 2008, 6 pages.
(Continued)

*Primary Examiner* — Eun Hwa Kim
(74) *Attorney, Agent, or Firm* — Cooley LLP

(57) ABSTRACT

Described here are systems and methods for affecting tissue within a body to form a lesion. Some systems comprise tissue-affecting devices, devices that guide the advancement of the tissue-affecting elements to a target tissue region, devices that locate and secure tissue, and devices that help position the tissue-affecting devices along the target tissue. The methods described here comprise advancing a first tissue-affecting device to a first surface of a target tissue, advancing a second tissue-affecting device to a second surface of the target tissue, and positioning the first and second devices so that a lesion may be formed in the tissue between them. In some variations, the devices, systems, and methods described here are used to treat atrial fibrillation by ablating fibrillating tissue from an endocardial surface and an epicardial surface of a heart. Methods of closing, occluding, and/or removing the left atrial appendage are also described.

21 Claims, 32 Drawing Sheets

Related U.S. Application Data

(60) Provisional application No. 61/323,796, filed on Apr. 13, 2010, provisional application No. 61/323,801, filed on Apr. 13, 2010, provisional application No. 61/323,816, filed on Apr. 13, 2010.

(51) Int. Cl.
| | | |
|---|---|---|
| *A61N 7/02* | (2006.01) | |
| *A61B 18/18* | (2006.01) | |
| *A61B 17/12* | (2006.01) | |
| *A61B 17/122* | (2006.01) | |
| A61B 17/00 | (2006.01) | |
| A61B 18/02 | (2006.01) | |
| A61B 18/00 | (2006.01) | |
| A61N 7/00 | (2006.01) | |
| A61M 25/01 | (2006.01) | |

(52) U.S. Cl.
CPC .. *A61B 17/12122* (2013.01); *A61B 17/12131* (2013.01); *A61B 18/1815* (2013.01); *A61B 18/24* (2013.01); *A61N 7/022* (2013.01); A61B 17/12136 (2013.01); A61B 17/12172 (2013.01); A61B 17/12195 (2013.01); A61B 18/02 (2013.01); A61B 2017/00084 (2013.01); A61B 2017/00243 (2013.01); A61B 2017/00247 (2013.01); A61B 2017/00477 (2013.01); A61B 2017/00876 (2013.01); A61B 2018/00279 (2013.01); A61B 2018/00357 (2013.01); A61B 2018/00363 (2013.01); A61B 2018/00791 (2013.01); A61B 2018/0212 (2013.01); A61B 2018/1407 (2013.01); A61B 2018/1861 (2013.01); A61M 25/0127 (2013.01); A61N 7/00 (2013.01); A61N 7/02 (2013.01)

(58) Field of Classification Search
CPC ............ A61B 17/122; A61B 17/12013; A61B 17/12122; A61B 17/12131; A61B 17/12195; A61B 17/12172; A61B 2017/00247; A61B 2017/00084; A61B 2017/12172; A61B 2017/00876; A61B 2017/00477; A61B 2017/00243; A61B 18/02; A61B 18/1492; A61B 18/1815; A61B 18/24; A61N 7/11; A61N 7/022; A61N 7/02; A61M 25/0127
See application file for complete search history.

(56) References Cited

U.S. PATENT DOCUMENTS

| | | |
|---|---|---|
| 3,802,074 A | 4/1974 | Hoppe |
| 3,841,685 A | 10/1974 | Kolodziej |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,249,536 A | 2/1981 | Vega |
| 4,257,278 A | 3/1981 | Papadofrangakis et al. |
| 4,319,562 A | 3/1982 | Crosby |
| 4,428,375 A | 1/1984 | Ellman |
| 4,596,530 A | 6/1986 | McGlinn |
| 4,662,377 A | 5/1987 | Heilman et al. |
| 4,765,341 A | 8/1988 | Mower et al. |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,181,919 A | 1/1993 | Bergman et al. |
| 5,226,535 A | 7/1993 | Roshdy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,279,539 A | 1/1994 | Bohan et al. |
| 5,281,238 A | 1/1994 | Chin et al. |
| 5,300,078 A | 4/1994 | Buelna |
| 5,306,234 A | 4/1994 | Johnson |
| 5,318,578 A | 6/1994 | Hasson |
| 5,336,229 A | 8/1994 | Noda |
| 5,336,231 A | 8/1994 | Adair |
| 5,336,252 A | 8/1994 | Cohen |
| 5,385,156 A | 1/1995 | Oliva |
| 5,387,219 A | 2/1995 | Rappe |
| 5,398,944 A | 3/1995 | Holster |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,361 A | 9/1995 | Preissman |
| 5,449,637 A | 9/1995 | Kadry |
| 5,458,597 A | 10/1995 | Edwards et al. |
| 5,465,731 A | 11/1995 | Bell et al. |
| 5,494,240 A | 2/1996 | Waugh |
| 5,498,228 A | 3/1996 | Royalty et al. |
| 5,522,819 A | 6/1996 | Graves et al. |
| 5,540,711 A | 7/1996 | Kieturakis et al. |
| 5,545,178 A | 8/1996 | Kensey et al. |
| 5,571,161 A | 11/1996 | Starksen |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,636,780 A | 6/1997 | Green et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,348 A | 11/1997 | Diener |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,741,281 A | 4/1998 | Martin |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,788,715 A | 8/1998 | Watson, Jr. et al. |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |

(56) References Cited

U.S. PATENT DOCUMENTS

| | | |
|---|---|---|
| 5,814,052 A | 9/1998 | Nakao et al. |
| 5,823,946 A | 10/1998 | Chin |
| 5,827,216 A | 10/1998 | Igo et al. |
| 5,840,059 A | 11/1998 | March et al. |
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,895,404 A | 4/1999 | Ruiz |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,957,936 A | 9/1999 | Yoon et al. |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,027,499 A | 2/2000 | Johnston et al. |
| 6,045,570 A | 4/2000 | Epstein et al. |
| 6,048,329 A | 4/2000 | Thompson et al. |
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,840,246 B2 | 1/2005 | Downing |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,597,705 B2 | 10/2009 | Forsberg et al. |
| 7,608,091 B2 | 10/2009 | Goldfarb et al. |
| 7,610,104 B2 | 10/2009 | Kaplan et al. |
| 7,618,425 B2 | 11/2009 | Yamamoto et al. |
| 7,681,579 B2 | 3/2010 | Schwartz |
| 7,722,641 B2 | 5/2010 | van der Burg et al. |
| 7,736,347 B2 | 6/2010 | Kaplan et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 7,967,808 B2 | 6/2011 | Fitzgerald et al. |
| 8,070,693 B2 | 12/2011 | Ayala et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,500,768 B2 | 8/2013 | Cohen |
| 8,636,767 B2 | 1/2014 | McClain |
| 8,715,302 B2 | 5/2014 | Ibrahim et al. |
| 8,721,663 B2 | 5/2014 | Kaplan et al. |
| 8,771,297 B2 | 7/2014 | Miller et al. |
| 8,795,297 B2 | 8/2014 | Liddicoat et al. |
| 8,795,310 B2 | 8/2014 | Fung et al. |
| 8,814,778 B2 | 8/2014 | Kiser et al. |
| 8,932,276 B1 | 1/2015 | Morriss et al. |
| 8,961,543 B2 | 2/2015 | Friedman et al. |
| 8,974,473 B2 | 3/2015 | Kaplan et al. |
| 8,986,278 B2 | 3/2015 | Fung et al. |

(56) References Cited

U.S. PATENT DOCUMENTS

| | | |
|---|---|---|
| 8,986,325 B2 | 3/2015 | Miller et al. |
| 8,996,133 B2 | 3/2015 | Kaplan et al. |
| 9,089,324 B2 | 7/2015 | McCaw et al. |
| 9,186,174 B2 | 11/2015 | Krishnan et al. |
| 9,198,664 B2 | 12/2015 | Fung et al. |
| 9,198,683 B2 | 12/2015 | Friedman et al. |
| 9,271,819 B2 | 3/2016 | Liddicoat et al. |
| 9,339,295 B2 | 5/2016 | Fung et al. |
| 9,408,608 B2 | 8/2016 | Clark et al. |
| 9,498,223 B2 | 11/2016 | Miller et al. |
| 9,956,036 B2 | 5/2018 | Whayne et al. |
| 10,136,909 B2 | 11/2018 | Ibrahim et al. |
| 2001/0003795 A1 | 6/2001 | Suresh et al. |
| 2001/0007070 A1 | 7/2001 | Stewart et al. |
| 2001/0025132 A1 | 9/2001 | Alferness et al. |
| 2002/0002329 A1 | 1/2002 | Avitall |
| 2002/0017306 A1 | 2/2002 | Cox et al. |
| 2002/0022860 A1 | 2/2002 | Borillo et al. |
| 2002/0032440 A1* | 3/2002 | Hooven ............ A61B 18/1445 606/41 |
| 2002/0045895 A1 | 4/2002 | Sliwa, Jr. et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2002/0123771 A1 | 9/2002 | Ideker et al. |
| 2002/0128639 A1 | 9/2002 | Pless et al. |
| 2002/0147456 A1 | 10/2002 | Diduch et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0078465 A1 | 4/2003 | Pai et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0120337 A1 | 6/2003 | Van Tassel et al. |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0220667 A1 | 11/2003 | Van der Burg et al. |
| 2003/0236535 A1 | 12/2003 | Onuki et al. |
| 2004/0024414 A1 | 2/2004 | Downing |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059280 A1 | 3/2004 | Makower et al. |
| 2004/0059352 A1 | 3/2004 | Burbank et al. |
| 2004/0064138 A1 | 4/2004 | Grabek |
| 2004/0068267 A1 | 4/2004 | Harvie et al. |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0122467 A1 | 6/2004 | Van Tassel et al. |
| 2004/0148020 A1 | 7/2004 | Vidlund et al. |
| 2004/0158127 A1 | 8/2004 | Okada |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033274 A1 | 2/2005 | Pless et al. |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043743 A1 | 2/2005 | Dennis |
| 2005/0043745 A1 | 2/2005 | Alferness et al. |
| 2005/0080454 A1 | 4/2005 | Drews et al. |
| 2005/0085843 A1 | 4/2005 | Opolski et al. |
| 2005/0101984 A1 | 5/2005 | Chanduszko et al. |
| 2005/0107824 A1 | 5/2005 | Hillstead et al. |
| 2005/0113861 A1 | 5/2005 | Corcoran et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0165466 A1 | 7/2005 | Morris et al. |
| 2005/0187545 A1 | 8/2005 | Hooven et al. |
| 2005/0228422 A1 | 10/2005 | Machold et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0009756 A1 | 1/2006 | Francischelli et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0095066 A1 | 5/2006 | Chang et al. |
| 2006/0100545 A1 | 5/2006 | Ayala et al. |
| 2006/0106278 A1 | 5/2006 | Machold et al. |
| 2006/0200120 A1 | 9/2006 | DiCarlo et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2007/0010829 A1 | 1/2007 | Nobles et al. |
| 2007/0016228 A1 | 1/2007 | Salas |
| 2007/0027456 A1 | 2/2007 | Gartner et al. |
| 2007/0038229 A1 | 2/2007 | de la Torre |
| 2007/0043344 A1 | 2/2007 | McAuley |
| 2007/0060951 A1 | 3/2007 | Shannon |
| 2007/0083082 A1 | 4/2007 | Kiser et al. |
| 2007/0083194 A1 | 4/2007 | Kunis et al. |
| 2007/0083225 A1 | 4/2007 | Kiser et al. |
| 2007/0083230 A1 | 4/2007 | Javois |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0203554 A1 | 8/2007 | Kaplan et al. |
| 2007/0219546 A1 | 9/2007 | Mody et al. |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin, Jr. |
| 2008/0009843 A1 | 1/2008 | de la Torre |
| 2008/0015406 A1 | 1/2008 | Dlugos et al. |
| 2008/0015571 A1* | 1/2008 | Rubinsky ........... A61B 18/1477 606/42 |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0058635 A1 | 3/2008 | Halperin et al. |
| 2008/0065156 A1 | 3/2008 | Hauser et al. |
| 2008/0097489 A1 | 4/2008 | Goldfarb et al. |
| 2008/0125795 A1 | 5/2008 | Kaplan et al. |
| 2008/0154260 A1 | 6/2008 | Hoof |
| 2008/0177381 A1 | 7/2008 | Navia et al. |
| 2008/0214889 A1 | 9/2008 | Saadat et al. |
| 2008/0221593 A1 | 9/2008 | Liddicoat et al. |
| 2008/0228265 A1 | 9/2008 | Spence et al. |
| 2008/0243183 A1* | 10/2008 | Miller ............ A61B 17/12013 606/228 |
| 2008/0245371 A1 | 10/2008 | Gruber |
| 2008/0269782 A1 | 10/2008 | Stefanchik et al. |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0088728 A1 | 4/2009 | Dollar et al. |
| 2009/0088778 A1 | 4/2009 | Miyamoto et al. |
| 2009/0093809 A1 | 4/2009 | Anderson et al. |
| 2009/0124847 A1 | 5/2009 | Doty et al. |

(56) References Cited

U.S. PATENT DOCUMENTS

| | | |
|---|---|---|
| 2009/0143791 A1 | 6/2009 | Miller et al. |
| 2009/0157118 A1 | 6/2009 | Miller et al. |
| 2009/0182326 A1 | 7/2009 | Zenati et al. |
| 2009/0196696 A1 | 8/2009 | Otsuka et al. |
| 2010/0069925 A1 | 3/2010 | Friedman et al. |
| 2010/0094314 A1 | 4/2010 | Hernlund |
| 2010/0174296 A1 | 7/2010 | Vakharia et al. |
| 2010/0191253 A1 | 7/2010 | Oostman et al. |
| 2010/0331820 A1 | 12/2010 | Giuseppe et al. |
| 2011/0034804 A1 | 2/2011 | Hubregtse et al. |
| 2011/0060350 A1 | 3/2011 | Powers et al. |
| 2011/0087270 A1 | 4/2011 | Penner et al. |
| 2011/0092997 A1 | 4/2011 | Kang |
| 2011/0106107 A1 | 5/2011 | Binmoeller et al. |
| 2011/0112537 A1 | 5/2011 | Bernstein et al. |
| 2011/0144660 A1 | 6/2011 | Liddicoat et al. |
| 2011/0282250 A1 | 11/2011 | Fung et al. |
| 2011/0295060 A1 | 12/2011 | Zenati et al. |
| 2012/0022558 A1 | 1/2012 | Friedman et al. |
| 2012/0095434 A1 | 4/2012 | Fung et al. |
| 2012/0158022 A1 | 6/2012 | Kaplan et al. |
| 2012/0209300 A1 | 8/2012 | Torrie |
| 2012/0330351 A1 | 12/2012 | Friedman et al. |
| 2013/0144311 A1 | 6/2013 | Fung et al. |
| 2013/0218156 A1 | 8/2013 | Kassab et al. |
| 2013/0296880 A1 | 11/2013 | Kelley et al. |
| 2014/0018831 A1 | 1/2014 | Kassab et al. |
| 2014/0171733 A1 | 6/2014 | Sternik |
| 2014/0222138 A1 | 8/2014 | Machold et al. |
| 2014/0276911 A1 | 9/2014 | Smith et al. |
| 2014/0303721 A1 | 10/2014 | Fung et al. |
| 2014/0316385 A1 | 10/2014 | Longoria et al. |
| 2014/0330074 A1 | 11/2014 | Morriss et al. |
| 2014/0336572 A1 | 11/2014 | Heisel et al. |
| 2014/0336676 A1 | 11/2014 | Pong et al. |
| 2014/0364901 A1 | 12/2014 | Kiser et al. |
| 2014/0364907 A1 | 12/2014 | White et al. |
| 2014/0371741 A1 | 12/2014 | Longoria et al. |
| 2015/0018853 A1 | 1/2015 | Friedman et al. |
| 2015/0025312 A1 | 1/2015 | de Canniere |
| 2015/0173765 A1 | 1/2015 | Friedman et al. |
| 2015/0119884 A1 | 4/2015 | Fung et al. |
| 2015/0157328 A1 | 6/2015 | Miller et al. |
| 2015/0182225 A1 | 7/2015 | Morejohn et al. |
| 2015/0190135 A1 | 7/2015 | Ibrahim et al. |
| 2015/0223813 A1 | 8/2015 | Willisamson et al. |
| 2015/0250482 A1 | 9/2015 | Slaughter et al. |
| 2015/0272618 A1 | 10/2015 | Fung et al. |
| 2015/0374380 A1 | 12/2015 | Miller et al. |
| 2016/0008001 A1 | 1/2016 | Winkler et al. |
| 2016/0106421 A1 | 4/2016 | Eliachar et al. |
| 2016/0120549 A1 | 5/2016 | Fung et al. |
| 2016/0278781 A1 | 9/2016 | Fung et al. |
| 2016/0302793 A1 | 10/2016 | Fung et al. |
| 2016/0310144 A1 | 10/2016 | Kimura et al. |
| 2016/0310145 A1 | 10/2016 | Clark et al. |
| 2016/0317155 A1 | 11/2016 | Kimura et al. |
| 2016/0346028 A1 | 12/2016 | Rogers et al. |
| 2017/0290592 A1 | 10/2017 | Miller et al. |
| 2018/0008342 A1 | 1/2018 | Ibrahim et al. |

FOREIGN PATENT DOCUMENTS

| | | |
|---|---|---|
| CN | 101262823 B | 12/2011 |
| EP | 0 598 219 A2 | 5/1994 |
| EP | 0 598 219 A3 | 5/1994 |
| EP | 0 598 219 B1 | 5/1994 |
| EP | 0 625 336 A2 | 11/1994 |
| EP | 0 705 566 A1 | 4/1996 |
| EP | 1 010 397 A1 | 6/2000 |
| GB | 1 506 142 A | 4/1978 |
| JP | H-6-319742 A | 11/1994 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-512071 A | 4/2002 |
| JP | 2002-540834 A | 12/2002 |
| JP | 2002-540901 A | 12/2002 |
| JP | 2003-225241 A | 8/2003 |
| JP | 2004-000601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| JP | 2007-534355 A | 11/2007 |
| JP | 2008-534085 A | 8/2008 |
| JP | 2010-523171 A | 7/2010 |
| JP | 2012-522596 A | 9/2012 |
| WO | WO-94/01045 A1 | 1/1994 |
| WO | WO-94/04079 A1 | 3/1994 |
| WO | WO-94/08514 A1 | 4/1994 |
| WO | WO-96/04854 A1 | 2/1996 |
| WO | WO-96/40356 A1 | 12/1996 |
| WO | WO-97/11644 A1 | 4/1997 |
| WO | WO-97/43957 A1 | 11/1997 |
| WO | WO-99/53845 A1 | 10/1999 |
| WO | WO-00/59383 A1 | 10/2000 |
| WO | WO-00/61202 A1 | 10/2000 |
| WO | WO-03/028558 A2 | 4/2003 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034802 A2 | 4/2005 |
| WO | WO-2005/034802 A3 | 4/2005 |
| WO | WO-2006/096805 A1 | 9/2006 |
| WO | WO-2006/110734 A2 | 10/2006 |
| WO | WO-2006/115689 A1 | 11/2006 |
| WO | WO-2007/001936 A2 | 1/2007 |
| WO | WO-2007/001936 A3 | 1/2007 |
| WO | WO-2007/037516 A2 | 4/2007 |
| WO | WO-2007/037516 A3 | 4/2007 |
| WO | WO-2007/056502 A1 | 5/2007 |
| WO | WO-2008/017080 A2 | 2/2008 |
| WO | WO-2008/017080 A3 | 2/2008 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2008/150346 A1 | 12/2008 |
| WO | WO-2009/039191 A2 | 3/2009 |
| WO | WO-2009/045265 A1 | 4/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/007600 A1 | 1/2010 |
| WO | WO-2010/048141 A2 | 4/2010 |
| WO | WO-2010/048141 A3 | 4/2010 |
| WO | WO-2010/115030 A1 | 10/2010 |
| WO | WO-2011/129893 A1 | 10/2011 |
| WO | WO-2012/170652 A1 | 12/2012 |
| WO | WO-2014/164028 A1 | 10/2014 |

OTHER PUBLICATIONS

Extended European Search Report dated Feb. 10, 2017, for EP Application No. 10 759 425.1, filed on Apr. 1, 2010, 7 pages.

Extended European Search Report dated Oct. 30, 2017, for EP Application No. 11 769 217.8, filed on Apr. 13, 2011, 12 pages.

Extended European Search Report dated Oct. 30, 2017, for EP Application No. 11 769 218.6, filed on Apr. 13, 2011, 11 pages.

International Search Report dated Feb. 27, 2007, for PCT Application No. PCT/US2008/003938, filed on Mar. 25, 2008, 5 pages.

International Search Report dated Jun. 1, 2010, for PCT Application No. PCT/US2010/029668, filed on Apr. 1, 2010, 2 pages.

International Search Report dated Oct. 3, 2011, for PCT Patent Application No. PCT/US2011/00677, filed on Apr. 13, 2011, 5 pages.

Written Opinion of the International Searching Authority dated Feb. 27, 2007, for PCT Application No. PCT/US2008/003938, filed on Mar. 25, 2008, 10 pages.

(56) References Cited

OTHER PUBLICATIONS

Written Opinion of the International Searching Authority dated Jun. 1, 2010, for PCT Application No. PCT/US2010/029668, filed on Apr. 1, 2010, 8 pages.
Written Opinion of the International Search Authority dated Oct. 3, 2011, for PCT Application No. PCT/US2011/00677, filed on Apr. 13, 2011, 6 pages.
Final Office Action dated Jun. 8, 2017, for U.S. Appl. No. 14/625,540, filed Feb. 18, 2015, 14 pages.
Final Office Action dated Mar. 17, 2016, for U.S. Appl. No. 12/363,359, filed Jan. 30, 2009, 10 pages.
Non-Final Office Action dated Mar. 29, 2013, for U.S. Appl. No. 12/752,873, filed Apr. 1, 2010, 16 pages.
Non-Final Office Action dated Dec. 2, 2016, for U.S. Appl. No. 14/625,540, filed Feb. 18, 2015, 20 pages.
afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.
Al-Saady, N.M. et al. (1999). "Left Atrial Appendage: Structure, Function, and Role in Thromboembolism," *Heart* 82:547-554.
Albers, G.W. (Jul. 11, 1994). "Atrial Fibrillation and Stroke: Three New Studies, Three Remaining Questions," *Arch Intern Med* 154:1443-1448.
Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.
Aronow, W.S. et al. (Apr. 2009). "Atrial Fibrillation: The New Epidemic of the Age-ing World," *Journal of Atrial Fibrillation* 1(6):337-361.
Australian Office Action dated Dec. 19, 2014, for Australian Patent Application No. 2011241103, filed on Apr. 13, 2011, 4 pages.
Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.
Bath, P.M.W. et al. (2005). "Current Status of Stroke Prevention in Patients with Atrial Fibrillation," *European Heart Journal Supplements* 7(Supplement C):C12-C18.
Benjamin, B.A. et al. (1994). "Effect of Bilateral Atrial Appendectomy on Postprandial Sodium Excretion in Conscious Monkeys," *Society for Experimental Biology and Medicine* 206: 1 page.
Beygui, F. et al. (2005, e-pub. Oct. 21, 2005). "Multimodality Imaging of Percutaneous Closure of the Left Atrial Appendage," *Clinical Vignette*, 1 page.
Bisleri, G. et al. (Jun. 3, 2005). "Innovative Monolateral Approach for Closed-Chest Atrial Fibrillation Surgery," *The Annals of Thoracic Surgery* 80:e22-e25.
Björk, V.O. et al. (Aug. 1961). "Sequelae of Left Ventricular Puncture with Angiocardiography," *Circulation* 24:204-212.
Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.
Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.
Bonanomi, G. et al. (Jan. 1, 2003). "Left Atrial Appendectomy and Maze," *Journal of the American College of Cardiology* 41(1):169-171.
Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Circulation* 98:1949-1984.
Botham, R.J. et al. (May 1959). "Pericardial Tamponade Following Percutaneous Left Ventricular Puncture," *Circulation* 19:741-744.
Brock, R. et al. (1956). "Percutaneous Left Ventricular Puncture in the Assessment of Aortic Stenosis," *Thorax* 11:163-171.
Burke, R.P. et al. (1992). "Improved Surgical Approach to Left Atrial Appendage Aneurysm," *Journal of Cardiac Surgery* 7(2):104-107.
Canaccord Adams. (Aug. 11, 2008). "A-Fib: Near a Tipping Point," 167 pages.
Chung, M.K. (Jul. 2003). "Current Clinical Issues in Atrial Fibrillation," *Cleveland Clinic Journal of Medicine* 70(Supp. 3):S6-S11.
Coffin, L.H. (Jun. 1985). "Use of the Surgical Stapler to Obliterate the Left Atrial Appendage," *Surgery, Gynecology & Obstetric* 160:565-566.
Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.
Costa, R. et al. (2006). "Bi-Atrial Subxiphoid Epicardial Pacemaker in Superior Vena Cava Syndrome," *Arq. Bras. Cardiol.* 87:e45-e47.
Cox, J.L. et al. (Apr. 1991). "The Surgical Treatment of Atrial Fibrillation: IV. Surgical Technique," *J. Thorac. Cardiovasc. Surg.* 101(4):584-592.
Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.
Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.
Cox, J.L. et al. (Nov. 1999). "Impact of the Maze Procedure on the Stroke Rate in Patients with Atrial Fibrillation," *J. Thorac. Cardiovasc. Surg.* 118:833-840.
Cox, J.L. et al. (2004). "The Role of Surgical Intervention in the Management of Atrial Fibrillation," *Texas Heart Institute Journal* 31(3):257-265.
Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.
D'Avila, A. et al. (Apr. 2003). "Pericardial Anatomy for the Interventional Electrophysiologist," *Journal of Cardiovascular Electrophysiology* 14(4):422-430.
D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.
Demaria, A.N. et al. (Dec. 17, 2003). "Highlights of the Year JACC 2003," *Journal of the American College of Cardiology* 42(12):2156-2166.
Deneu, S. et al. (Jul. 11, 1999). "Catheter Entrapment by Atrial Suture During Minimally Invasive Port-access Cardiac Surgery," *Canadian Journal of Anesthesia* 46(10):983-986.
Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.
Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.
Donnino, R. et al. (2007). "Left Atrial Appendage Thrombus Outside of a 'Successful' Ligation," *European Journal of Echocardiography* pp. 1-2.
Dullum, M.K.C. et al. (1999). "Xyphoid MIDCAB: Report of the Technique and Experience with a Less Invasive MIDCAB Procedure," *Heart Surgery Forum* 2(1):77-81.
Feinberg, W.M. et al. (Mar. 13, 1995). "Prevalence, Age Distribution, and Gender of Patients With Atrial Fibrillation," *Arch Intern Med* 155:469-473.
Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.
Final Office Action dated Jun. 22, 2009, for U.S. Appl. No. 10/963,371, filed Oct. 11, 2004, 11 pages.

(56) References Cited

OTHER PUBLICATIONS

Final Office Action dated Apr. 14, 2010, for U.S. Appl. No. 11/600,671, filed Nov. 15, 2006, 7 pages.
Final Office Action dated Jul. 21, 2010, for U.S. Appl. No. 11/400,714, filed Apr. 7, 2006, 10 pages.
Final Office Action dated Apr. 26, 2011, for U.S. Appl. No. 12/037,802, filed Feb. 26, 2008, 9 pages.
Final Office Action dated Sep. 20, 2011, for U.S. Appl. No. 12/212,511, filed Sep. 17, 2008, 8 pages.
Final Office Action dated Oct. 28, 2011, for U.S. Appl. No. 12/055,213, filed Mar. 25, 2008, 15 pages.
Final Office Action dated May 4, 2012, for U.S. Appl. No. 12/363,359, filed Jan. 30, 2009, 10 pages.
Final Office Action dated Nov. 14, 2014, for U.S. Appl. No. 12/363,359, filed Jan. 30, 2009, 10 pages.
Final Office Action dated May 16, 2012, for U.S. Appl. No. 12/363,381, filed Jan. 30, 2009, 8 pages.
Final Office Action dated Jul. 11, 2012, for U.S. Appl. No. 13/033,532, filed Feb. 23, 2011, 8 pages.
Final Office Action dated Jul. 24, 2012, for U.S. Appl. No. 12/212,511, filed Sep. 17, 2008, 6 pages.
Final Office Action dated Oct. 18, 2012, for U.S. Appl. No. 12/124,023, filed May 20, 2008, 15 pages.
Final Office Action dated Nov. 8, 2013, for U.S. Appl. No. 12/037,802, filed Feb. 26, 2008, 15 pages.
Final Office Action dated Jan. 13, 2014, for U.S. Appl. No. 12/752,873, filed Apr. 1, 2010, 10 pages.
Final Office Action dated Oct. 22, 2013 for U.S. Appl. No. 13/086,390, filed Apr. 13, 2011, 6 pages.
Final Office Action dated Aug. 12, 2014, for U.S. Appl. No. 13/033,532, filed Feb. 23, 2011, 6 pages.
Fisher, D.C. et al. (Dec. 1998). "Large Gradient Across a Partially Ligated Left Atrial Appendage," *Journal of the American Society of Echocardiography* 11(12):1163-1165.
Friberg, L. et al. (2006). "Stroke Prophylaxis in Atrial Fibrillation: Who Gets it and Who Does Not?" *European Heart Journal* 27:1954-1964.
Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.
Fuster, V. et al. (Oct. 2001). "ACC/AHA/ESC Guidelines for the Management of Patients with Atrial Fibrillation," *European Heart Journal* 22(20):1852-1923.
Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.
Gardiner, G.A. Jr. et al. (Apr. 1986). "Complications of Transluminal Angioplasty," *Radiology* 159(1):201-208.
Gillinov, A.M. (Feb. 2007). "Advances in Surgical Treatment of Atrial Fibrillation," *Stroke* 38(part 2):618-623.
Gilman, R.A. et al. (Apr. 1963). "Direct Left Ventricular Puncture," *California Medicine* 98(4):200-203.
Goodwin, W.E. et al. (Nov. 1950). "Translumbar Aortic Puncture and Retrograde Catheterization of the Aorta in Aortography and Renal Arteriography," *Annals of Surgery* 132(5):944-958.
Gottlieb, L.K. et al. (Sep. 12, 1994). "Anticoagulation in Atrial Fibrillation," *Arch Intern Med.* 154:1945-1953.
Graffigna, A. et al. (1993). "Surgical Treatment of Wolff-Parkinson-White Syndrome: Epicardial Approach Without the Use of Cardiopulmonary Bypass," *J. Card. Surg.* 8:108-116.
Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.
Halperin, J.L. et al. (Aug. 1988). "Atrial Fibrillation and Stroke: New Ideas, Persisting Dilemmas," *Journal of the American Heart Association* 19(8):937-941.

Halperin, J.L. et al. (Oct. 1, 2003). "Obliteration of the Left Atrial Appendage for Prevention of Thromboembolism," *Journal of the American College of Cardiology* 42(7):1259-1261.
Hammill, S.C. (May 2006). "Epicardial Ablation: Reducing the Risks," *J. Cardiovasc. Electrophysiol.* 17:550-552.
Hara, H. et al. (Jan. 2008). "Percutaneous Left Atrial Appendage Obliteration," *JACC: Cardiovascular Imagin* 1(1):92-93.
Hart, R.G. et al. (Nov. 2, 1999). "Atrial Fibrillation and Thromboembolism: A Decade of Progress in Stroke Prevention," *Annals of Internal Medicine* 131(9):688-695.
Hart, R.G. et al. (Mar. 2001). "Atrial Fibrillation and Stroke: Concepts and Controversies," *Stroke* 32:803-808.
Hart, R.G. (Sep. 11, 2003). "Atrial Fibrillation and Stroke Prevention," *The New England Journal of Medicine* 349(11):1015-1016.
Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at The Canadian Cardiovascular Congress 2003, Toronto, Canada, Abstract No. 666, 2 pages.
Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.
Hein, R. et al. (2005). "Patent Foramen Ovale and Left Atrial Appendage: New Devices and Methods for Closure," *Pediatric Cardiology* 26(3):234-240.
Heist, E.K. et al. (Nov. 2006). "Analysis of the Left Atrial Appendage by Magnetic Resonance Angiography in Patients with Atrial Fibrillation," *Heart Rhythm* 3(11):1313-1318.
Ho, I. et al. (Apr. 24, 2007). "Percutaneous Epicardial Mapping Ablation of a Posteroseptal Accessory Pathway," *Circulation* 115:e418-e421.
Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.
Hoit, B.D. et al. (Jan. 1993). "Altered Left Atrial Compliance After Atrial Appendectomy. Influence on Left Atrial and Ventricular Filling," *Circulation Research* 72(1):167-175.
Inoue, Y. et al. (Jul.-Aug. 1997). "Video Assisted Thoracoscopic and Cardioscopic Radiofrequency Maze Ablation," *Asaio Journal* 43(4):334-337, Abstract Only.
International Search Report dated Jul. 13, 2011, for PCT Patent Application No. PCT/US11/00676, filed on Apr. 13, 2011, 2 pages.
Jaïs, P. et al. (2003). "Radiofrequency Ablation for Atrial Fibrillation," *European Society of Cardiology* 5(Supplement H):H34-H39.
Johnson, W.D. et al. (2000). "The Left Atrial Appendage: Our Most Lethal Human Attachment! Surgical Implications," *Euro. J. Cardiothoracic. Surg.* 17:718-722.
Jongbloed, M.R.M. et al. (2005). "Clinical Applications of Intracardiac Echocardiography in Interventional Procedures," *Heart* 91:981-990.
Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.
Kanderian, A.S. et al. (2008). "Success of Surgical Left Atrial Appendage Closure: Assessment by Transesophageal Echocardiography," *Journal of the American College of Cardiology* 52(11):924-929.
Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.
Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.
Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.
Kerut, E.K. et al. (Jul. 2008). "Anatomy of the Left Atrial Appendage," *Echocardiography* 25(6):669-673.

(56) References Cited

OTHER PUBLICATIONS

Khargi, K. et al. (2005). "Surgical Treatment of Atrial Fibrillation: A Systematic Review," *European Journal of Cardiothoracic Surgery* 27:258-265.
Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.
Kistler, P.M. et al. (May 2007). "The Left Atrial Appendage: Not Just an Innocent Bystander," *J. Cardiovasc Electrophysiol* 18(5):465-466.
Klein, H. et al. (Apr. 1990). "The Implantable Automatic Cardioverter-Defibrillator," *Herz* 15(2):111-125, Abstract Only.
Kolb, C. et al. (Feb. 2004). "Incidence of Antitachycardia Therapy Suspension Due to Magnet Reversion in Implantable Cardioverter Defibrillators," *Pace* 27:221-223.
Krikorian, J.G. et al. (Nov. 1978). "Pericardiocentesis," *Am. J. Med.* 65(5):808-814.
Krum, D. et al. (2004). "Visualization of Remnants of the left Atrial Appendage Following Epicardial Surgical Removal," *Heart Rhythm* 1:249.
Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.
Lacomis, J.M. et al. (2007, e-pub. Oct. 17, 2007). "Dynamic Multidimensional Imaging of the Human Left Atrial Appendage," *Europace* 9:1134-1140.
Lee, R. et al. (1999). "The Closed Heart MAZE: A Nonbypass Surgical Technique," *The Annals of Thoracic Surgery* 67:1696-1702.
Levinson, M.L. et al. (1998). "Minimally Invasive Atrial Septal Defect Closure Using the Subxyphoid Approach," *Heart Surg. Forum* 1(1):49-53, Abstract Only.
Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.
Li, H. (2007). "Magnet Decoration, Beautiful But Potentially Dangerous for Patients with Implantable Pacemakers or Defibrillators," *Heart Rhythm* 4(1):5-6.
Lindsay, B.D. (1996). "Obliteration of the Left Atrial Appendage: A Concept Worth Testing," *The Annals of Thoracic Surgery* 61:515-516.
Lip, G.Y.H. et al. (Jun. 2001). "Thromboprophylaxis for Atrial Flutter," *European Heart Journal* 22(12):984-987.
Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.
Macris, M. et al. (Jan. 1999). "Minimally Invasive Access of the Normal Pericardium: Initial Clinical Experience with a Novel Device," *Clin. Cardiol.* 22(Suppl. I):I-36-I-39.
Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I):I-17-I-22.
Mannam, A.P. et al. (Apr. 1, 2002). "Safety of Subxyphoid Pericardial Access Using a Blunt-Tip Needle," *The American Journal of Cardiology* 89:891-893.
Mattox, K.L. et al. (May 1997). "Newer Diagnostic Measure and Emergency Management," *Ches Surg Clin N Am.* 7(2):213-226, Abstract Only.
McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.
McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751.
McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.

Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.
Miller, P.S.J. et al. (Feb. 2005). "Are Cost Benefits of Anticoagulation for Stroke Prevention in Atrial Fibrillation Underestimated?" *Stroke* 36:360-366.
Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.
Morris, J.J. Jr. (1979). "Transvenous versus Transthoracic Cardiac Pacing," Chapter 16 in *Cardiac Pacing: A Concise Guide to Clinical Practice*, pp. 239-245.
Mráz, T. et al. (Apr. 2007). "Role of Echocardiography in Percutaneous Occlusion of the left Atrial Appendage," *Echocardiography* 24(4):401-404.
Naclerio, E.A. et al. (1979). "Surgical Techniques for Permanent Ventricular Pacing," Chapter 10 in *Cardiac Pacing: A Concise Guide to Clinical Practice*, pp. 145-168.
Nakai, T. et al. (May 7, 2002). "Percutaneous Left Atrial Appendage Occlusion (PLAATO) for Preventing Cardioembolism: First Experience in Canine Model," *Circulation* 105:2217-2222.
Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.
Non-Final Office Action dated Feb. 5, 2014 for U.S. Appl. No. 13/086,389, filed Apr. 13, 2011, 16 pages.
Non-Final Office Action dated Mar. 13, 2008 for U.S. Appl. No. 10/963,371, filed Oct. 11, 2004, 14 pages.
Non-Final Office Action dated Aug. 6, 2008 for U.S. Appl. No. 10/963,371, filed Oct. 11, 2004, 14 pages.
Non-Final Office Action dated Jun. 26, 2009, for U.S. Appl. No. 11/600,671, filed Nov. 15, 2006, 9 pages.
Non-Final Office Action dated Dec. 30, 2009, for U.S. Appl. No. 11/400,714, filed Apr. 7, 2006, 8 pages.
Non-Final Office Action dated Jul. 22, 2010, for U.S. Appl. No. 12/037,802, filed Feb. 26, 2008, 10 pages.
Non-Final Office Action dated Nov. 15, 2010, for U.S. Appl. No. 12/055,213, filed Mar. 25, 2008, 18 pages.
Non-Final Office Action dated Feb. 17, 2011, for U.S. Appl. No. 12/212,511, filed Sep. 17, 2008, 14 pages.
Non-Final Office Action dated Apr. 28, 2011, for U.S. Appl. No. 12/055,213, filed Mar. 25, 2008, 20 pages.
Non-Final Office Action dated Oct. 27, 2011, for U.S. Appl. No. 12/363,359, filed Jan. 30, 2009, 11 pages.
Non-Final Office Action dated Nov. 9, 2011, for U.S. Appl. No. 12/363,381, filed Jan. 30, 2009, 10 pages.
Non-Final Office Action dated Dec. 22, 2011, for U.S. Appl. No. 13/033,532, filed Feb. 23, 2011, 8 pages.
Non-Final Office Action dated Mar. 7, 2012, for U.S. Appl. No. 12/124,023, filed May 20, 2008, 13 pages.
Non-Final Office Action dated Apr. 2, 2012, for U.S. Appl. No. 12/212,511, filed Sep. 17, 2008, 5 pages.
Non-Final Office Action dated Sep. 18, 2013, for U.S. Appl. No. 12/055,213, filed Mar. 25, 2008, 15 pages.
Non-Final Office Action dated May 31, 2013, for U.S. Appl. No. 12/124,023, filed May 20, 2008, 14 pages.
Non-Final Office Action dated Apr. 2, 2014, for U.S. Appl. No. 13/033,532, filed Feb. 23, 2011, 8 pages.
Non-Final Office Action dated Oct. 28, 2015, for U.S. Appl. No. 13/033,532, filed Feb. 23, 2011, 9 pages.
Non-Final Office Action dated Jun. 17, 2014, for U.S. Appl. No. 12/363,359, filed Jan. 30, 2009, 7 pages.
Non-Final Office Action dated Sep. 10, 2015, for U.S. Appl. No. 12/363,359, filed Jan. 30, 2009, 12 pages.
Non-Final Office Action dated Nov. 10, 2014, for U.S. Appl. No. 12/752,873, filed Apr. 1, 2010, 10 pages.
Non-Final Office Action dated May 4, 2015, for U.S. Appl. No. 12/124,023, filed May 20, 2008, 8 pages.
Non-Final Office Action dated May 3, 2013 for U.S. Appl. No. 13/086,390, filed Apr. 13, 2011, 10 pages.

(56) References Cited

OTHER PUBLICATIONS

Non-Final Office Action dated Jan. 15, 2015, for U.S. Appl. No. 13/086,389, filed Apr. 13, 2011, 16 pages.
Non-Final Office Action dated Dec. 2, 2015, for U.S. Appl. No. 14/309,835, filed Jun. 19, 2014, 8 pages.
Notice of Allowance dated Mar. 20, 2014 for U.S. Appl. No. 13/086,390, filed Apr. 13, 2011, 8 pages.
Notice of Allowance dated Sep. 17, 2010, for U.S. Appl. No. 10/963,371, filed Oct. 11, 2004, 7 pages.
Notice of Allowance dated Sep. 17, 2010, for U.S. Appl. No. 11/600,671, filed Nov. 15, 2006, 7 pages.
Notice of Allowance dated Nov. 24, 2010, for U.S. Appl. No. 11/400,714, filed Apr. 7, 2006, 8 pages.
Notice of Allowance dated Feb. 22, 2013, for U.S. Appl. No. 12/212,511, filed Sep. 17, 2008, 8 pages.
Notice of Allowance dated Mar. 18, 2013, for U.S. Appl. No. 12/212,511, filed Sep. 17, 2008, 6 pages.
Notice of Allowance dated Mar. 4, 2014, for U.S. Appl. No. 12/055,213, filed Mar. 25, 2008, 9 pages.
Notice of Allowance dated Apr. 1, 2014, for U.S. Appl. No. 12/363,381, filed Jan. 30, 2009, 9 pages.
Notice of Allowance dated Dec. 29, 2014, for U.S. Appl. No. 12/363,381, filed Jan. 30, 2009, 9 pages.
Notice of Allowance dated Apr. 3, 2014, for U.S. Appl. No. 12/037,802, filed Feb. 26, 2008, 8 pages.
Notice of Allowance dated Jul. 22, 2015, for U.S. Appl. No. 12/752,873, filed Apr. 1, 2010, 8 pages.
Notice of Allowance dated Oct. 21, 2015, for U.S. Appl. No. 12/124,023, filed May 20, 2008, 9 pages.
Odell, J.A. et al. (1996). "Thorascopic Obliteration of the Left Atrial Appendage: Potential for Stroke Reduction?" *Ann. Thorac. Surg.* 61:565-569.
O'Donnell, M. et al. (2005). "Emerging Therapies for Stroke Prevention in Atrial Fibrillation," *European Heart Journal* 7(Supplement C):C19-C27.
Omran, H. et al. (1997). "Left Atrial Appendage Function in Patients with Atrial Flutter," *Heart* 78:250-254.
Onalan, O. et al. (2005). "Nonpharmacologic Stroke Prevention in Atrial Fibrillation," *Expert Rev. Cardiovasc. Ther.* 3(4):619-633.
Onalan, O. et al. (2007). "Left Atrial Appendage Exclusion for Stroke Prevention in Patients With Nonrheumatic Atrial Fibrillation," *Stroke* 38(part 2):624-630.
Ostermayer, S. et al. (2003). "Percutaneous Closure of the Left Atrial Appendage," *Journal of Interventional Cardiology* 16(6):553-556.
Ota, T. et al. (2006). "Epicardial Atrial Ablation Using a Novel Articulated Robotic Medical Probe Via a Percutaneous Subxiphoid Approach," *National Institute of Health* 1(6):335-340.
Ota, T. et al. (Oct. 2007). "Impact of Beating Heart left Atrial Ablation on Left-sided Heart Mechanics," *The Journal of Thoracic and Cardiovascular Surgery* 134(4):982-988.
Pennec, P-Y. et al. (2003). "Assessment of Different Procedures for Surgical Left Atrial Appendage Exclusion," *The Annals of Thoracic Surgery* 76:2167-2168.
Perk, G. et al. (Aug. 2009). "Use of Real Time Three-Dimensional Transesophageal Echocardiography in Intracardiac Catheter Based Interventions," *J. Am Soc Echocardiogr* 22(8):865-882.
Pollick C. (Feb. 2000). "Left Atrial Appendage Myopathy," *Chest* 117(2):297-308.
Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.
Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.
Robicsek, F. (1987). "Closed-Chest Decannulation of Transthoracically Inserted Aortic Balloon Catheter without Grafting," *Journal of Cardiac Surgery* 2(2):327-329.
Ross, J. Jr. et al. (Jun. 3, 2008). "Transseptal Left Heart Catheterization: A 50-Year Odyssey," *Journal of the American College of Cardiology* 51(22):2107-2115.
Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.
Ruchat, P. et al. (2002). "Off-pump Epicardial Compartmentalization for Ablation of Atrial Fibrillation," *Interactive Cardio Vascular and Thoracic Surgery* 1:55-57.
Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.
Sapp, J. et al. (Dec. 2001). "Electrophysiology and Anatomic Characterization of an Epicardial Accessory Pathway," *Journal of Cardiovascular Electrophysiology* 12(12):1411-1414.
Scharf, C. et al. (2005). "Catheter Ablation for Atrial Fibrillation: Pathophysiology, Techniques, Results and Current Indications," *Continuous Medical Education* 8:53-61.
Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.
Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.
Schneider, B. et al. (2005, e-pub. Aug. 22, 2005). "Surgical Closure of the Left Atrial Appendage—A Beneficial Procedure?" *Cardiology* 104:127-132.
Schweikert, R.A. et al. (Sep. 16, 2003). "Percutaneous Pericardial Instrumentation for Endo-Epicardial Mapping of Previously Failed Ablation," *Circulation* 108:1329-1335.
Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.
Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.
Sengupta, P.P. et al. (2005). "Transoesophageal Echocardiography," *Heart* 91:541-547.
Sharada, K. et al. (2005). "Non-Surgical Transpericardial Catheter Ablation of Post-Infarction Ventricular Tachycardia," *Indian Heart J* 57:58-61.
Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.
Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.
Smith, P.W. et al. (Nov. 1956). "Diagnosis of Mitral Regurgitation by Cardioangiography," *Circulation* 14:847-853.
Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.
Sosa, E. et al. (1996). "A New Technique to Perform Epicardial Mapping in the EP Laboratory," *J. Cardiovasc. Electrophysiol.* 7(6):531-536.
Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.
Sosa, E. et al. (Dec. 14, 1999). "Different Ways of Approaching the Normal Pericardial Space," *Circulation* 100(24):e115-e116.
Sosa, E. et al. (Jul. 15, 2002). "Gaining Access to the Pericardial Space," *The American Journal of Cardiology* 90:203-204.
Sosa, E. et al. (Apr. 2005). "Epicardial Mapping and Ablation Techniques to Control Centricular Tachycardia," *Journal of Cardiovasc. Electrphsiol.* 16(4):449-452.

(56) References Cited

OTHER PUBLICATIONS

Sparks, P.B. et al. (2001). "Is Atrial Flutter a Risk Factor for Stroke?" *Journal of the American College of Cardiology* 38(3):785-788.
Spodick, D.H. (Nov. 1970). "Medical History of the Pericardium," *The American Journal of Cardiology* 26:447-454.
Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.
Stewart, S. (1974). "Placement of the Sutureless Epicardial Pacemaker Lead by the Subxiphoid Approach," *Ann. of Thoracic Surg.* 18(3):308-313.
Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.
Stokes, K. (Jun. 1990). "Implantable Pacing Lead Technology," *IEEE Engineering in Medicine and Biology* pp. 43-49.
Stöllberger, C. et al. (2000). "Is the Left Atrial Appendage Our Most Lethal Attachment?" *European Journal of Cardio-Thoracic Surgery* 18:625-626.
Stöllberger, C. et al. (Dec. 2003). "Elimination of the Left Atrial Appendage to Prevent Stroke or Embolism?: Anatomic, Physiologic, and Pathophysiologic Considerations," 124(6):2356-2362.
Stöllberger, C. et al. (2006). "Stroke Prevention by Means of Epicardial Occlusion of the Left Atrial Appendage," *Journal of Thoracic and Cardiovascular Surgery* 132(1):207-208.
Stöllberger, C. et al. (2007). "Arguments Against Left Atrial Appendage Occlusion for Stroke Prevention," *Stroke* 38:e77.
Stöllberger, C. et al. (2007). "Leave the Left Atrial Appendage Untouched for Stroke Prevention!" *Journal of Thoracic and Cardiovascular Surgery* 134(2):549-550.
Su, P. et al. (Sep. 2008, e-pub. May 8, 2007). "Occluding the Left Atrial Appendage: Anatomical Considerations," *Heart* 94(9):1166-1170.
Subramanian, V.A. (Jun. 1997). "Less Invasive Arterial CABG on a Beating Heart," *Ann. Thorac. Surg.* 63(6 Suppl.):S68-S71.
Subramanian, V.A. et al. (Dec. 1997). "Minimally Invasive Direct Coronary Artery Bypass Grafting: Two-Year Clinical Experience," *Ann. Thorac. Surg.* 64(6):1648-1653, Abstract Only.
Suehiro, S. et al. (1996). "Echocardiography-Guided Pericardiocentesis With a Needle Attached to a Probe," *Ann. Thoracic Surg.* 61:741-742.
Sun, F. et al. (Feb. 2006). "Subxiphoid Access to Normal Pericardium with Micropuncture Set: Technical Feasibility Study in Pigs," *Radiology* 238(2):719-724.
Szili-Torok, T. et al. (2001). "Transseptal Left heart Catheterisation Guided by Intracardiac Echocardiography," *Heart* 86:e11-e15.
Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.
Tomar, M. et al. (Jul.-Aug. 2006). "Transcatheter Closure of Fossa Ovalis Atrial Septal Defect: A Single Institutional Experience," *Indian Heart Journal* 58(4):325-329.
Troughton, R.W. et al. (Feb. 28, 2004). "Pericarditis," *The Lancet* 363:717-727.
Ulicny K.S. et al. (Jun. 1992). "Conjoined Subrectus Pocket for Permanent Pacemaker Placement in the Neonate," *Ann Thorac Surg.* 53(6):1130-1131, Abstract Only.
Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.
Von Korn, H. et al. (2006). "Simultaneous Combined Interventional Percutaneous Left Atrial Auricle and Atrial Septal Defect Closure," *Heart* 92:1462.
Wang, T.J. et al. (Aug. 27, 2003). "A Risk Score for Predicting Stroke or Death in Individuals With New-Onset Atrial Fibrillation in the Community," *American Medical Association* 290(8):1049-1056.
Watkins, L. et al. (Nov. 1982). "Implantation of the Automatic Defibrillator: The Subxiphoid Approach," *Ann. of Thoracic Surg.* 34(5):515-520.
W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.
Wolber, T. et al. (Jan. 2007). "Potential Interference of Small Neodymium Magnets with Cardiac pacemakers and Implantable Cardioverter-defibrillators," *Heart Rhythm* 4(1):1-4.
Wolf, P.A. et al. (Oct. 1978). "Epidemiologic Assessment of Chronic Atrial Fibrillation and Risk of Stroke: The Fiamingham Study," *Neurology* 28:973-977.
Wolf, P.A. et al. (Aug. 1991). "Atrial Fibrillation as an Independent Risk Factor for Stroke: The Framingham Study," *Stroke* 22(8):983-988.
Wolf, P.A. et al. (Feb. 9, 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.
Wood, M.A. (Jan. 2006). "Percutaneous Pericardial Instrumentation in the Electrophysiology Laboratory: A Case of Need," *Heart Rhythm* 3(1):11-12.
Written Opinion of the International Searching Authority dated Jul. 13, 2011, for PCT Patent Application No. PCT/US11/00676, filed on Apr. 13, 2011, 6 pages.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'left Atrial Appendage Amputation, Ligation, or Occlusion in Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.
U.S. Appl. No. 14/928,836, filed Oct. 30, 2015, by Fung et al.
Non-Final Office Action dated Jan. 12, 2018, for U.S. Appl. No. 14/928,836, filed Oct. 30, 2015, 12 pages.
Non-Final Office Action dated Jan. 26, 2018, for U.S. Appl. No. 14/625,540, filed Feb. 18, 2015, 16 pages.

* cited by examiner

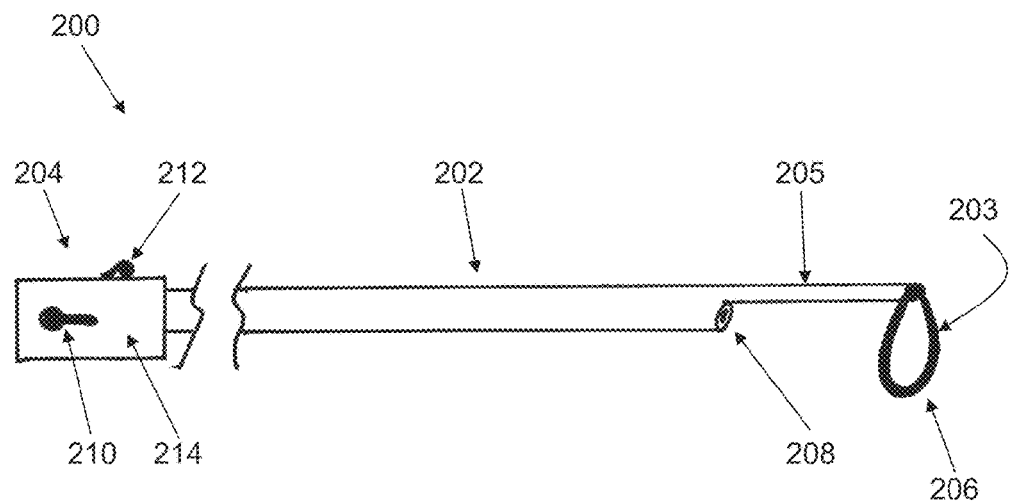
FIG. 2
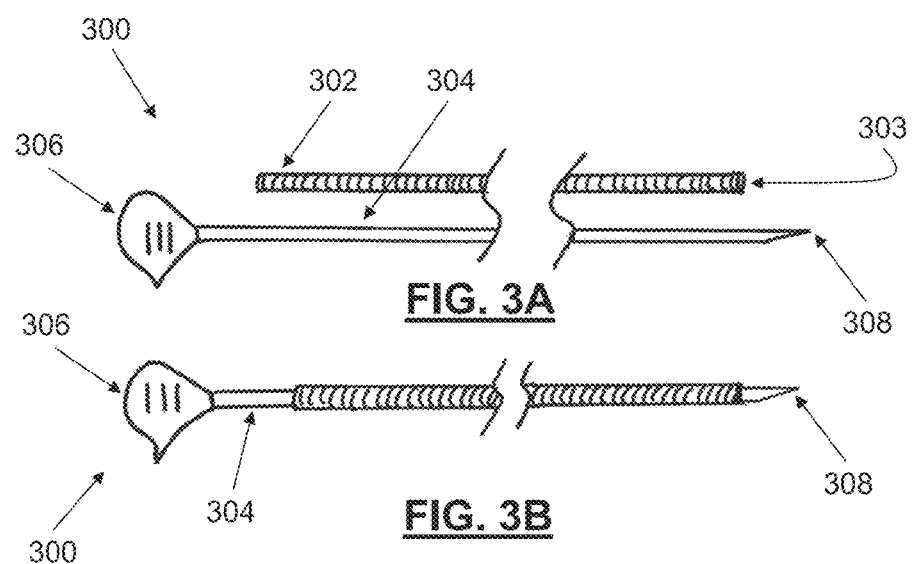
FIG. 3A
FIG. 3B

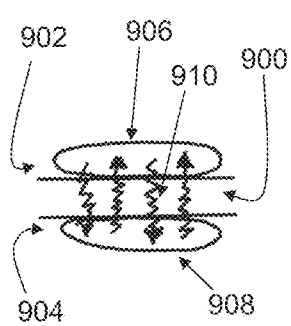 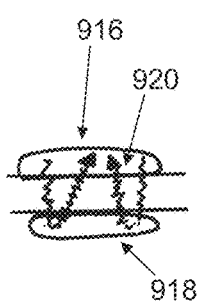 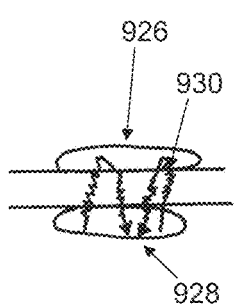 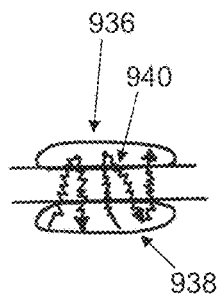
FIG. 9A  FIG. 9B  FIG. 9C  FIG. 9D
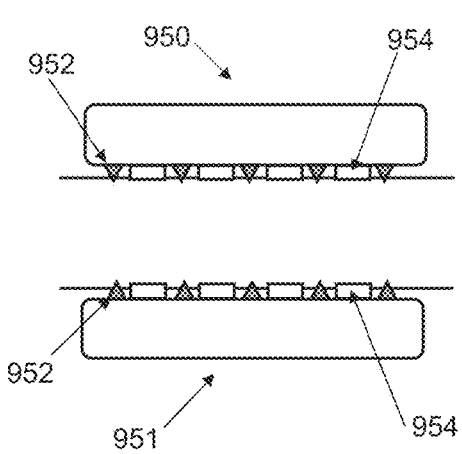 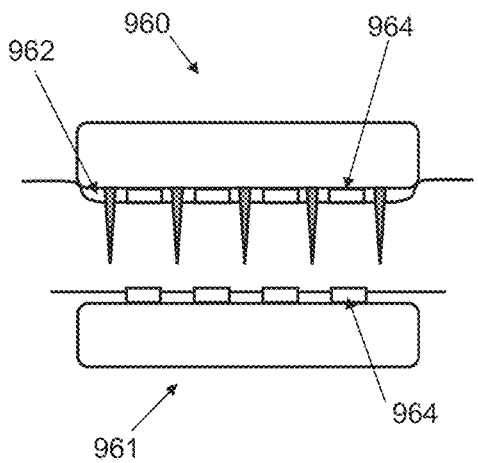
FIG. 9E  FIG. 9F

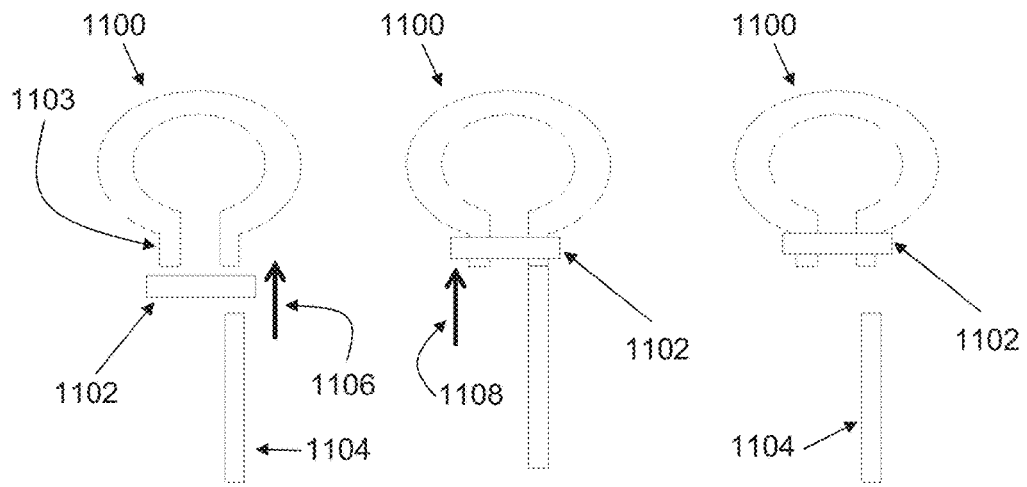
FIG. 11A   FIG. 11B   FIG. 11C
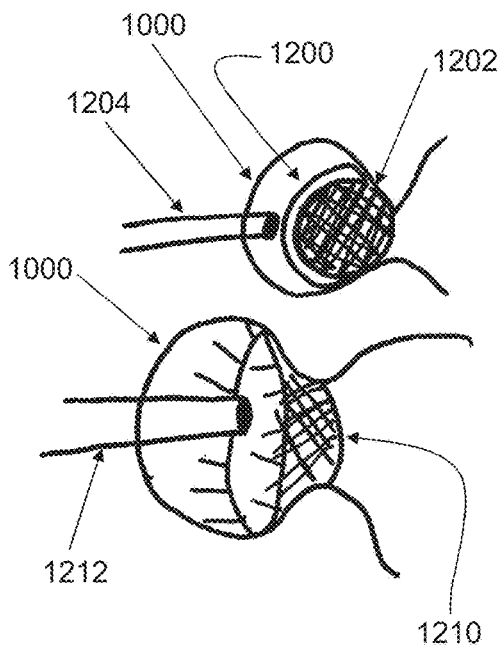
FIG. 12A
FIG. 12B

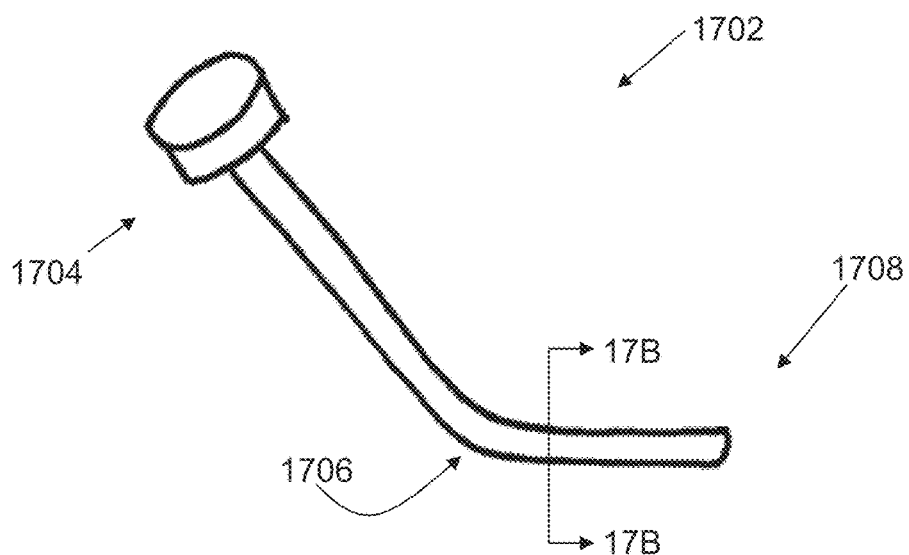
FIG. 17A
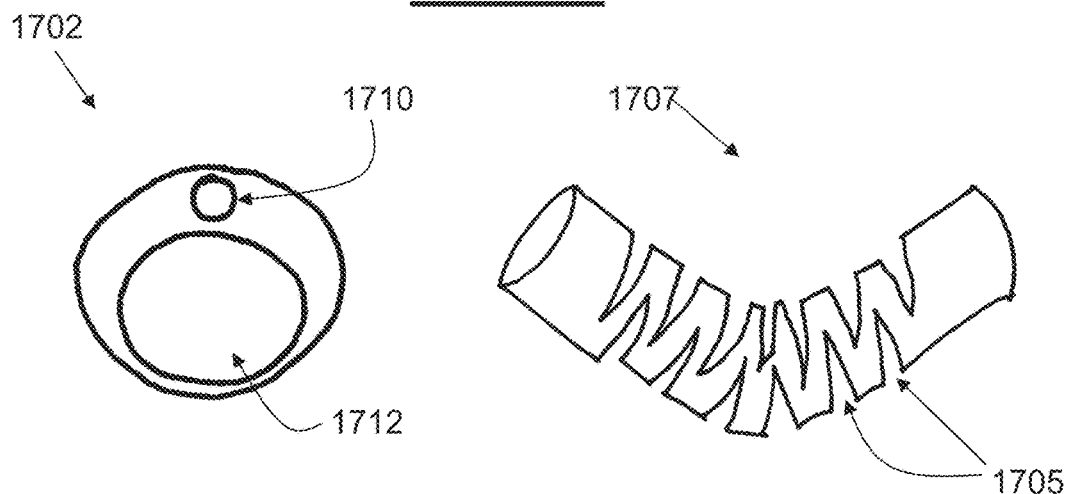
FIG. 17B  FIG. 17C

METHODS AND DEVICES FOR TREATING ATRIAL FIBRILLATION

CROSS-REFERENCE TO RELATED APPLICATIONS

This patent application is a continuation of U.S. patent application Ser. No. 13/086,389, filed Apr. 13, 2011, which claims priority under 35 U.S.C. § 119(e) to U.S. Provisional Patent Application No. 61/323,796, filed Apr. 13, 2010, U.S. Provisional Patent Application No. 61/323,801, filed Apr. 13, 2010, and U.S. Provisional Patent Application No. 61/323,816, filed Apr. 13, 2010, the disclosures of each of which are hereby incorporated by reference in their entirety.

BACKGROUND

It is well documented that atrial fibrillation, either alone or as a consequence of other cardiac disease, continues to persist as the most common cardiac arrhythmia. Atrial fibrillation may be treated using several methods, including administering anti-arrhythmic medications, and chemical and/or electrical cardioversion. Ablation of cardiac tissue using surgical techniques have also been developed for atrial fibrillation, such as procedures for atrial isolation and ablation of macroreentrant circuits in the atria. For example, the MAZE III procedure creates an electrical "maze" of non-conductive tissue in the atrium that acts to prevent the ability of the atria to fibrillate by creating incisions in certain regions of atrial tissue. In some cases, the MAZE III procedure may include the electrical isolation of the pulmonary veins. While the MAZE III procedure has shown some efficacy in treating medically refractory atrial fibrillation, additional devices and methods of treatment are desirable, especially if they provide advantages over existing techniques.

BRIEF SUMMARY

Described here are devices, systems, and methods for affecting tissue within a body to form a lesion. Some systems may comprise devices having tissue-affecting elements that are configured to be positioned on opposite sides of a tissue and operated simultaneously to form a lesion in the tissue between them. Some systems may also comprise devices that guide the advancement of the tissue-affecting elements to a target tissue region, devices that locate and secure tissue, devices that provide access to the target tissue, and/or devices that may help position the tissue-affecting elements on one or more surfaces of the target tissue. The methods described here may utilize one or more of these devices, and generally comprise advancing a first tissue-affecting device to a first surface of a target tissue, advancing a second tissue-affecting device to a second surface of the target tissue, and positioning the first and second devices so that a lesion may be formed in the tissue between them. In some variations, the devices, systems, and methods described here may be used to treat atrial fibrillation by ablating fibrillating tissue from an endocardial surface and an epicardial surface of an atrium of a heart. Methods of closing, occluding, and/or removing a portion of the target tissue (e.g., the left atrial appendage) are also described.

One variation of a system for affecting tissue within a body may comprise a first device and a second corresponding device. The first and second devices may each comprise an elongate member and one or more tissue-affecting elements. The one or more tissue-affecting elements of the second device may correspond to the tissue-affecting elements of the first device. In some variations, the first device may be configured to be placed on a first surface of a target tissue, and the second device may be configured to be placed on a second surface of the target tissue, where the second surface is opposite the first surface. The first and second devices may be configured to operate the tissue-affecting elements simultaneously to form a lesion in the target tissue at least partially therebetween.

Some variations of the first and second devices may comprise one or more magnetic components. Optionally, the first and second devices may also comprise a longitudinal lumen therethrough. The first and second devices may also comprise one or more temperature sensors. In certain variations, the first and second devices may have a first delivery configuration and a second deployed configuration, where the devices are compressed in the delivery configuration and expanded in the deployed configuration.

The first and second devices may each comprise one or more pre-shaped curves in the second deployed configuration. In some variations, the pre-shaped curves may have varying radii of curvature, and/or may be spiral or funnel shaped. In some devices, the deployed configuration may comprise one or more curves in one or more planes, and may comprise a ring-structure coupled to an expandable net.

The tissue-affecting elements of the devices may affect tissue to form a lesion using any suitable mechanism. For example, the tissue-affecting elements may ablate tissue using cryogenic substances, high intensity focused ultrasound (HIFU), radiofrequency (RF) energy, lasers, heat, microwaves, and the like. Some tissue-affecting elements may ablate tissue using a combination of different mechanisms, as suitable for the target tissue.

Methods of affecting tissue in a body are also described. One variation of a method comprises advancing and positioning a first tissue-affecting device to a first surface of a target tissue, advancing and positioning a second tissue-affecting device to a second surface of a target tissue, where the second surface is opposite the first surface, positioning the first and second tissue-affecting devices so that ablation energy may pass between them, and operating both devices simultaneously to form a lesion in the target tissue. In some variations, advancing the first device may comprise inserting a curved sheath at a location beneath a sternum and advancing the first device through the sheath. Optionally, the method may comprise withdrawing the first and second tissue-affecting devices after the lesion is formed, as well as verifying and assessing the lesion using fluoroscopic, electrical impedance, and thermal imaging techniques. In some variations of the method, the tissue-affecting devices may comprise magnetic components. Tissue-affecting devices may apply a variety of ablation energies, for example, cryogenic, high intensity focused ultrasound, laser energy, radiofrequency energy, heat energy and/or microwave energy. These methods may be used to ablate tissue of the left atrium as part of a procedure to treat atrial fibrillation, but may also be used to target gastrointestinal tissue, as well as cancerous cell masses.

Methods of forming a lesion in the tissue of a left atrium are also described here. One variation of a method may comprise advancing and positioning a first tissue-affecting device in the left atrium through a puncture or access site in a left atrial appendage, advancing a second tissue-affecting device to an external wall of the left atrium, where the second device is positioned opposite to the first device, operating both devices simultaneously to form a lesion in the atrial wall between them, and isolating the left atrial appendage. Optionally, the method may also comprise positioning the first and second devices with respect to each other using one or more magnetic components, and verifying and assessing the lesion using various imaging techniques (e.g. fluoroscopic, electrical impedance, and thermal imaging techniques). In some variations, the first tissue-affecting device may be advanced over a first guide (e.g., guide wire) into the left atrium to circumscribe the base of a pulmonary vein, and the second tissue-affecting device may be advanced over a second guide (e.g., guide wire) to circumscribe the trunk of the pulmonary vein on the external atrial wall. Additionally or alternatively, the first guide wire and the first tissue-affecting device may be advanced into the left atrium to circumscribe the bases of two or more pulmonary veins, while the second guide wire and the second tissue-affecting device may be advanced over the external atrial wall to circumscribe the trunks of two or more pulmonary veins. In some variations, isolating the left atrial appendage may comprise positioning an occlusion device comprising a rounded disc with one or more grooves circumscribing the outer perimeter of the disc, wherein the disc is sized and shaped to be constrained in an ostium or base of the left atrial appendage.

Also described here are kits for affecting tissue within a body. One variation of a kit may comprise a first device with one or more tissue-affecting elements and a longitudinal lumen therethrough, where the first device has a first compressed configuration and a second expanded configuration, a second device with one or more tissue-affecting elements and a longitudinal lumen therethrough, where the first and second devices are configured to operate simultaneously to form a lesion that spans at least a portion of tissue between them. In some variations, the kit optionally comprises first and second devices as described above, where the first and second devices also comprise one or more magnetic components and/or one or more temperature sensors. In certain variations, the kit may also comprise a closure member with an elongate body and a distal snare, where the elongate body may comprise a longitudinal lumen therethrough, a piercing member that is configured to be advanced through the lumen of the elongate body, a first and second cannula, and a first and second guide wire.

BRIEF DESCRIPTION OF THE DRAWINGS

FIG. 2 depicts one variation of a closure device.

FIG. 3A depicts an exploded view of one variation of an access device. FIG. 3B depicts one variation of an assembled access device.

FIGS. 9A-9D depict ablation patterns that may be formed by endocardial and epicardial ablation of atrial wall tissue. FIGS. 9E-9G depict variations of epicardial and endocardial ablation arrays that comprise temperature sensor in various configurations.

FIG. 10A schematically illustrates potential access sites to the pericardial space. FIGS. 10R-10S schematically illustrate the use of an occlusion device to occlude and isolate the left atrial appendage.

FIGS. 11A-11C depict one variation of a clip that may be used to secure the base or ostium of an atrial appendage.

FIGS. 12A and 12B depict various mechanisms by which an atrial appendage may be occluded.

FIG. 17A depicts one variation of an access device. FIG. 17B depicts a cross-sectional view of the access device of FIG. 17A taken along the lines 17B-17B. FIG. 17C depicts one variation of a curved region of the device of FIG. 17A with a plurality of slots.

DETAILED DESCRIPTION

The system and methods described herein may be used to affect any portion of tissue within a body to form a lesion, and/or otherwise electrically isolate a portion of tissue. For illustrative purposes, these devices and methods are described in the context of lesion formation in the tissue of the left atrium for the treatment of atrial fibrillation, and may include the closure of the left atrial appendage. For example, methods for affecting tissue to treat atrial fibrillation may comprise accessing the pericardial space of the heart, creating an access site through the left atrial appendage (LAA), advancing a tissue-affecting device intravascularly and/or through the LAA to contact an endocardial surface of the left atrium, advancing another tissue-affecting device via the pericardial space to contact an epicardial surface of the heart, and affecting tissue from either or both the endocardial and epicardial surfaces. In some variations, a LAA access/exclusion device may be used to stabilize the LAA for the advancement of devices therethrough, as well maintain hemostasis by closing and/or opening the LAA during and/or at the conclusion of the procedure. While the systems and methods disclosed here are described in the context of affecting cardiac tissue, it should be understood that these devices and methods may be used to affect a variety of tissues, such as the skin, heart, liver, etc., as well as to treat a variety of conditions, including various cardiac deficiencies, tumors, gastrointestinal deficiencies, etc.

I. Anatomy

Figure 1:
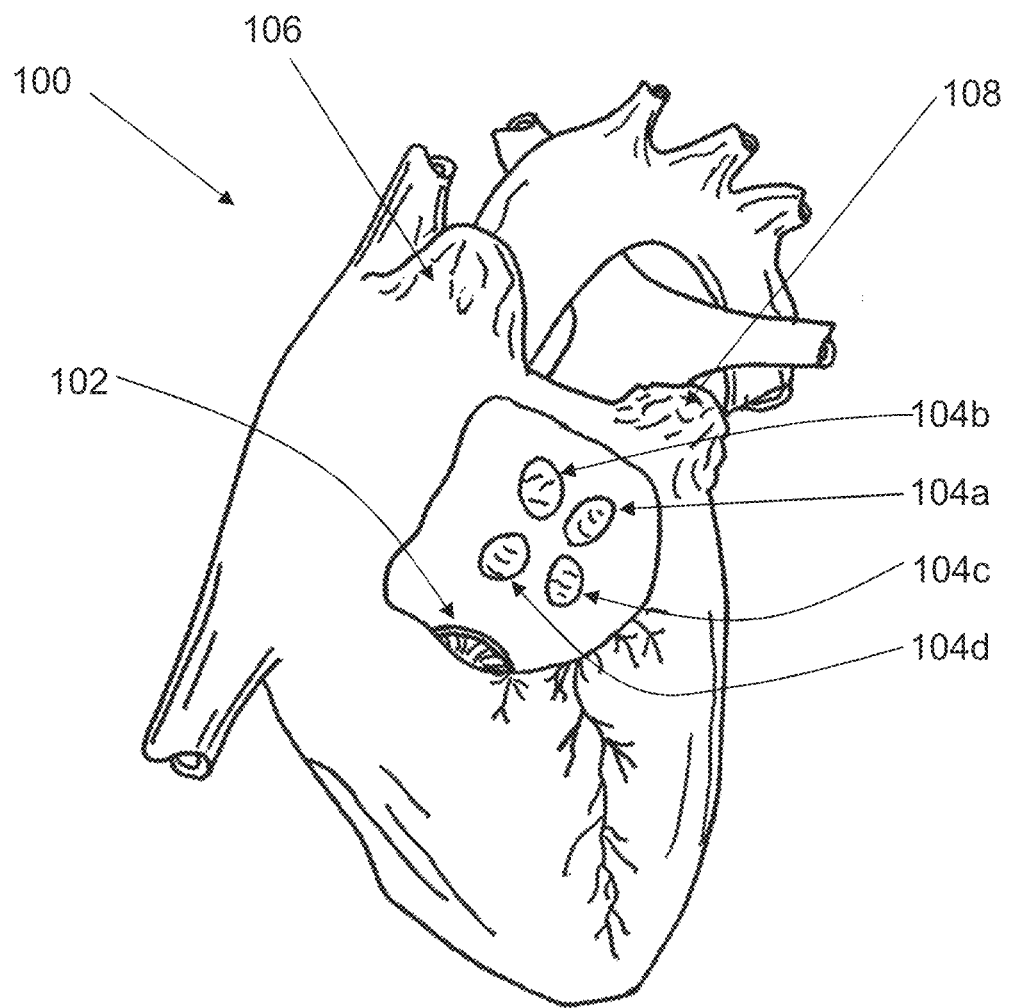
FIG. 1 depicts a heart with a partial cutaway in the left atrium.

FIG. 1 depicts a heart (100), with the cavity of the left atrium partially cut away to reveal a portion of the mitral valve (102) and pulmonary veins (104a), (104b), (104c), (104d). Both the right atrial appendage (106) and the left atrial appendage (108) are shown, located on the superior portion of the heart (100). The heart (100) is enclosed by a pericardium (not shown), which is filled with a fluid that may separate it from the heart. The fluid-filled space between the pericardium and the heart is the pericardial space. In a heart affected by atrial fibrillation, tissues associated with one or more of these anatomical structures may pulsate irregularly or asynchronously, and may cause the atrium to contract quickly and/or irregularly. Procedures for the treatment of atrial fibrillation may comprise the electrical isolation of arrhythmic cardiac tissue from other tissue regions. In some variations, devices and methods for treating atrial fibrillation may be directed towards the formation of lesions in the right atrium (e.g. in the proximity of the tricuspid valve annulus, the anterior limbus of the fossa ovalis, and/or the right atrial appendage), and/or lesions in the left atrium (e.g. in proximity of the pulmonary veins and/or LAA). For example, one variation of a method for treating atrial fibrillation in the left atrium may comprise the electrical isolation of tissue(s) at or around or within each of the pulmonary veins, and may optionally include the closure, occlusion, and/or removal of the left atrial appendage. While the devices and methods described below may be used to access, affect, and electrically isolate tissue in the left atrium, similar devices and methods may be used to treat any suitable portion(s) of the heart, e.g., the right atrium, right ventricle, left ventricle, etc.

II. Devices

Pericardial Access Device

In order to access certain portions of the heart, it may be useful to place one or guide elements in the pericardial space around the heart. Various devices may be used to provide access to the pericardial space for the placement of a guide element into the pericardial space for the advancement of subsequent devices to the heart. Some pericardial access devices may be configured to provide an access pathway from an initial access site (e.g., a sub-thoracic region, an intercostal region, etc.). For example, a pericardial access device may comprise a sheath with one or more curves, and one or more needles, guide elements, tissue-piercing elements, etc. to create a pathway through the pericardium to access the pericardial space. In some variations, the one or more needles, guide elements, tissue-piercing elements, etc. may be sized and shaped to correspond with the one or more curves in the sheath. One example of a sheath with one or more curves is shown in FIGS. 17A and 17B. As shown there, the sheath (1702) may have a curved region (1706) between the proximal portion (1704) to the distal portion (1708). The proximal portion (1704) may be connected to a proximal sheath actuator. A sheath actuator may be used to advance the sheath, e.g., along a longitudinal axis, to navigate the distal portion of the sheath, and/or may be configured to cause the curved region (1706) to bend. A cross-section of the sheath (1702) is depicted in FIG. 17B. The sheath (1702) may have one or more longitudinal lumens therethrough, for example, a wire lumen (1710) and an access device lumen (1712). Other variations of a curved or bendable sheath may have any desired number of lumens therethrough, e.g. 2, 3, 5, 8, etc. The wire lumen (1710) may be sized and shaped for passing a wire therethrough. The access lumen (1712) may be sized and shaped to pass a pericardial access device therethrough, for example, any of the access devices described above. In some variations, sheaths may have additional lumens for inserting other devices therethrough, and/or as necessary for accommodating mechanisms that may be used to control the flexion of the curved region (1706).

The curved region (1706) may have one or more pre-shaped curves, and/or may be flexible or bendable using a suitable actuating mechanism controlled by the sheath actuator at the proximal portion (1704). The curved region (1706) may serve to generally orient the sheath toward the heart upon insertion at an initial access point beneath the sternum, and/or may have a particular radius of curvature to help guide the sheath under the rib cage to the heart. In some variations, the curvature of the curved region (1706) may be locked or fixed, e.g., the curved region (1706) is first actuated to attain a desired degree of curvature, then locked to retain that desired curvature. Suitable locking mechanisms may include, for example, maintaining the tension of a wire that may be inserted through the wire lumen (1710), or immobilizing the hinge mechanisms to a desired configuration. A flexible or soft curved region may be locked into position by fixing the configuration (e.g., curvature, tension, etc.) of the wire within the wire lumen (1710). Some variations of a sheath may have a pre-shaped curve, where the radius of curvature is determined at the time of manufacture, and remains unchanged as the sheath is used. The radius of curvature of the curved region may be adjusted for sheaths that are inserted at different initial access points. For example, the radius of curvature of a curved region of a sheath to be inserted at an intercostal access site may be different from the radius of curvature of a curved region of a sheath to be inserted at a sub-thoracic access site.

The curved region (1706) may be made of a flexible or bendable material, or may be made of a substantially rigid material arranged in articulating segments that allow for the curved region (1706) to bend when actuated. The curved region (1706) may be integrally formed with the body of the sheath (1702), or may be separately formed and attached to the sheath (1702). For example, the curved region (1706) may be made of polymeric tubing and/or materials such as Pebax®, nylon, fluoropolymers (e.g., PTFE, FEP), polyethelene, Teflon®, polyethylene terephthalate (PET), Tecothane®, etc. In some variations, the curved region (806) may be made of a polymeric tube with reinforced stainless steel or nitinol. Where the curved region (1706) is made of a substantially rigid material, for example, stainless steel, nickel titanium, nitinol, cobalt alloys (e.g. nickel-cobalt, cobalt-nickel-chromium-molybdenum), and/or polymers such as PEEK, polyethylene (HDPE), polyimide, etc., the curved region may be slotted or segmented to allow bending to occur. In some variations, a curved region (1707) may have one or more slots (1705), as illustrated in FIG. 17C. In other variations, the curved region (1706) may comprise a plurality of segments, where the positioning of the segments with respect to each other is controlled by a wire or pivot mandrel. The segments may be coupled together via mechanical hinges and/or living hinges. Sheaths may also comprise multiple curved regions, where each of the curved regions may have the same or different radii of curvature. For example, one curved region may be made of a material with a selected flexibility, while another curved region may be made of a material with a different flexibility. Other curved regions may be slotted or segmented, as appropriate. Different curved regions may be separated by a straight portion of the sheath, or may be contiguous. A plurality of curved regions may help to provide additional maneuverability to navigate the distal portion of the sheath to the targeted region of the heart. Adjusting the tension on a wire through the wire lumen (1710) may alter the curvature of the curved region (1706). For example, increasing the wire tension may cause bending of the curved region (1706), while decreasing the wire tension may cause straightening of the curved region (1706).

Figure 17D:
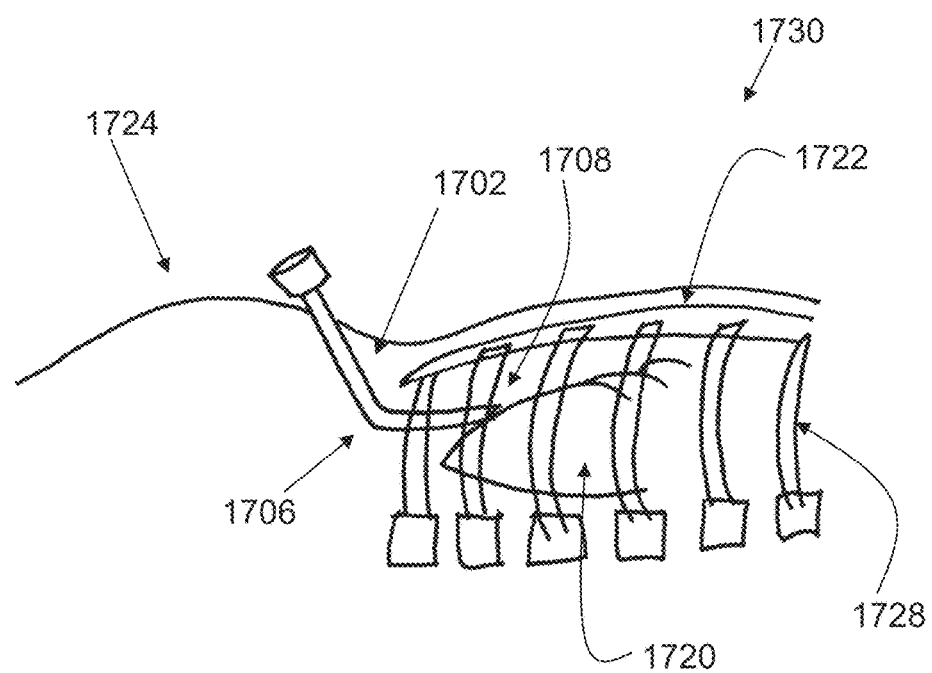
FIG. 17D depicts one example of how the access device of FIG. 17A may be used to provide an access path to the heart.

FIG. 17D depicts one variation of a method of using the sheath (1702). The sheath (1702) may be inserted into the subject (1730) at a location beneath the sternum (1722). Prior to insertion, the sheath may be substantially straight, or may be curved, as appropriate. Once the sheath (1702) has been inserted, the curved region (1706) may be adjusted in order to bring the distal portion (1708) close to the surface of the heart (1720). For example, the distal portion (1708) may be navigated underneath the ribs (1728) towards the heart (1720). Once the distal portion (1708) of the sheath (1702) is in a desired location, e.g., an anterior and/or slightly lateral side of the heart, the curved region (1706) may be locked to retain the curvature of the curved region. The location of the distal portion (1708) may be monitored using any suitable imaging modality, for example, ultrasound, fluoroscopy, and the like. In some methods, the location of the distal portion (1708) may be monitored by tactile feedback.

An articulating sheath such as is shown and described above may be useful for accessing the heart (1720) where the abdomen (1724) of the subject (1730) may limit the angle at which the sheath (1702) may be positioned. Certain subject anatomy, such as a smaller abdomen (1724) may provide a large range of maneuverability for the sheath (1702), while a larger abdomen (1724) may limit the range of maneuverability for the sheath. Providing one or more curved regions may allow the heart to be more readily accessed where subject anatomy limits the range in which the sheath may be positioned. For example, providing one or more curved regions may help to reduce the force that may be required to position the sheath (1702), and may provide additional access paths to the heart in the event the originally planned pathway becomes unavailable.

Closure Device

Some methods for treating atrial fibrillation may comprise accessing an endocardial surface of the left atrium through the LAA via the pericardial space. Methods that utilize the LAA as an entry port may also comprise closing and/or opening the LAA during the procedure (e.g., to advance devices therethrough) to maintain hemostasis. Optionally, methods may also comprise excluding the LAA at the conclusion of the procedure. Such a device may be used during the procedure to stabilize the LAA so that tissue-affecting devices may be advanced through the LAA into the left atrium, and may be used to at the conclusion of the procedure to permanently close off or otherwise occlude the LAA. One example of a device that may be capable of locating, securing, manipulating, stabilizing, closing and/or excluding the LAA is depicted in FIG. 2. Closure device (200) may comprise an elongate body (202), a handle portion (204) located at a proximal portion of the elongate body (202), an extension (205) located at a distal portion of the elongate body (202), and a distal looped closure assembly (206) distally coupled to the extension (205). While the closure device disclosed below is described in the context of locating, securing, manipulating, stabilizing and/or closing the LAA, it should be understood that the closure device may be used to act on any desirable tissue.

The elongate body (202) may have any appropriate shape, for example, the elongate body may be substantially straight (as depicted in FIG. 2), or may have one or more pre-formed curves and shapes. The elongate body (202) may have a suitable cross-sectional diameter and longitudinal length to facilitate navigating the closure device (200) through the vasculature to contact the LAA (or other target tissue). The elongate body (202) may be made of one or more flexible or rigid materials, as may be suitable for navigating towards the target tissue. In some variations, the elongate body may be steerable, and comprise steering mechanisms (such as mandrels, articulating and/or living hinges, cables, etc.) that allow a user to steer the elongate body using the handle portion (204). For example, the elongate body may be made of a single integral flexible material with one or more steering mandrels embedded in the side wall of the elongate body, such that bending the mandrel(s) would cause a corresponding deflection of the elongate body, which may help steer the elongate body towards the target tissue. Alternatively or additionally, the elongate body may be made of a plurality of segments that may be connected by articulating and/or living hinges. Each of the plurality of segments may be rigid or flexible. One or more mandrels may be coupled to each of the plurality of segments, and may be used to bend and steer the elongate body towards the target tissue. The elongate body may also comprise locking mechanisms so that after the elongate body is steered to a target location, it may be locked to retain a certain configuration to maintain contact with that target location. The elongate body (202) may comprise one or more working channels (208) that extend from the proximal portion of the elongate body (202) to the distal portion of the elongate body. A variety of devices may be inserted through the working channel in order to manipulate a portion of tissue. Alternatively or additionally, the closure device (200) may be advanced over a guide element using the working channel (208).

As depicted in FIG. 2, the distal extension (205) may extend distally beyond the distal end of the elongate body (202). This may allow for additional working space as may be suitable for accessing the LAA. For example, the distal extension (205) may extend distally beyond the distal-most portion of the working channel (208) of the elongate body. The length of the distal extension (205) may be selected such that when the base of the LAA is engaged by the distal looped closure assembly (206), the tip of the LAA may be close to (e.g., in contact with) the distal-most portion of the working channel (208). This may allow devices that are advanced through the working channel (208) to directly contact and/or manipulate the tip of the LAA once it exits the working channel.

The distal extension (205) may be integrally formed with elongate body (202), or separately formed and attached to the elongate body (e.g., by welding, melding, brazing, adhesives, etc.). The distal extension (205) may be made of rigid and/or flexible materials, and may be made of the same or different materials as the elongate body. The elongate body and/or distal extension may be made of polymeric materials such as Pebax®, polyethylene, and/or other thermoplastic materials with various durometers or densities, and/or any polymers that may be tapered or graduated for varying degrees of flexibility. Additionally or alternatively, the elongate body and/or distal extension may be made of metallic materials such as nitinol, stainless steel, etc. The looped closure assembly (206), distal extension (205), elongate body (202), and/or portions thereof may comprise visualization markers, such as fluorescent markers, echogenic markers, and/or radiopaque markers, that permit the closure device to be visualized using a variety of imaging modalities. As with the elongate body (202) described above, the distal extension (205) may also be steerable. In some variations, the distal extension (205) may be steered independently from the elongate body, while in other variations, the distal extension (205) may be steered together with the elongate body. For example, a steering mandrel that may be used to steer the elongate body may also be coupled to the distal extension so that the extension may be steered in concert with the elongate body. Alternatively, there may be a first mandrel for the steering the elongate body and a second mandrel for steering the distal extension independently from the elongate body. Optionally, the distal extension may have one or more pre-shaped curves which may help to navigate the closure device (200) to a target tissue region.

In some variations, the distal extension (205) may comprise one or more lumens that may extend from the distal-most end of the extension to the proximal portion of the closure device (e.g., to the handle portion). A lumen in the distal extension may slidably retain a portion of the looped closure assembly such that the dimensions of the loop may be adjusted. For example, the lumen of the distal extension (205) may slidably retain the looped closure assembly (206), which may comprise a distal loop (203). The distal loop (203) may comprise a snare loop and a suture loop that may be releasably coupled along the circumference of the snare loop. The distal loop (203) may be made of polymeric materials such as Pebax®, and/or metallic materials, such as nitinol, and/or any elastic, malleable, deformable, flexible material. The portion of the distal loop that extends outside of the extension, i.e., the external portion of the distal loop, may be adjustable using an actuator at the proximal handle portion. Adjusting the length of the external portion of the distal loop (203) may help to snare and/or close, or release and/or open, a LAA or any anatomical protrusion. While the distal loop (203) may have the shape of a circle, it may also have other shapes, e.g., an ellipse, oval, triangle, quadrilateral, etc. In other variations, the looped closure assembly may be configured (e.g. knotted, looped, coiled, etc.) for other functions, such as locating and securing tissue. For example, the looped closure assembly may optionally comprise tissue graspers, hooks, or other such tissue engagement components that may help secure and retain a tissue portion.

The looped closure assembly (206) may have an expanded (e.g., open) configuration, and a tightened (e.g., closed) configuration, where the circumference of the loop in the tightened configuration is smaller than in the expanded configuration. For example, a distal loop with an elliptical shape in the open configuration may have a length along the minor axis (e.g., the shortest dimension of the ellipse) from about 15 mm to about 50 mm, e.g., about 20 mm, and a length along the major axis (e.g., the longest dimension of the ellipse) from about 15 mm to about 50 mm, e.g., about 40 mm. A distal loop in the closed configuration may have a diameter equivalent to about 5 mm to about 10 mm, e.g., 6 mm. The looped closure assembly (206) may be tightened or cinched to encircle and secure the LAA, and in some variations, may be able to close the LAA after it has been secured, if desirable. Optionally, the looped closure assembly (206) may be releasably coupled to the closure device such that after the LAA is encircled and secured by the distal loop (203), a knot or locking element may be deployed to retain the tension on the distal loop, which may then be released from the closure device. For example, a looped closure assembly may have a releasable suture loop that is tightened over the LAA and then released from the closure device. The tension on the suture loop may be locked so that the looped closure assembly may be proximally withdrawn from the suture loop. Optional closure elements, such as sutures, graspers, clips, staples, and the like, may be included with the looped closure assembly to help close the LAA. For example, additional closure features, e.g., graspers or staples, may be included at the tip of distal extension (205) that may act to secure the LAA. A looped closure assembly may also comprise one or more energy sources distributed along the length of the distal loop, where the energy sources may be used to ablate tissue or induce tissue fusion. Alternatively or additionally, the looped closure assembly (206) may be actuated in conjunction with other devices advanced through the working channel (208) to secure and position the closure device with respect to the LAA.

Various types of devices may be inserted through the working channel (208) of the elongate body (202) as may be desirable. In some variations, a vacuum device may be inserted through working channel (208), while in other variations, alignment devices, guide elements, grasper devices, visualization devices, ablation devices, and/or cutting devices may be inserted through the working channel. Variations of the closure device may have a multi-lumen elongate body, where each lumen may be a working channel for one or more different devices. For example, the elongate body (202) may have multiple working channels for the insertion of different devices. Additionally or alternatively, the elongate body (202) may comprise working channels for the injection of liquid or gas fluids, as well as the application of therapeutic and/or chemical agents. The working channel (208) may have any cross-sectional shape as may be suitable for the devices to be inserted therethrough, for example, circular, rectangular, etc.

The closure device (200) may comprise mechanisms to control the bending and/or steering of the elongate body, as well as adjust the length of the distal loop that extends outside of the distal extension. For example, these functions may be controlled by levers and/or knobs at the handle portion (204). The handle portion (204) may comprise a housing (214), a loop actuator (212), and a working channel actuator (210). The housing (214) may enclose at least a portion of the actuators that control the use of the elongate body, the looped closure assembly, and the device in the working channel of the elongate body. For example, loop actuator (212) may regulate the tension on the distal loop of the looped closure assembly, and control the circumference of the external portion of the distal loop, e.g. decrease it to encircle and/or close the LAA, and increase it to release the LAA. In some variations, the loop actuator (212) may be a slider configured to adjust the circumference of the distal loop (203). In variations where the distal loop comprises a releasable suture loop, the loop actuator may also comprise a fob that initially couples the suture loop with the closure device and may be pulled to release the suture loop from the closure device. The working channel actuator (210) may comprise one or more buttons, sliders, levers, knobs, and the like that are configured regulate the operation of the device(s) in the working channel(s) of elongate body (202). For instance, the working channel actuator (210) may be a grasper actuator, and/or vacuum actuator. Optionally, handle portion (204) may also comprise one or more buttons, sliders, levers, and/or knobs that may be used to navigate the LAA access device through the vasculature to access the LAA, for example, by rotating, pulling, pushing, bending, or otherwise manipulating steering mandrels. Other features of a closure device and methods of use are described in U.S. patent application Ser. No. 12/055,213 (published as U.S. Pub. No. 2008/0243183 A1), which is hereby incorporated by reference in its entirety. Another example of a closure device and methods of use are described in U.S. patent application Ser. No. 12/752,873, entitled "Tissue Ligation Devices and Controls Therefor," filed Apr. 1, 2010, which is hereby incorporated by reference in its entirety.

LAA Access Device

As described above, a variety of devices with different functions may be inserted through the working channel(s) of the elongate body of a closure device to secure and/or otherwise manipulate a portion of tissue. In procedures where access to an internal tissue structure may be desired (e.g. accessing a lumen of a hollow organ or vessel), an access device may be inserted through the working channel of the closure device after the closure device has been advanced at or near the target tissue (e.g., by advancing the closure device over a guide element). Access devices may create a way for the internal portion of a tissue to be accessed from outside the tissue. In some variations, access devices may create an incision, puncture, and/or opening, etc., which may be dilated to allow access to devices larger than the initial opening. Optionally, some variations of an access device may also comprise a guide wire that may be advanced into the created access site. One example of such a device is shown in FIGS. 3A and 3B. FIG. 3A shows individual components of one variation of an access device that may be used to access a LAA or other tissue, and FIG. 3B shows the access device of FIG. 3A fully assembled. In this variation, LAA access device (300) comprises an access wire (302), a piercing wire (304), and an actuator portion (306). The access wire (302) may comprise a lumen (303) therethrough, where the lumen (303) may be sized and shaped for the passage of a piercing element therethrough, e.g. the piercing wire (304). The access wire (302) may be made of a metal alloy or one or more polymers that have mechanical properties suitable for threading the LAA access device (300) in the working lumen of a LAA stabilizing device and for guiding the piercing element. The access wire (302) may be made of a variety of materials, including but not limited to nitinol, stainless steel, as well as polymeric materials such as polyethylene, polypropylene and the like. The piercing wire (304) may be threaded through the lumen (303) of the access wire (302), and may comprise a piercing tip (308) at the distal portion. The piercing tip (308) may be used to create a puncture through the LAA. Optionally, the piercing wire (304) may comprise a lumen therethrough for the insertion of other devices, such as a catheter, guide wire, suture, and/or may be used for the infusion of fluids (e.g. gas or liquid fluids). In some variations, the piercing tip (308) may be a needle that is attached to the distal portion of the piercing wire (304). The piercing tip (308) may be separately or integrally formed with the piercing wire (304), and may have a lumen therethrough. The proximal portion of piercing wire (304) may be coupled with the actuator portion (306). The actuator portion (306) may be used to advance and/or withdraw and/or steer and/or rotate the piercing wire (304), and may also be used to maneuver the access wire (302) to access the LAA or other target tissue. The actuator portion (306) may be manual or mechanized, and may contain ergonomic features as appropriate, as well as electrical/mechanical interfaces to receive and execute instructions from a computing device or microcontroller. For example, the actuator portion (306) may be made of a metal alloy and/or one or more polymers that may be shaped to have an ergonomic geometry. The actuator portion (306) may be made of any materials that possess sufficient rigidity, flexibility, durability, etc., to engage and control the mechanisms driving the use of the closure device (200).

Corresponding Ablation Devices

Another example of a device that may be advanced through the working channel(s) of the elongate body of a closure device is a tissue-affecting device. Devices that affect tissue may generally comprise one or more tissue-affecting elements, arranged in various patterns. In some variations, two or more tissue-affecting devices may be positioned along a target tissue, and used to affect the tissue in a desired pattern, where the tissue-affecting elements may be operated simultaneously or sequentially. In some variations, the two or more tissue-affecting devices may be placed across each other on opposite sides of tissue such that the tissue between them is affected. One example of a tissue-affecting device is an ablation device. Ablation devices may be provided for procedures that aim to ablate a portion of tissue that is abnormal, for example, cancerous tissue, or arrhythmic cardiac tissue. While affecting tissue by ablation is described in detail here, tissue may be affected in other ways, including by excision, occlusion, manipulation and the like. As described below, an ablation device may be used to ablate fibrillating atrial tissue, which may help to prevent the conduction of the irregular or asynchronous pulses in one tissue region to another tissue region.

Figure 4:
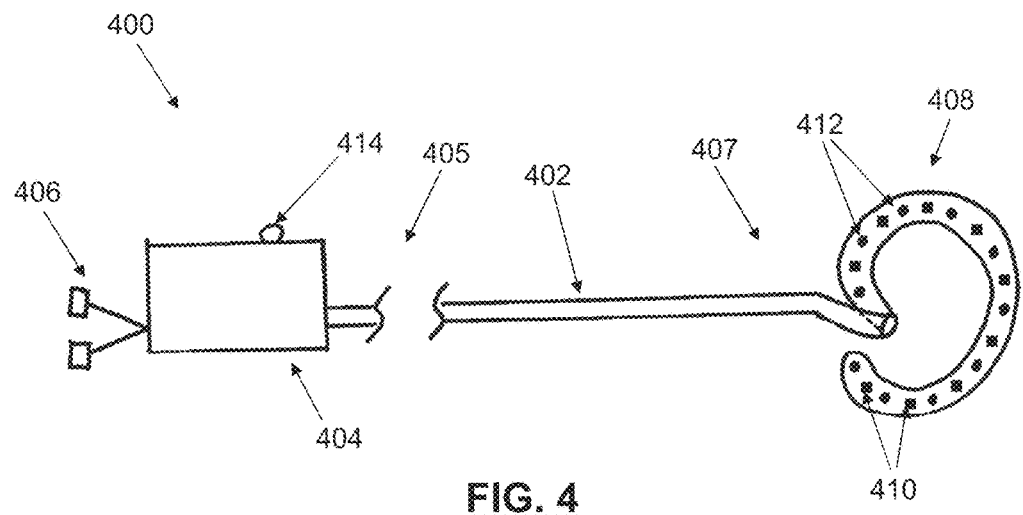
FIG. 4 depicts one variation of an endocardial ablation device.

In some variations, ablation devices may be used to create a lesion in the fibrillating atrial tissue. For the treatment of atrial fibrillation, one or more tissue-affecting devices, such as ablation devices, may be positioned on the endocardial surface and/or the epicardial surface of the left atrium. One example of an endocardial ablation device that may be inserted through a closure device is shown in FIG. 4. Endocardial ablation device (400) may comprise an elongate body (402), a handle portion (404), one or more ablation source(s) (406), and an ablation array (408). The elongate body (402) may be sized and shaped to be inserted through a working channel of a closure device, or any suitable guide cannula or sheath. The elongate body (402) may comprise one or more lumens therethrough, where the lumens may be configured to pass devices or fluids from the proximal handle portion (404) to the ablation array (408) at the elongate body distal portion. The elongate body may have any number of pre-formed curves for ease of navigation to the target tissue, and may optionally be flexible and/or steerable. While the elongate body (402) may be one continuous segment, other variations of an elongate body may be made of multiple articulating segments, and may be made of one or more flexible and/or rigid materials. In some variations, the elongate body may be steerable via a mechanism in handle portion (404), and as previously described for the closure device. In variations where the elongate body is passed through a portion of a closure device, the curvature and steerability of the elongate body (402) may correspond to the curvature and steerability of the closure device. This may help to inform a practitioner of the orientation of the endocardial ablation device with respect to the orientation of the closure device.

As shown in FIG. 4, the ablation array (408) may be located at the distal portion of elongate body (402). An ablation array may comprise one or more tissue-affecting elements that may be used for ablating and/or otherwise forming a lesion in tissue. For example, the ablation array (408) may comprise magnets (410) and ablation elements (412) that may be arranged, for example, along pre-formed curves or loops of the ablation array (408). The elongate body may also comprise magnets. The magnets may be of any suitable type. For example, the magnets may be rare-earth, electro-activated, or a multi-alloy (e.g. iron, boron, neodymium) magnets. The magnets may also have any suitable size or shape. More generally, the distal portion of an elongate body may have any open-shape or closed-shape geometry, and the magnetic and/or ablation elements may be arranged along the elongate body, ablation array, and/or on a structure at least partially enclosed within the perimeter of a shaped distal portion of the elongate body. In some variations, the ablation elements may themselves be magnetic. There may be any number of magnets (410) having any suitable configuration(s) or pattern(s), placed at any suitable location on the ablation array. For example, the magnets (410) may be arranged in a straight or curved line along the curvature of the ablation array (408), as shown in FIG. 4. Magnets may also be arranged along a length and a width of ablation array. There may be any number of ablation elements (412) as may be suitable to help ensure that sufficient ablation coverage of the target area is provided. For example, there may be 1, 2, 3, 5, 10, 12, 20, etc. ablation elements. In general, ablation elements may be utilize any mechanism and be in any form that conveys the ablation energy/medium to the target tissue. For example, cryo-ablation elements may comprise conduits that may circulate a cryogenic substance in conductive proximity to the target tissue. Ablation elements may be electrodes that ablate tissue via radiation or heat energy. Alternatively or additionally, ablation elements may be outlets or ports that infuse substances that cause necrosis or apoptosis. For example, ablation elements may ablate tissue using one or more methods, such as cryo-ablation, heat ablation, high intensity focused ultrasound (HIFU) ablation, radiofrequency (RF) ablation, laser ablation, or combinations of the listed methods and/or any method that causes necrotic or apoptotic cell and/or tissue death. Some ablation arrays may comprise two or more different types of ablation elements, e.g., 2, 3, or 4 types of ablation elements. In some variations, an ablation array may comprise both RF and cryo-ablation elements. In some variations, an ablation array may comprise RF electrodes and HIFU electrodes. In still other variations, an ablation array may comprise laser emitters and RF electrodes. In some variations, an ablation array may comprise HIFU electrodes, RF electrodes, and cryo-ablation elements. The different types of ablation elements on an ablation array may be activated simultaneously and/or sequentially in the course of ablating tissue. Alternatively or additionally, ablation elements may be sharp elements, e.g. needles, that excise, cut, or pierce tissue, or any combination of the above. For example, an endocardial ablation device may comprise electrode ablation elements and needle ablation elements.

The shape of the ablation array (408) as shown in FIG. 4 is semi-circular, which may be suitable for circumscribing and ablating around a vascular structure, such as a pulmonary vein, however, other variations of ablation arrays may have other shapes. For example, an ablation array may have a planar structure with a length and a width, with ablation elements arranged along both the length and the width. An ablation array may also be a one-dimensional array, e.g., a linear structure, where the ablation elements are arranged linearly therealong. Indeed, ablation arrays may be any shape suitable for accessing and contacting the target tissue. For example, the semi-circular shape of ablation array (408) may be suited for circumscribing vascular structures, such as veins or arteries, and may be configured to create circular ablation patterns. Ablation arrays may also have a tapered region that may be helpful in accessing and contacting in the lumen of tubular structures, e.g., the inner lumen of a vein. In some variations, an ablation array may have a narrow undeployed configuration and an expanded deployed configuration. For example, an ablation array may be constrained in a sheath for delivery, and may expand into the deployed configuration by removing the sheath. In another variation, a curved ablation array may be retained in a straight configuration by a straightening mandrel for delivery, and may be expanded into the curved deployed configuration by removing the mandrel. Other variations will be described in detail below.

The ablation array (408) may be made from a flexible or shape-memory material, such that it may be advanced to the target tissue in a substantially straight configuration, and may be deployed and contacted to tissue in a curved configuration. In some variations, the ablation array is made of a different material from the remainder of the ablation device (400), and may have different mechanical properties. For example, the proximal portion (405) of the elongate body may be made of a first material, while the distal portion (407) and/or the ablation array may be made of a second material. Examples of materials that may be suitable for the proximal portion (405) and/or the distal portion (407) of the elongate body may include metal alloys such as nickel titanium alloy, stainless steel, and/or any polymers, such as polyethylene, polyurethane, polypropylene, polytetrafluoroethylene, polyimide, etc., and/or any combinations thereof. In some variations, an ablation array may be integrally formed with the proximal portion of the ablation device, or may be attached via an articulating hinge. The ablation array may also be attached by other mechanical mechanisms, such as a living hinge, pivot joint, ball joint, etc, which may allow the ablation array to move with respect to the proximal portion of the ablation device (e.g., with two or more degrees of freedom).

The handle portion (404) located at the proximal end of elongate body may comprise actuating elements that control the movement and/or action of the elongate body and ablation array. In some variations where endocardial ablation device (400) is manually operated, the handle (400) may be ergonomic, while in other variations where the device is mechanically/electrically operated, handle (400) may comprise an interface to receive and execute instructions from a computing device. The handle portion (404) may comprise an ablation array actuator (414), which may be used to regulate application of ablation energy/substances to the ablation array to the target tissue (e.g. frequency, duty cycle, magnitude/amplitude, etc.). Additionally, the handle portion (404) may comprise an actuating mechanism that controls the movement (e.g., bending, flexing, etc.) and position of elongate body (402). The handle portion (404) may also comprise an interface to the ablation source(s) (406), and provide a conduit or conduction pathway from the ablation source(s) (406) to the ablation array. For example, the ablation source (406) may comprise a reservoir of cryogenic substances (e.g., for cryo-ablation), which may be transported through a lumen in the elongate body (402) to the ablation array. Alternatively or additionally, the ablation source (406) may comprise a source of radioactive substances (e.g., radioactive seeds or fluids), and/or a light beam source (e.g., for laser ablation), and/or an ultrasound source (e.g., for HIFU ablation), and/or a radiofrequency source, and the like, which may be delivered or transmitted from the handle portion to the ablation array. In some variations, different ablation sources may be used together in the same ablation device.

Figure 5:
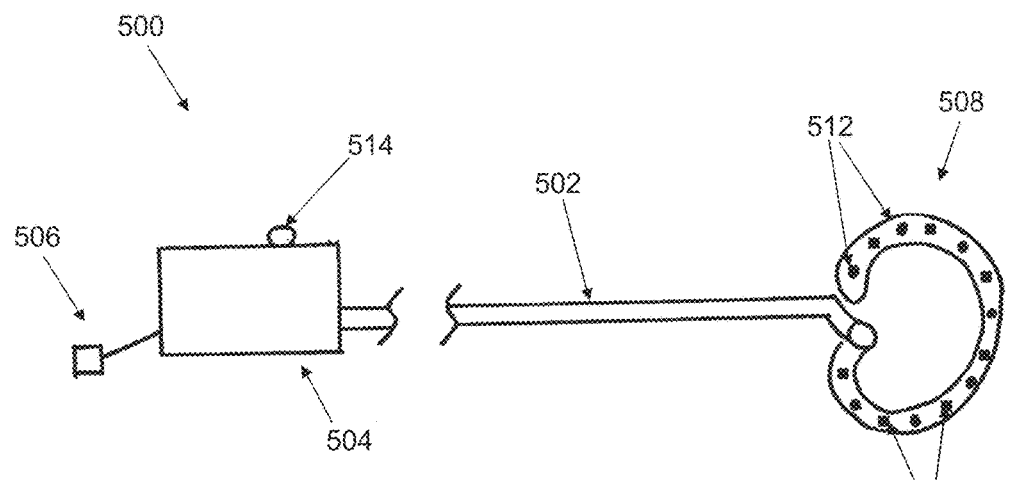
FIG. 5 depicts one variation of an epicardial ablation device.

Depending on the tissue to be ablated and the desired ablation pattern (e.g. lesion geometry and size) desired, a second ablation device may be provided, where the second ablation device corresponds to the first ablation device. A second ablation device may increase the tissue ablation area and/or may otherwise alter the ablation characteristics of the first ablation device (e.g. by constructive or destructive interference). For the purposes of ablating tissue of a left atrium, a second ablation device may be provided to help ensure that the lesion formed by ablating tissue spans at least portion of tissue that is between them. In the treatment of atrial fibrillation it may be desirable to electrically isolate the fibrillating tissue from other tissues. In some variations, the formation of a lesion that spans the entire thickness of the atrial wall (e.g., from the endocardial surface to the epicardial surface) using one or more ablation devices may improve the electrical isolation of a portion of the atrial wall from other portions of the heart. Accordingly, in some variations, ablation devices may be placed on opposite sides of a tissue wall such that a lesion that spans a substantial portion of the tissue wall between the ablation devices may be formed. In some variations, positioning a first ablation device on an interior wall (endocardial surface) of the left atrium, and positioning a second ablation device on an exterior wall (epicardial surface) of the left atrium opposite to the first ablation device, may help form a lesion that spans at least a portion of the tissue between the first and second ablation devices. FIG. 5 illustrates one variation of an epicardial ablation device (500) that may be used with an endocardial ablation device to form a lesion in the left atrium. The epicardial ablation device (500) may comprise an elongate body (502), handle portion (504), ablation source (506), and an ablation array (508). As shown in FIG. 5, the ablation array (508) may be located at the distal portion of elongate body (502). The ablation array (508) may comprise magnets (510) and ablation elements (512) which may correspond to the magnets (410) and ablation elements (412) of the endocardial ablation device (400). The magnets of the epicardial and endocardial ablation devices attract each other when the ablation arrays are placed on opposite sides of tissue, which may act to align the epicardial and endocardial ablation devices. For example, the magnets (510) may be positioned on the epicardial ablation array (508) such that they may be aligned with the magnets (410) of the endocardial ablation array (408), e.g. magnets (510) may correspond to, or be mirror images of magnets (410). As with the magnets, the ablation elements (512) may correspond to, or be mirror images of the ablation elements (412), or they may be interlaced between the ablation elements (412). In some variations, the alignment and attraction of the magnets may position the endocardial and epicardial ablation devices such that the ablation elements of the ablation devices are aligned across from each other. The shape of the ablation array (508) as shown in FIG. 5 is semi-circular, however, other variations of ablation arrays may have any shape as may be suitable for accessing and contacting the target tissue. In some variations, the shape of ablation array (508) may be a mirror image, or complementary image, of the endocardial ablation array (408). For example, the semi-circular shape of the ablation array (508) may be suited for circumscribing vascular structures, such as veins or arteries. Other variations will be described in detail below. The ablation array (508) may be made from a flexible or shape-memory material, such that it may be advanced to the target tissue in a substantially straight configuration, and may be deployed and contacted to tissue in a curved configuration. For example, ablation array may be advanced to, and contacted with, an external wall of a vascular structure, e.g. artery, vein, heart chamber, and/or atrial appendage. The ablation elements of the endocardial array and the epicardial array may be in communication with each other, so that they may apply ablation energy in a concerted or programmed fashion.

The handle portion (504) located at the proximal end of elongate body may comprise actuating elements that control the movement and/or action of the elongate body and ablation array. In some variations where the endocardial ablation device (500) is manually operated, the handle (500) may be ergonomic, while in other variations where the device is mechanically/electrically operated, the handle (500) may comprise an interface to receive and execute instructions from a computing device. The handle portion (504) may comprise an ablation array actuator (514), which may be used to regulate application of ablation energy/substances to the ablation array to the target tissue (e.g. frequency, duty cycle, magnitude/amplitude, etc.). In some variations, the handle portion (504) may be in communication with the handle portion (404) of the endocardial ablation device (400), such that ablation energy from both ablation devices may be applied in-phase or out-of-phase to form a desired ablation wavefront and/or profile. Additionally, the handle portion (504) may comprise an actuating mechanism that controls the movement and position of elongate body (502). The handle portion (504) may also comprise an interface to ablation source(s) (506), and provide a conduit or conduction pathway from the ablation source(s) (506) to the ablation array. For example, the ablation source (506) may comprise a reservoir of cryogenic substances (e.g., for cryo-ablation), which may be transported through a lumen in the elongate body (502) to the ablation array. Alternatively or additionally, the ablation source (506) may comprise a source of radioactive substances (e.g., radioactive seeds or fluids), and/or a light beam source (e.g., for laser ablation), and/or an ultrasound source (e.g., for HIFU' ablation), and/or a radiofrequency source, and the like, which may be delivered or transmitted from the handle portion to the ablation array. In some variations, different ablation sources may be used together in the same ablation device.

Variations of Ablation Arrays

Figure 6A:
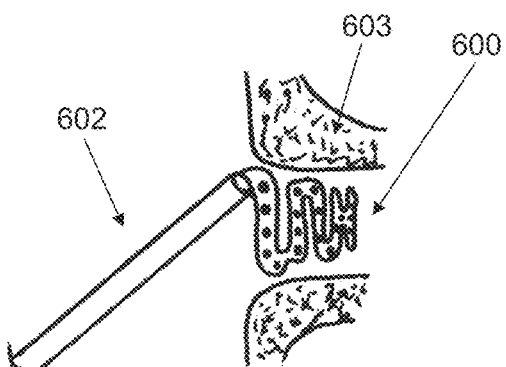
FIGS. 6A-6F depict side and front views of different ablation arrays that may be used with various ablation devices, including the devices shown in FIGS. 4 and 5.
Figure 6B:
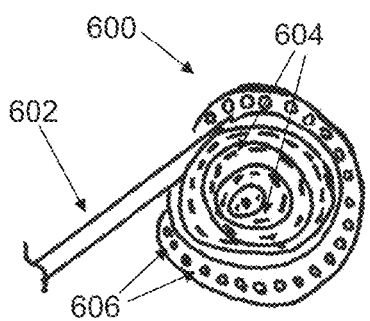
Figure 6C:
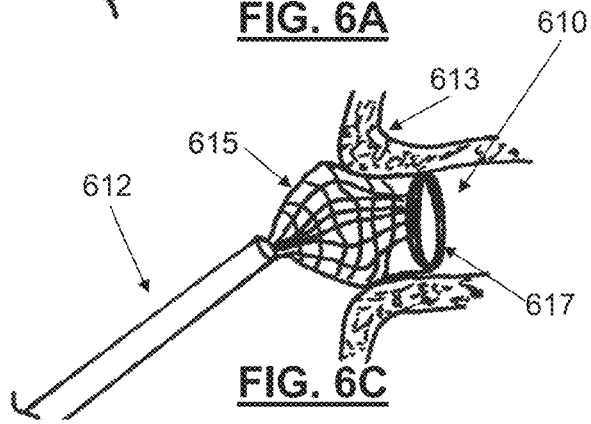
Figure 6D:
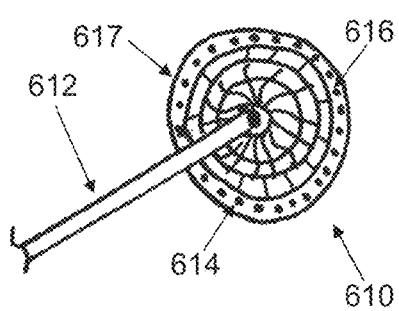
Figure 6E:
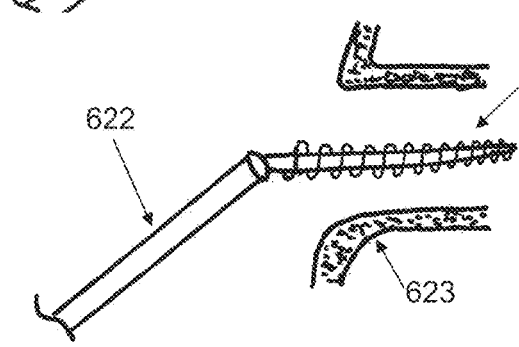
Figure 6F:
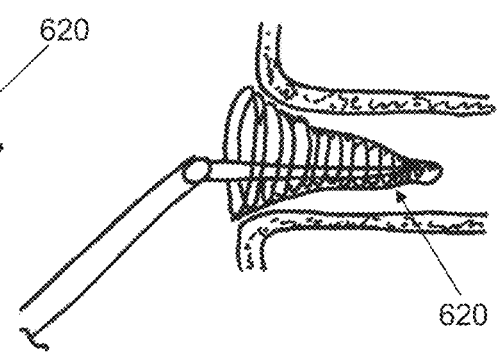

While the ablation devices depicted and described in FIGS. 4 and 5 are shown as having a semi-circular shape, ablation arrays may have other geometries. Ablation and/or other tissue-affecting arrays may have a variety of geometries and sizes as appropriate to accommodate and contact the target anatomical structure. For instance, ablation arrays with various geometries may be suitable for contacting and ablating tissue, especially vascular or cardiac tissue. Several variations of ablation arrays are shown in FIGS. 6A-6F. A side view and front view of a spiral ablation array (600) inserted in the opening of a vascular structure (603) (e.g. pulmonary vein) is shown in FIGS. 6A and 6B, respectively. As shown there, the spiral ablation array (600) may be coupled to the distal portion of an elongate body (602), where ablation elements (604) and magnetic elements (606) are arranged throughout the curves of the array (600) such that they may contact the walls of the vascular structure (603). FIGS. 6C and 6D depict a side view and a front view of a woven ablation array (610), respectively. The ablation array (610) may be attached at the distal portion of an elongate body (612), and may comprise a woven portion (615) and a rim (617) located along a distal perimeter edge of the woven portion. Ablation elements (614) and/or magnetic elements (616) may be arranged throughout the array, for example, along the rim (617) and/or on various locations on the woven portion (615). The size and shape of the woven portion (615) may be configured to position the ablation elements (614) and the magnetic elements (616) in order to accommodate the geometry of the target tissue (613), e.g., where the expanded size and shape of the woven portion may be bent, shaped, molded or otherwise constrained by the geometry of the target tissue. The woven portion (615) may be used as an ablation conduit or array, and may be arranged to be in proximity to target ablation tissue. Alternatively or additionally, the woven portion (615) may help stabilize the array (610) during ablation without occluding the pulmonary vein. The woven portion (615) may be constructed from various fibers, where the density of the weave may be adjusted according to the degree of perfusion desired. The fibers of the woven portion may be made of polypropylene, polyurethane, polyethylene, polytetrafluoroethylene, as well as metal alloys such as stainless steel and/or nickel titanium alloy. The woven portion may be self-expanding or mechanically expanded to fill the lumen or orifice of the vascular structure, and may be adjusted according to the size of the vascular structure. In some variations, the woven portion may be made of a shape-memory material so that the woven array (610) may have a compressed delivery configuration and an expanded deployed configuration. The size of the woven portion may be adjusted to ablate anatomical structures with dimensions of about 8.0 mm to about 30 mm, or about 12.0 mm to about 18.0 mm. Another variation of an ablation array (620) is shown in FIGS. 6E and 6F. As shown there, a tapered spiral ablation array (620) may be coupled to the distal portion of an elongate body (622), where ablation elements and/or magnetic elements may be arranged throughout the tapered spiral ablation array (620). The tapered spiral ablation array (620) may comprise a single continuous flexible backbone that is wound around the elongate body (622). Ablation elements may be distributed along the length of the backbone. In some variations, the backbone of the spiral ablation array (620) may be a wire that is electrically conductive, and may itself be capable of ablating tissue without additional ablation elements. The spiral ablation array (620) may have a first collapsed configuration shown in FIG. 6E, where the ablation array may be closely wound around the distal portion of the elongate body (622), e.g., with a tight radius of curvature. The narrow profile of the array in the collapsed configuration may help navigate the array atraumatically through narrow anatomical structures, and may also be inserted into folded or creased tissue structures. The ablation array (620) may be retained in its collapsed delivery configuration by a sheath that may be slidably disposed over the array (not shown), and/or by retaining tension on the backbone. FIG. 6F depicts a second expanded configuration of the tapered spiral ablation array (620), where removing the sheath and/or reducing the tension on the backbone of the spiral ablation array (620) may allow the backbone to loosen the radius of curvature such that the profile of the array expands. In some variations, expanding the ablation array may act to dilate a narrow tissue structure, e.g., open a folded or creased tissue structure, enlarge a tissue lumen or aperture for the insertion of additional devices, etc. In some variations, the ablation array (620) may help to maintain perfusion during ablation, and may be an alignment reference point for epicardial elements at various locations along the pulmonary veins. The ablation and magnetic elements may be arranged in any of the previously described configurations, and may be arranged to help stabilize the ablation device during the ablation procedure.

Figure 6G:
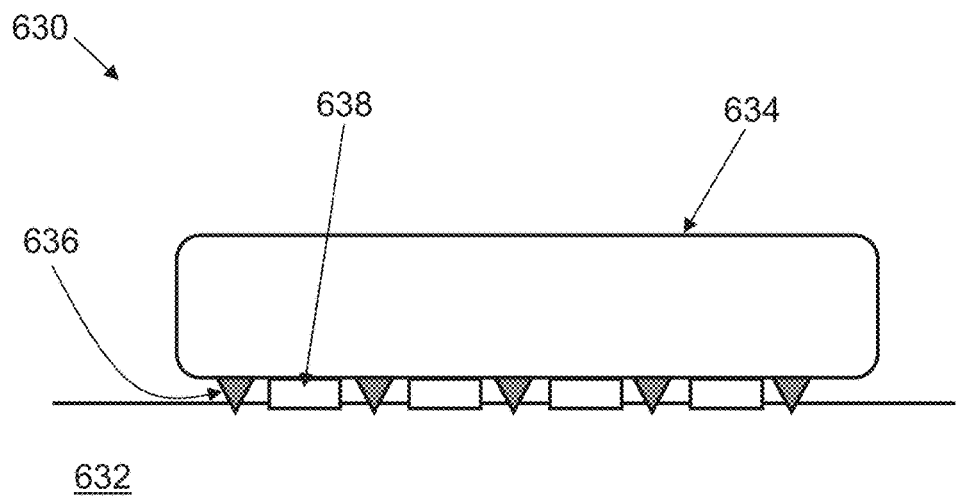
FIGS. 6G and 6H depict variations of ablation arrays comprising temperature sensors.
Figure 6H:
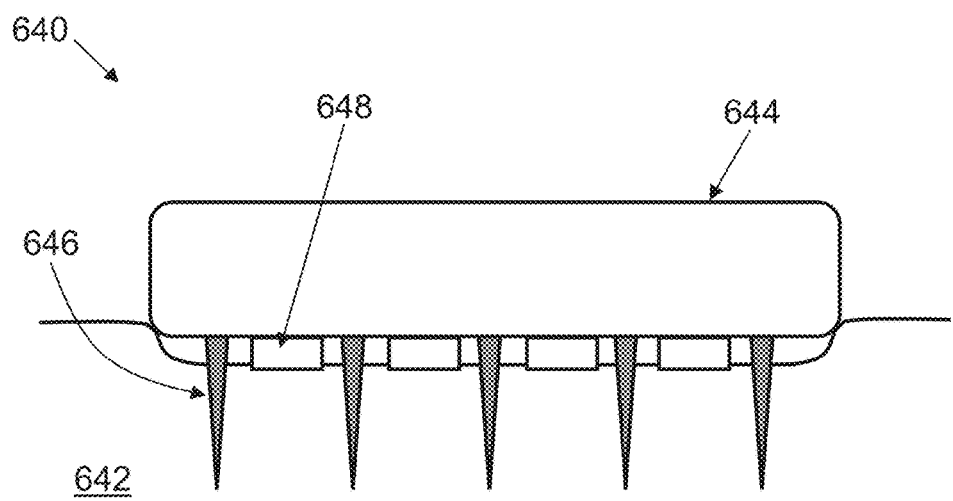

Any of the ablation arrays described above may optionally comprise one or more temperature sensors. Temperature sensors may be used to measure the ablation energy that has been applied to a tissue, and may be used to evaluate the degree to which tissue is ablated. The measurement of temperature changes in the tissue during the application of ablation energy may be used to regulate the duration, power, and/or frequency of the ablation energy (e.g., by providing feedback information to the ablation array and/or ablation array controllers). Monitoring the temperature of the tissue during ablation may also help prevent excessive or harmful damage to peripheral tissues. The one or more temperature sensors may be thermocouples, thermsistors, thermal resistive sensors (RTD), and the like. One example of an ablation array with temperature sensors is depicted in FIG. 6G. Ablation array (630) may comprise an ablation array substrate or housing (634), one or more ablation elements (not shown), one or more alignment magnets (638) and one or more atraumatic temperature sensors (636) on the tissue-facing surface of the ablation array. The alignment magnets (638), temperature sensors (636), and ablation elements may be arranged in any suitable configuration on the tissue-facing surface of the ablation array, for example, the alignment magnets (638) may be arranged such that the ablation elements of two ablation arrays positioned on opposite sides of a tissue may attract each other to align the ablation elements of one ablation array to the other. The atraumatic temperature sensors (636) may be pressed into the tissue (632) without puncturing or piercing it to measure the temperature of the tissue. Another example of an ablation array with temperature sensors is depicted in FIG. 6H. Ablation array (640) may comprise an ablation array substrate or housing (644), one or more ablation elements (not shown), one or more alignment magnets (648) and one or more sharp temperature sensors (646) on the tissue-facing surface of the ablation array. The alignment magnets (648), temperature sensors (646), and ablation elements may be arranged in any suitable configuration on the tissue-facing surface of the ablation array, as previously described. The sharp temperature sensors (646) may be inserted into tissue (642) to measure the temperature of the tissue at a certain depth from the surface of the tissue (642). In some variations, the sharp temperature sensors (646) may pierce or puncture the tissue (642) in order to gain access to deeper tissue regions. The sharp temperature sensors (646) may also have a length that corresponds to the thickness of the tissue, and in some cases, may penetrate through the entire length of the tissue. Temperature sensors that penetrate through substantially the entire thickness of the tissue may provide temperature data across the entire span of the tissue, which may provide an indication of the uniformity of the tissue ablation, as well as provide information about the temperature gradient across the tissue. This may help improve the accuracy of the tissue temperature measurement that is fed back to the ablation array and/or ablation array controllers.

Figure 6I:
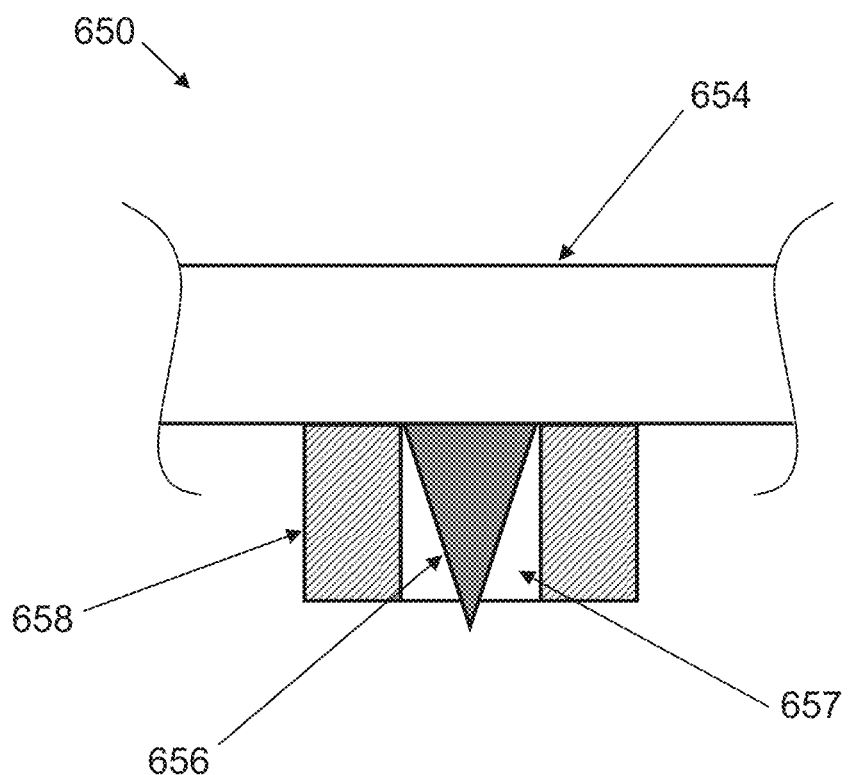
FIG. 6I depicts a partial cutaway of one variation of a temperature sensor that may be encapsulated in an alignment magnet of an ablation array.

In the variations depicted in FIGS. 6G and 6H, the alignment magnets and temperature sensors are located adjacent to each other, however, in other variations, the alignment magnets and temperature sensors may be incorporated together in one location. This may help to reduce the overall size of the ablation array, which may reduce the profile of the array for ease of delivery to the target tissue site. For example, an ablation array may have alignment magnets that have a lumen sized and shaped for encapsulating a temperature sensor. FIG. 6I depicts a regions of one example of an ablation array (650) comprising a housing (654), a temperature sensor (656) and an alignment magnet (658) encapsulating the temperature sensor. The alignment magnet (658) may comprise a lumen (657) that is sized and shaped for the temperature sensor (656). The temperature sensor (656) (which may be an atraumatic or tissue-piercing or sharp temperature sensor) may protrude from the lumen (657), or may be flush with the opening of the lumen (657). In other variations, an ablation array may comprise one or more ablation elements that each comprise a lumen such that a temperature sensor may be encapsulated in the lumen. In still other variations, an ablation array may comprise ablation elements, alignment magnets, and/or temperature sensors that may be retracted into a housing of the ablation array. For example, during delivery of the ablation array to the target tissue site, the ablation elements, alignment magnets, and/or temperature sensors may be in a first retracted configuration, such that the profile of the ablation array is narrow. After the ablation array has been generally positioned at the target tissue site, the ablation elements, alignment magnets, and/or temperature sensors may be a second protracted configuration, where the ablation elements, alignment magnets, and/or temperature sensors are capable of contacting the target tissue for alignment, ablation, and/or measurement of temperature.

Occlusion Device

Figure 7:
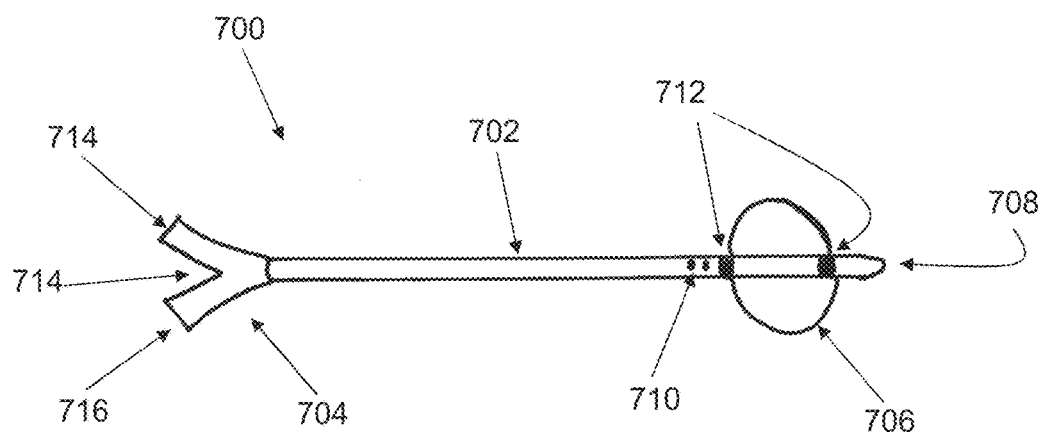
FIG. 7 depicts one variation of an occlusion device comprising an expandable element.

As described previously, some methods may include steps to help maintain hemostasis in the course of the procedure for the treatment of atrial fibrillation. For example, in procedures where access to an endocardial surface of the heart is gained using the LAA as a port, it may be desirable to close and/or exclude the LAA to maintain hemostasis and/or help prevent thrombosis. In some variations, a procedure for the treatment of atrial fibrillation may also include the temporary or permanent closure, and/or occlusion, and/or removal of the left atrial appendage. FIG. 7 illustrates one variation of an occlusion device (700) that may be used with the devices and methods described here. The occlusion device (700) may comprise an elongate body (702), an insert port (704) at a proximal portion of the elongate body, and an expandable member (706) at a distal portion of the elongate body. The elongate body (702) may have one or more lumens, for example, a guide wire lumen (708) sized and shaped for passing a guide wire therethrough. The elongate body (702) as shown in FIG. 7 may also comprise one or more side apertures (710) and imaging markers (712). Any number of side apertures (710) may be provided for infusion of any fluid substance, such as a contrast agent or pharmacological agent (e.g., heparin, antibacterial agent, etc.). The imaging markers (712) may be radiopaque or echogenic, etc., as appropriate for the imaging modality used to monitor the position of the occlusion device (700).

The elongate body (702) may be made from one or more rigid and/or flexible materials. In some variations, the elongate body (702) may be steerable. An insert port may comprise one or more apertures for the insertion of fluids or devices through the elongate body (702). For example, the insert port (704) may comprise a guide wire aperture (714) and a fluid lumen (716). The guide wire aperture (714) and the fluid lumen (716) may each have independent lumens that may merge into one lumen at a bifurcation (717) of the insert port (704), or may each have separate lumens in the elongate body (702). The guide wire aperture (714) may be continuous with the guide wire lumen (708), and the fluid lumen (716) may be continuous with a cavity of the expandable member (706), such that the introduction of fluid into or out of the fluid lumen (716) may expand or constrict the expandable member. Optionally, the insert port (704) may also comprise actuation mechanisms for navigating and adjusting the shape of the elongate body (702), as well as control the motion of a guide wire, and the expansion of the expandable member (706).

The expandable member (706) may be any structure that comprises a first small profile and a second larger profile, for example, a balloon or an articulating polygonal structure, e.g. rectangular prism or tetrahedron, and the like. The expandable member (706) may be sized and shaped to fit within the guide wire lumen (208) of the closure device (200) so that it may be advanced and/or withdrawn through the lumen (208). In some variations, the expandable element (706) may have a first collapsed configuration, and a second expanded configuration. For example, the rounded expandable element (706) shown in FIG. 7 may have a diameter of about 15 mm to about 30 mm, e.g., 20 mm. The expandable member may be made of various materials, including polymeric and/or metallic materials. Examples of polymers that may be used in an expandable member may include materials such as latex, silicone, polyisoprene, polyethelene. Example of metals and/or metallic alloys that may be used with an expandable member may include nitinol, stainless steel, titanium and the like. The expandable member may be configured to either self expand or be mechanically expanded by an actuator. For example, the expandable member (706) may be transitioned from the small profile to the larger profile by introducing positive pressure or by a mechanical actuation. In some variations, a balloon expandable member may be urged into the larger configuration by applying positive fluid (gas or liquid) pressure into the lumen of the balloon. The expandable member may have any shape and size as appropriate for the target tissue. For example, a round expandable balloon may be used to occlude a vascular structure, such as a vein or an atrial appendage, e.g. LAA.

Figure 18A:
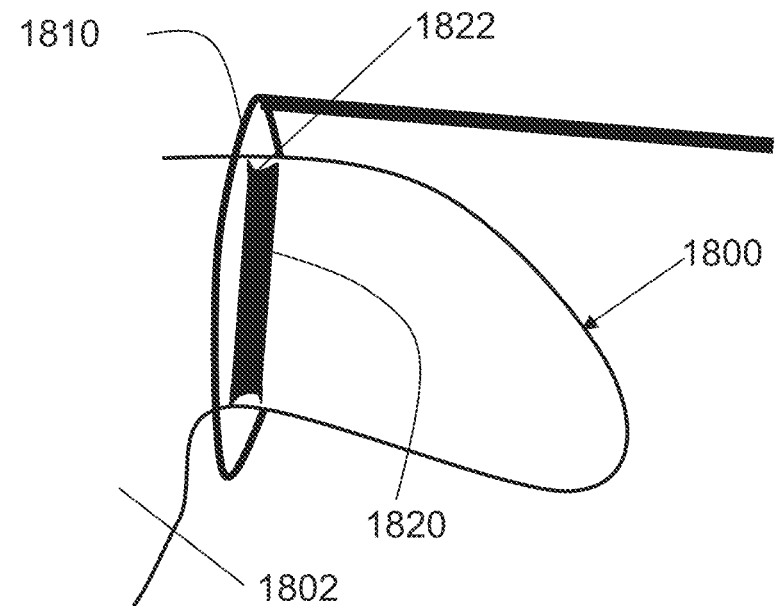
FIGS. 18A and 18B depict one variation of an occlusion device that may be used to position a closure element around a left atrial appendage.
Figure 18B:
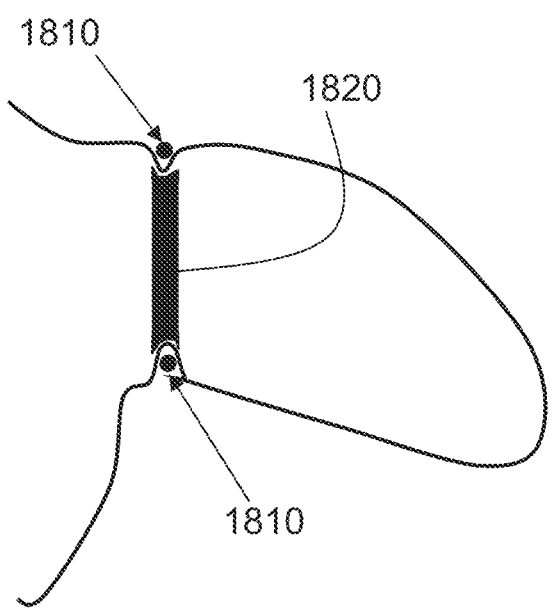

Another variation of a device that may be used for occluding the LAA is depicted in FIGS. 18A and 18B. As shown there, an occlusion device (1820) may comprise grooves (1822) in its deployed configuration. In some variations, the closure device may be deployed and positioned at the anatomical ostium of a left atrial appendage (1800). However, the occlusion device (1820) may be positioned at any desired location in the heart. The occlusion device (1820) may have a collapsed delivery configuration, which may enable it to be enclosed within a catheter or sheath and advanced through the vasculature (e.g., from a retrograde approach, or an antegrade transseptal approach) or through a port in the LAA. The occlusion device (1820) may be deployed into its expanded configuration after it is positioned at or near the ostium of the LAA. In some variations, the occlusion device may be a rounded plate or disc comprising one or more grooves circumscribing the outer perimeter. Grooves (1822) may be configured to interfit with a closure element (1810) (e.g., suture loop or snare loop) of a closure device as the circumference of the closure element is reduced, as shown in FIG. 18B. The occlusion device (1820) may be sized according to the desired degree of closure of the left atrial appendage (1800). Once the closure element (1810) has been secured and decoupled from the rest of the closure device (e.g., by cutting or detaching at a breakaway point), the occlusion device (1820) may be reverted to its collapsed configuration and withdrawn from the ostium of the left atrial appendage (1800). The devices and methods described above for closing and/or excluding the left atrial appendage may be included at the conclusion of a procedure that uses the left atrial appendage as an access site. This may be a more expedient method of closing a heart access site than other conventional methods, such as suture stitching, which may be substantially more time-consuming.

The above-described devices may be used to secure, ablate, and excise a portion of tissue to help alleviate the symptoms of atrial fibrillation. For example, the devices above may be used to secure a LAA, ablate atrial tissue in the proximity of the LAA and the pulmonary veins, and to close, and/or occlude, and/or remove the LAA. While the description below provides methods of securing, ablating, and excising tissue of the left atrium and/or LAA, it should be understood that the methods may be used to perform similar procedures on the right atrium, as well as other vascular structures or organs. Similar methods may also be used to secure, ablate, and excise tissues and/or organs that have one or more cavities therethrough, e.g. stomach, intestine, bladder, etc., for a variety of indications.

III. Methods

Methods for ablating tissue for the treatment of atrial fibrillation may generally comprise accessing targeted cardiac tissue regions, advancing ablation arrays to the targeted tissue regions, ablating the tissue regions, and withdrawing the ablation arrays once the desired degree of tissue ablation has been attained. Additionally, some methods may include the closure of the left and/or right atrial appendages, which may help reduce the risk of thrombosis and may help maintain hemostasis. Some variations of methods for tissue ablation may comprise ablating the tissue from an endocardial surface, an epicardial surface, or both. Ablation devices may access an endocardial surface of the left atrium intravascularly, and/or through the LAA via the pericardial space. Once the one or more ablation devices have been placed on the endocardial and/or epicardial surface(s), the ablation devices may be activated sequentially and/or simultaneously to achieve the desired degree of tissue ablation. Ablation array activation sequences may be repeated as may be desirable, and may comprise applying ablation energy pulses (from either or both of the endocardial and epicardial ablation arrays) of varying duration, frequency, duty cycle, power, intensity, etc. The ablation array(s) may be repositioned to ablate tissue at various desired locations. Once all the desired tissue regions have been ablated, the ablation arrays may be withdrawn. In variations where the LAA is used to access the endocardial surface on the left atrium, the LAA may be closed and/or excluded.

Epicardial and Endocardial Ablation

Figure 8A:
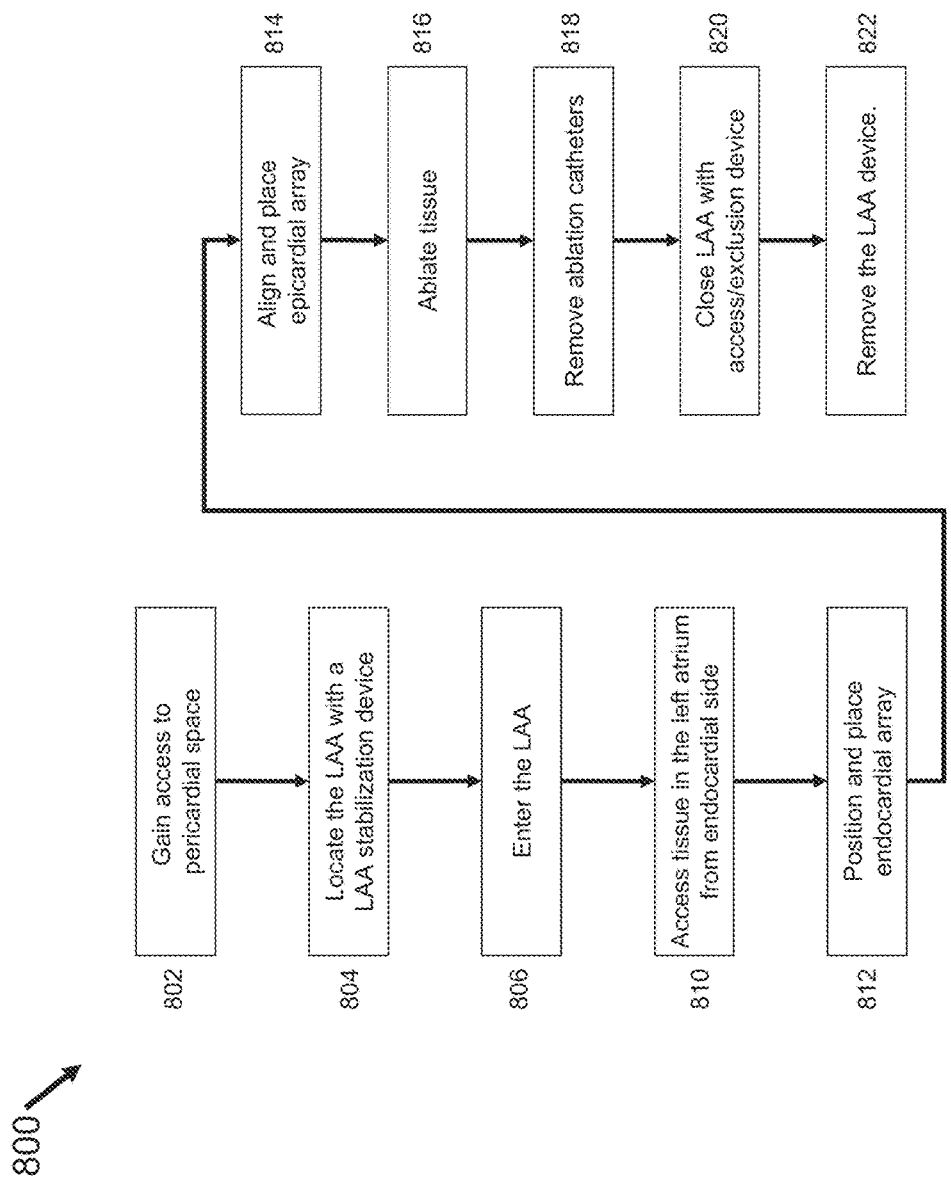
FIG. 8A depicts a flowchart that represents one variation of a method for ablating cardiac tissue from both the endocardial surface and epicardial surface.

One variation of a method that may be used to electrically isolate tissue in the left atrium and/or LAA is depicted as a flowchart in FIG. 8A. Method (800) may be used to ablate tissue from both epicardial and endocardial surfaces using surgical, intravascular and/or other minimally invasive techniques (e.g., percutaneous, small incisions or ports), and may be used in stopped heart or beating heart procedures. The method (800) may comprise gaining access to the pericardial space (802), for example, using the access devices described above. Optionally, a device may be used to locate and stabilize the LAA (804), for example, the closure device (200) as described above and shown in FIG. 2. Once access into the pericardial space and to the LAA has been established, a device may be used to enter the LAA (806), for example, by creating a puncture in the LAA. Additional devices and methods of using the LAA as an access port to deliver devices into the heart (e.g., to contact and/or affect an endocardial surface of the heart) are described in U.S. Provisional Patent Application No. 61/323,816 filed Apr. 13, 2010, which was previously incorporated by reference in its entirety, and U.S. patent application Ser. No. 13/086,390 entitled "Methods and Devices for Accessing and Delivering Devices to a Heart," filed Apr. 13, 2011, which is hereby incorporated by reference in its entirety. Various tissue regions in the left atrium (e.g., atrial wall tissue, tissue at or around the base of the pulmonary veins, tissue within the pulmonary veins, etc.) may be accessed from an endocardial side (810). Devices may be introduced into the left atrium through the LAA, for example, an endocardial ablation array may be positioned and placed in the left atrium (812). An epicardial ablation array may be aligned with the endocardial ablation array (814), for example, based on the position of the corresponding magnets on the endocardial and epicardial ablation arrays. The epicardial ablation array may be introduced to the epicardial surface of the heart using the same initial access site as the endocardial ablation array, or may be introduced through a different access site. For example, the endocardial ablation array may be introduced through a right intercostal site, while the epicardial ablation array may be introduced through a left intercostal site. Alternatively, the endocardial and epicardial ablation arrays may both be introduced through a left intercostal site, for example. Additional description of access sites are described below. The endocardial and epicardial ablation arrays may be positioned in order to obtain a particular ablation pattern, after which both ablation arrays may be activated (816). For example, the endocardial ablation array may circumscribe the base of the pulmonary veins, while the epicardial ablation array may circumscribe the trunk of the pulmonary veins. After the desired tissue regions have been ablated, the ablation devices may be removed (818), and the LAA may be occluded, closed, and/or removed (820). Once the LAA has been decoupled from the remainder of the left atrium, all devices may be retracted from the surgical site (822).

As described previously, the endocardial side of the left atrium may be accessed intravascularly and/or from the LAA via the pericardial space. The access path into the left atrium may be selected based on the targeted anatomical features in the left atrium such that the path length of the catheter and/or ablation devices may be reduced. The access path may also be selected to reduce the maneuvering, manipulating, bending, torquing, etc. that may be required to position the catheter and/or devices at the targeted tissue site in the left atrium. For example, an endocardial ablation device may access the left atrium using either an intravascular retrograde approach or an antegrade transseptal approach. Entering the left atrium via an intravascular antegrade transseptal approach may allow access to the left pulmonary veins while reducing the maneuvering, manipulating, bending, torquing, etc. of the distal portion of the device. Entering the left atrium via an intravascular retrograde approach may allow access to the right and left pulmonary veins while reducing the maneuvering, manipulating, bending, torquing, etc. of the distal portion of the device. Alternatively or additionally, entering the left atrium through the LAA via a pericardial approach may allow access to the right pulmonary veins without much maneuvering, manipulating, bending, torquing, etc. of the distal portion of the device. Any of these approaches may be used to position an endocardial ablation device in the left atrium. In some variations, a first endocardial ablation array may enter the left atrium through an intravascular approach, and a second endocardial ablation array may enter the left atrium through the LAA via a pericardial approach.

Figure 8B:
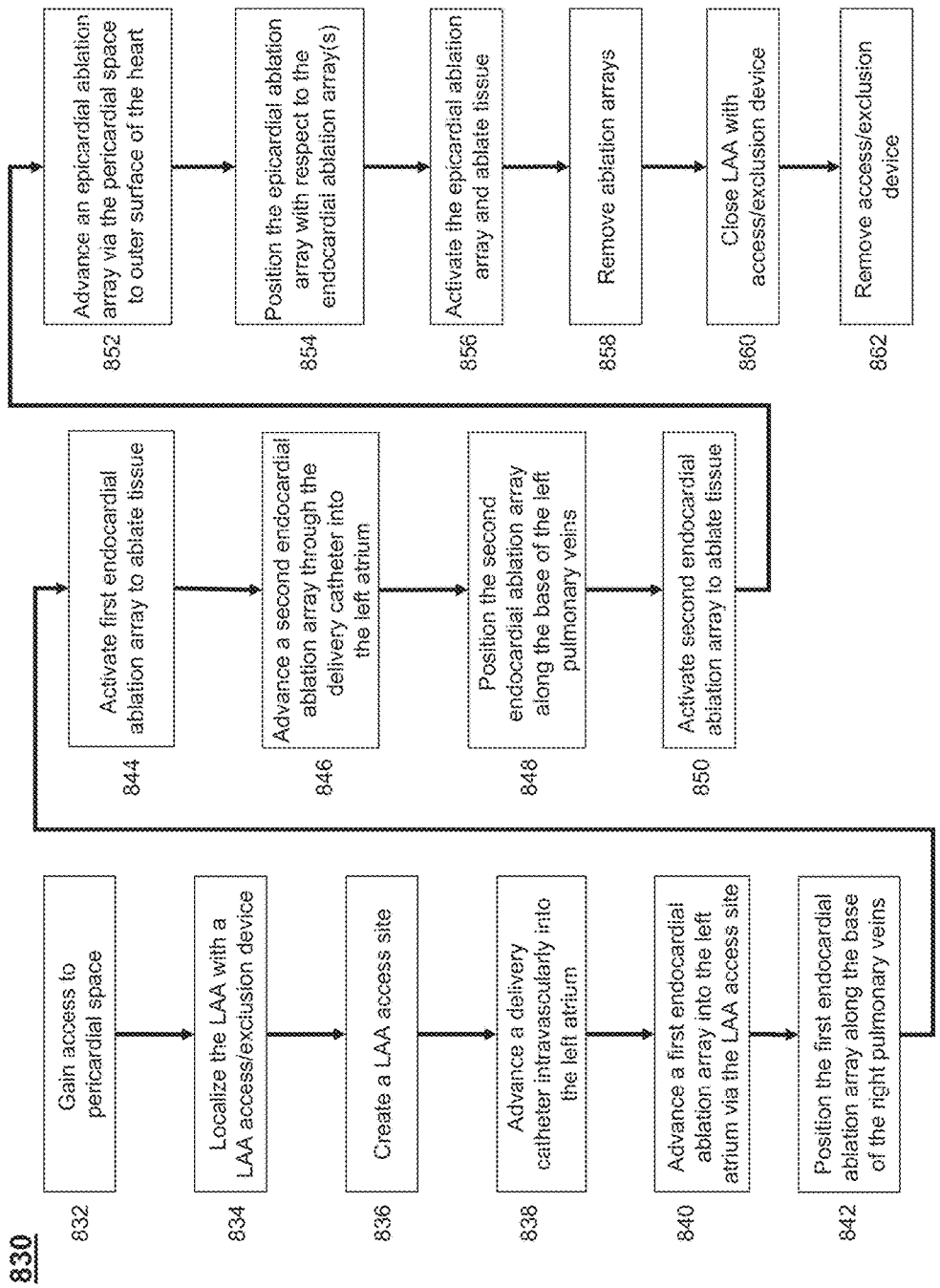
FIG. 8B depicts a flowchart that represents another variation of a method for ablating cardiac tissue from both the endocardial and epicardial surface.

One example of a method (830) that comprises accessing the endocardial surface of the left atrium both intravascularly and through the LAA via the pericardial space is depicted in FIG. 8B. As previously described, an access pathway may be created to the pericardial space (832). A LAA access/exclusion device may be used to locate and stabilize the LAA (834). Once access into the pericardial space and to the LAA has been established, a device may be used to create a LAA access site (836), e.g., by puncturing the LAA, which may allow a device to access the left atrium through the LAA. An intravascular pathway to the left atrium may also be attained by advancing a delivery catheter through the vasculature into the left atrium (838), e.g., using a retrograde or an antegrade transseptal approach. Once the intravascular and/or LAA access pathways into the left atrium have been established, a first endocardial ablation array may be advanced into the left atrium through the LAA (840). The first endocardial ablation array may be positioned at any desired tissue region in the left atrium (e.g., atrial wall tissue, tissue at or around the base of the pulmonary veins, tissue within the pulmonary veins, etc.), such as the tissue along the bases of the right pulmonary veins (842). The first endocardial ablation array may be activated to ablate tissue (844). A second endocardial ablation array may be advanced intravascularly through the delivery catheter into the left atrium (846). The second endocardial ablation array may be positioned at any desired tissue region in the left atrium (e.g., atrial wall tissue, tissue at or around the base of the pulmonary veins, tissue within the pulmonary veins, etc.), such as the tissue along the bases of the left pulmonary veins (848). The second endocardial ablation array may be activated to ablate tissue (850). An epicardial ablation array may be advanced via the pericardial space to a location on the outer surface of the heart (852), for example, a location corresponding to either or both the endocardial ablation arrays (854), and/or along tissue at or near one or more pulmonary veins, e.g., at or around the trunks of the pulmonary veins. Additional variations of advancing and positioning an epicardial device at around the trunks of the pulmonary veins are described below. In some variations, the endocardial ablation array(s) and the epicardial ablation array may be positioned opposite each other using alignment magnets. Once the epicardial ablation array is positioned at the desired location, the epicardical ablation array may be activated to ablate tissue (856). The positioning and activation of the epicardial and endocardial ablation arrays may be repeated as desired. After ablating the desired tissue regions, the ablation arrays may be removed (858). The LAA may be closed with the access/exclusion device (860), and then the access/exclusion device may be removed (862).

While the steps of the method (830) have been described in the sequence as depicted in FIG. 8B, it should be understood that the steps may take place in an alternate sequence, and certain steps may take place substantially simultaneously. For example, the delivery catheter may be advanced intravascularly into the left atrium (838) before or after the LAA access site is created (836). In some variations, the epicardial ablation array may be positioned on the epicardial surface of the heart (854) before either or both of the endocardial ablation arrays are positioned in the left atrium. The activation of the ablation arrays may occur sequentially or simultaneously. For example, the first or second endocardial ablation array and the epicardial ablation array may be activated simultaneously. Alternatively or additionally, the first and second ablation arrays and the epicardial ablation array may all be activated simultaneously, and/or the first and second ablation arrays may be activated simultaneously without activating the epicardial ablation array. In some cases, the epicardial ablation array may be activated without activating either or both of the first and second ablation arrays. The method (830) involves the use of two endocardial ablation arrays, but in other variations, only one endocardial ablation array may be used to ablate the left and/or right pulmonary veins. The single endocardial ablation array may be advanced intravascularly or through the LAA, as may be desirable.

The methods described above ablate the tissue of the left atrium and/or pulmonary veins from both the endocardial and epicardial surfaces, either simultaneously or sequentially. Placement of the ablation arrays on both the endocardial and epicardial surfaces may help ablate atrial tissue from both sides. Ablating tissue simultaneously from both sides may help promote the formation of a lesion that spans a significant portion of the thickness of the tissue between the ablation arrays. A lesion that spans a significant portion of atrial tissue thickness may help to electrically isolate fibrillating tissue. The application of ablation energy (e.g., phase, magnitude, pulse sequence, etc.), type of ablation energy (e.g., radiofrequency, laser, high intensity focused ultrasound, cryogenic agents, microwave energy, heat energy, etc.), and the shape and size of ablation arrays may be varied according to the geometry of the tissue and the ablation profile desired. For example, the endocardial ablation array may ablate tissue cryogenically, while the epicardial ablation array may ablate tissue with heat energy. Alternatively, the endocardial ablation array may ablate tissue using heat energy, while the epicardial ablation array may ablate tissue cryogenically. In other variations, the endocardial ablation array may ablate tissue using HIFU, while the epicardial ablation array may ablate tissue using microwaves. The type(s) of ablation energy used and the shape of the ablation array may be selected to limit ablation of non-target peripheral tissue.

While the methods and devices described here may be used to ablate cardiac tissue, it should be appreciated that the methods and devices described here may be adapted to ablate any tissue from any two tissue surfaces. For example, endocardial and epicardial ablation arrays may be adapted to ablate a tumor cell mass from one or more surfaces. Endocardial and epicardial ablation arrays may also be used to ablate tissue of a hollow organ (e.g., stomach, bladder, lungs, vascular structures, etc.) by positioning them opposite each other on both the inside and outside surfaces. When two ablation arrays are placed on opposite sides of tissue, they may ablate tissue therebetween in any variety of patterns, some of which are shown in FIGS. 9A-9D. These ablation patterns are described in the context of cardiac structures, however, it should be understood that these patterns may be formed in any desirable tissue, as described above. The ablation profile when using both endocardial and epicardial arrays on atrial tissue (900) may vary depending on the type of ablation energy (e.g. cryo-ablation, high intensity focused ultrasound, radiofrequency, laser, etc.). For example, as depicted in FIG. 9A, a first ablation array (908) may be placed on the endocardial surface (904) and a second ablation array (906) may be placed opposite the first ablation array (908) on an epicardial surface (902) of atrial tissue (900). Both the first and second ablation arrays (908, 906) may be simultaneously operated, where the first ablation array (908) and the second ablation array (906) may deliver ablation energy at substantially the same time. In some variations, the ablation arrays are operated to deliver ablation energy in-phase, out-of-phase, or at an offset to form the ablation pattern (910). FIG. 9B depicts an ablation pattern (920) that may arise when epicardial ablation array (916) delivers ultrasound ablation energy (e.g., HIFU) that may be reflected off endocardial array (918) back to epicardial array (916). Similarly, FIG. 9C depicts an ablation pattern (930) that may be formed when endocardial ablation array (928) delivers ultrasound ablation energy that may be reflected off epicardial array (926) back to endocardial array (928). FIG. 9D illustrates an ablation pattern (940) that may arise when both endocardial ablation array (938) and epicardial ablation array (936) reflect the ultrasound ablation energy delivered by the opposite array.

Figure 9G:
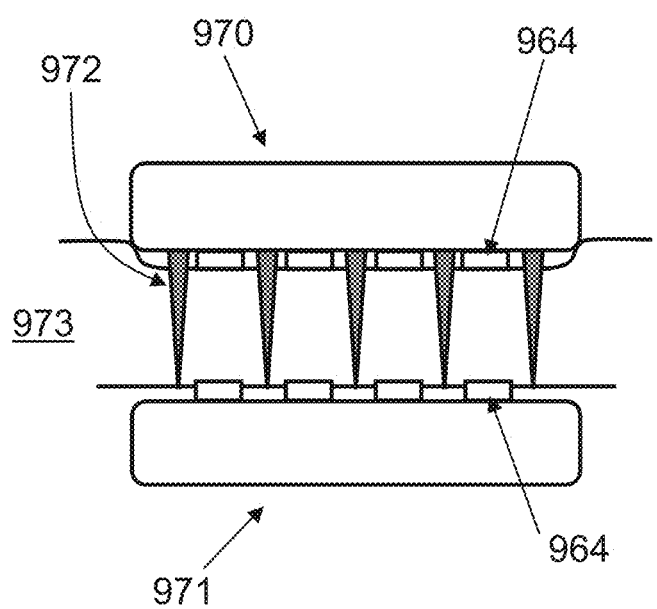

The ablation pattern created in the tissue may be monitored using one or more one or more temperature sensors on either or both the endocardial and epicardial arrays. For example, as depicted in FIG. 9E, epicardial ablation array (950) and endocardial ablation array (951) may both comprise one or more temperature sensors (952) and alignment magnets (954). Both the epicardial and endocardial ablation arrays may comprise temperature sensors so that a temperature change arising from activating the opposite ablation array may be measured, and may be used to indicate the progress of the ablation of tissue (953). In some variations, a temperature threshold may be set such that reaching or exceeding that temperature will signal an activated ablation array to deactivate. This may be used to prevent excessive or harmful damage to tissue (953). For example, the epicardial ablation array (950) may be activated when the endocardial ablation array (951) is not activated. The temperature sensors of the endocardial ablation array (951) may provide a temperature measurement as a feedback signal to the epicardial ablation array controller. For example, the duration, magnitude, and other characteristics of the ablation energy applied by the epicardial ablation array may be regulated based on the temperature measured by the temperature probe on the endocardial surface of the heart. The activation of the endocardial ablation array (951) may be similarly regulated by temperature feedback using the temperature sensors on the epicardial ablation array. In other variations, temperature sensors may only be provided on an ablation array on one side of the tissue, but not on the ablation array on the other side of the tissue. For example, in the example depicted in FIG. 9F, epicardial ablation array (960) may have one or more temperature sensors (962), while endocardial ablation array (961) may not have any temperature sensors. Both the epicardial and endocardial ablation arrays comprise one or more alignment magnets (964) that may be used to align the arrays with respect to each other across tissue (954). The tissue (963) may be clamped between the ablation arrays, such that the endocardial ablation array (961) acts as a support for the penetration of the temperature sensors of epicardial ablation array (960). The temperature sensors (962) may have a length that spans over a substantial thickness of tissue (963), which may allow the temperature of the middle of tissue (963) to be measured. In some variations, the temperature sensors of an ablation array may span the entire depth of the tissue, as depicted in FIG. 9G. As seen there, the temperature sensors (972) of the epicardial ablation array (970) may span the entire thickness of the tissue (973) and may, in some cases, even contact endocardial ablation array (971). This may allow the temperature gradient across the tissue (973) to be measured. For instance, it may be determined based on the temperature measurement if the tissue is ablated in a uniform manner, etc. Such data may be fed back to an ablation controller to adjust the power, intensity, frequency, magnitude, etc. of the ablation mechanism to attain the desired ablation pattern. As described previously, the temperature sensors may be atraumatic or may be tissue-piercing, as may be desirable.

Figure 10A:
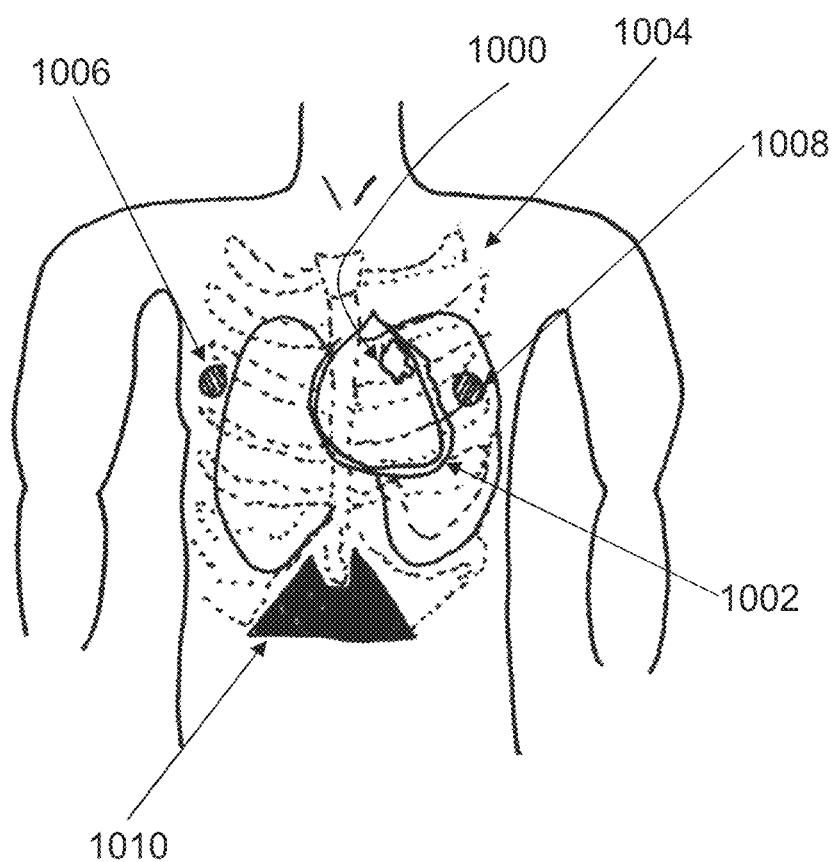
FIGS. 10A-10S depict one example of an ablation method for ablating tissue around the pulmonary veins, and for closing, and/or occluding, and/or removing the left atrial appendage.
Figure 10B:
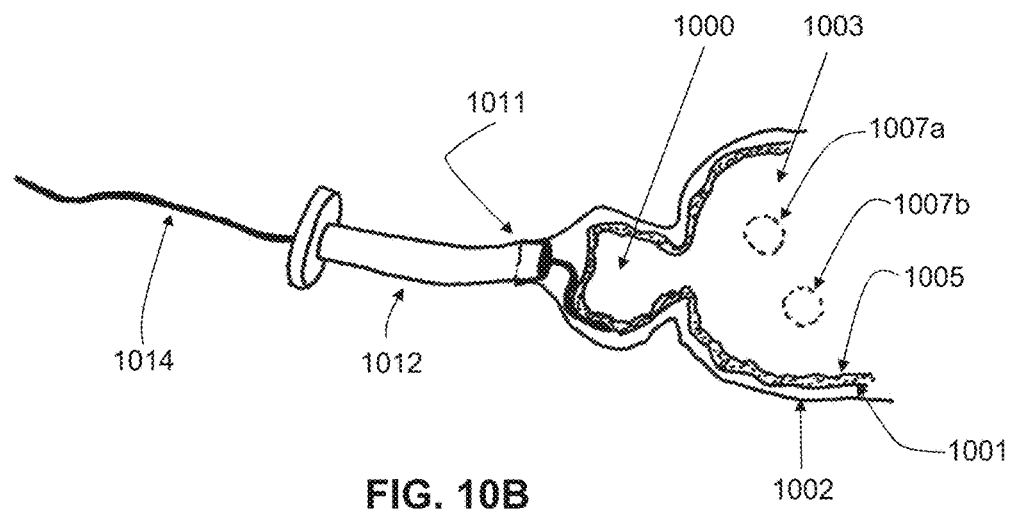
FIGS. 10B-10G schematically illustrate the use of a closure device to locate and secure the left atrial appendage.
Figure 10C:
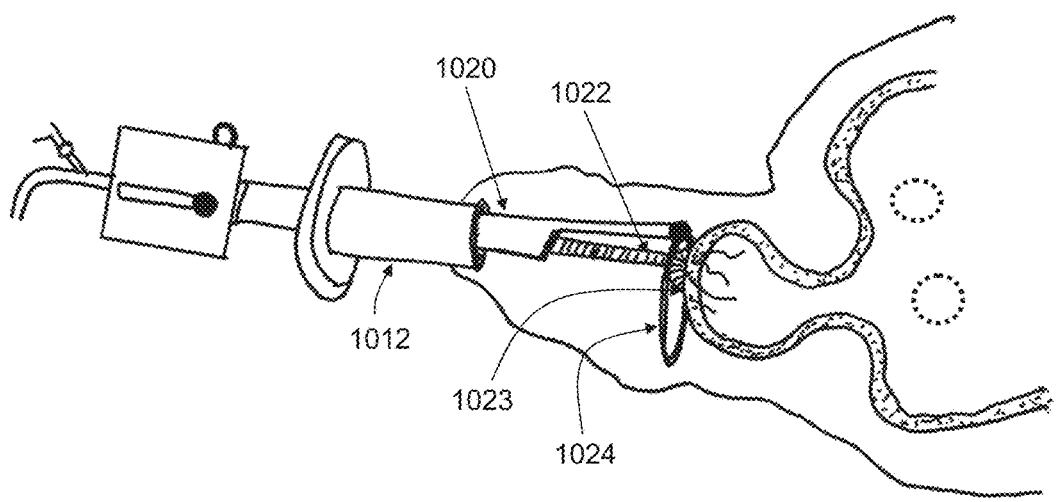
Figure 10D:
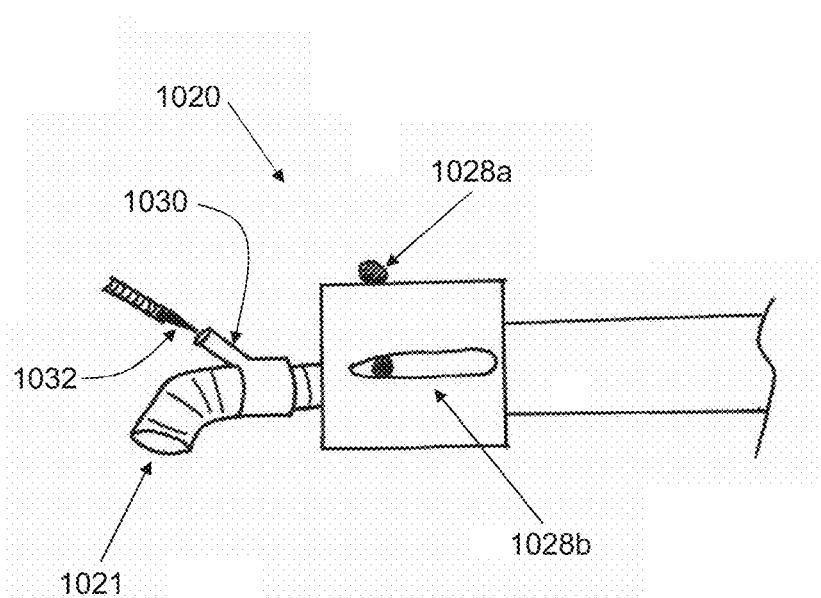
Figure 10E:
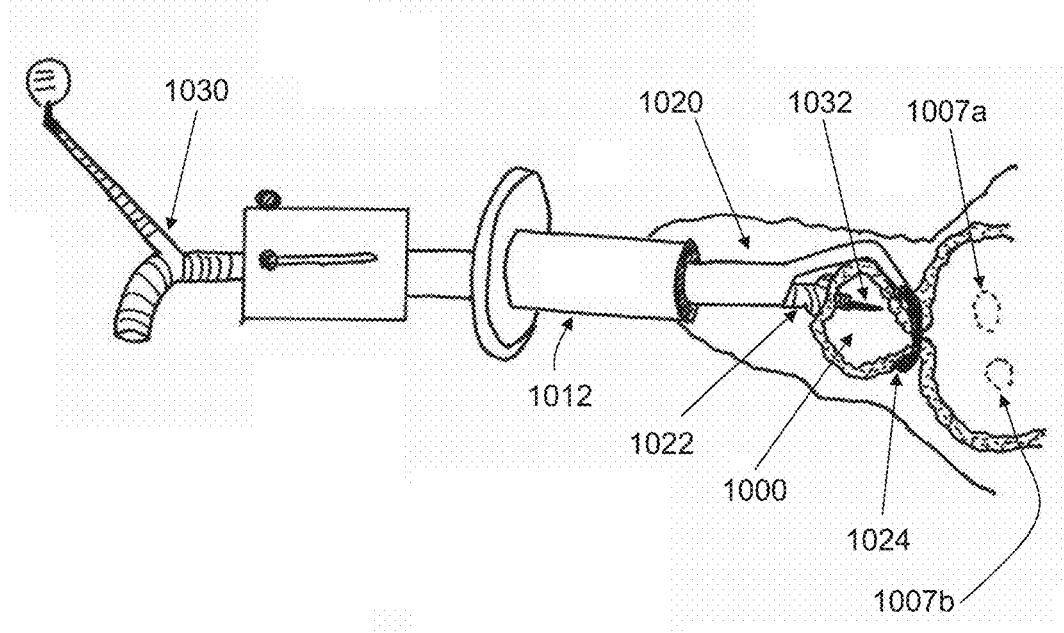
Figure 10F:
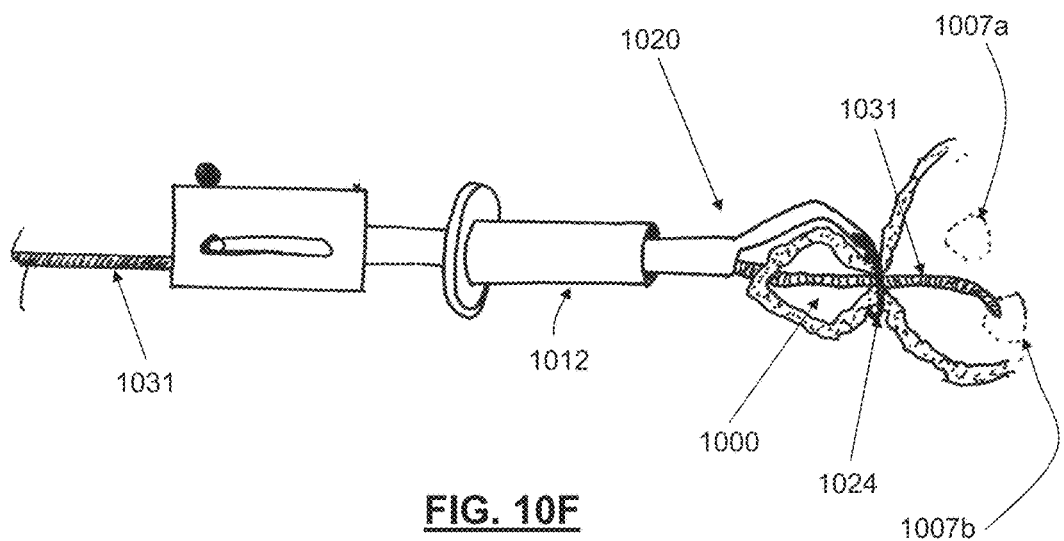
Figure 10G:
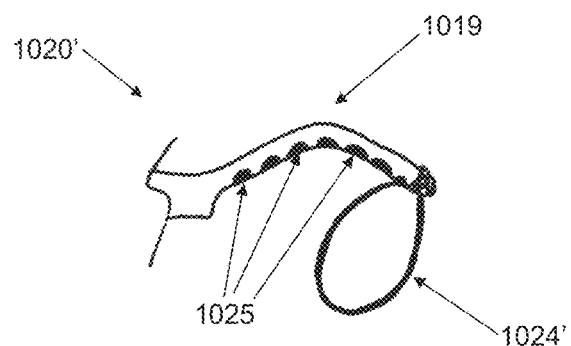
Figure 10H:
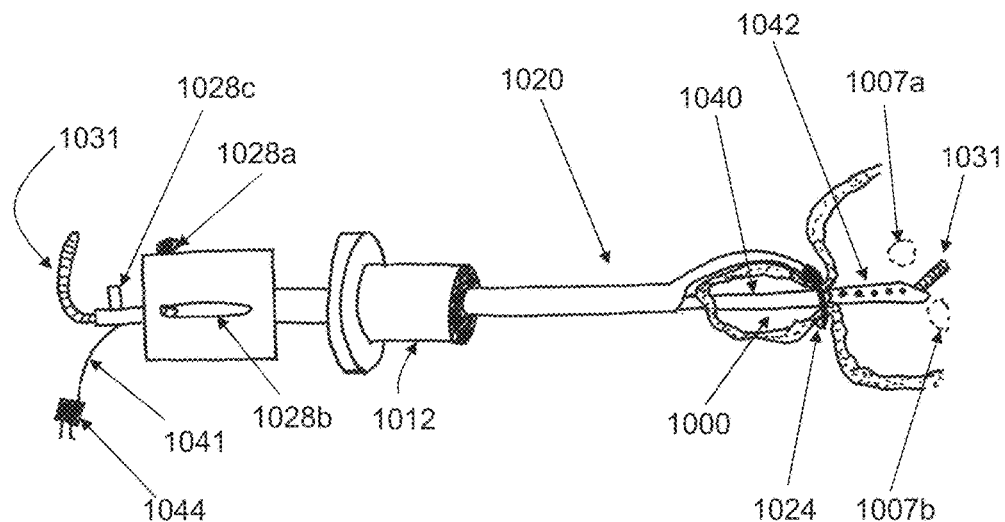
FIGS. 10H-10L schematically illustrate the positioning of endocardial and epicardial ablation devices.
Figure 10I:
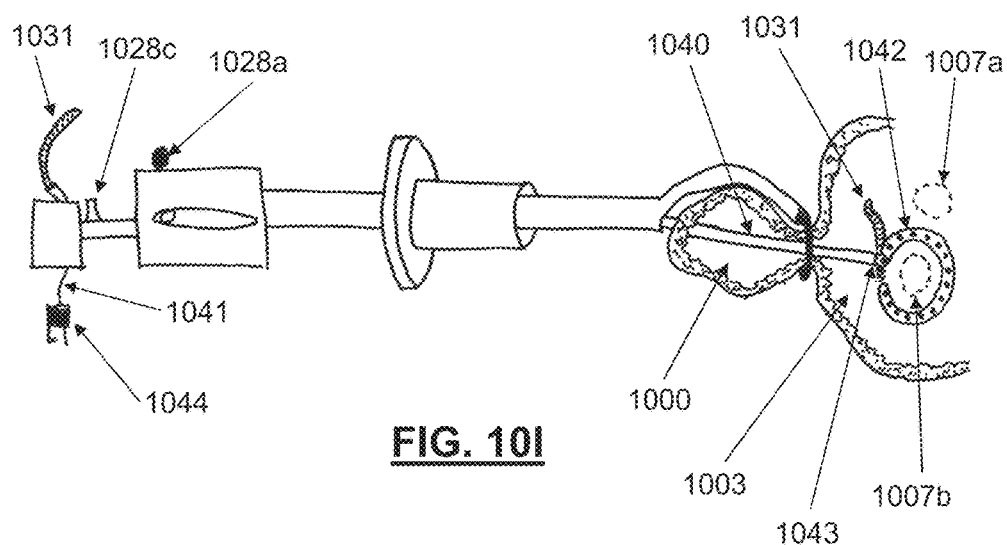
Figure 10J:
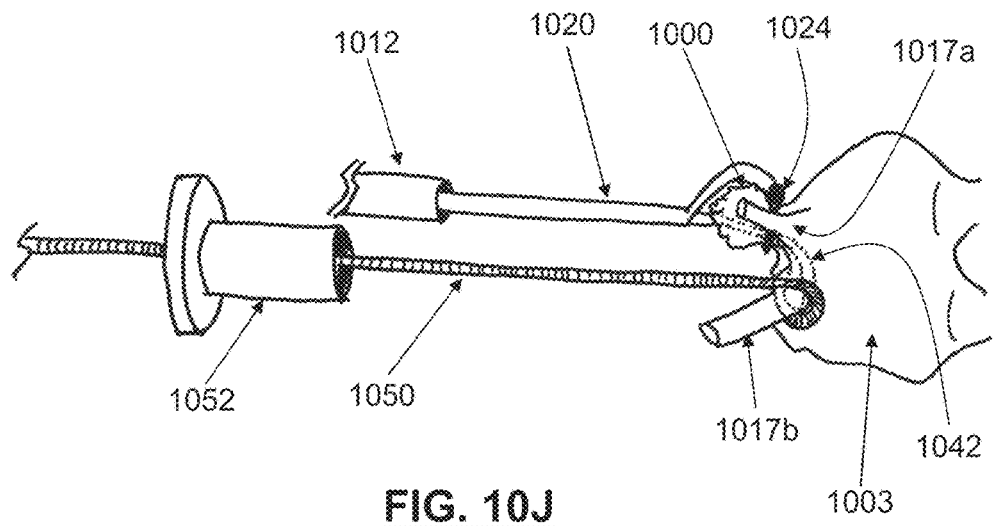
Figure 10K:
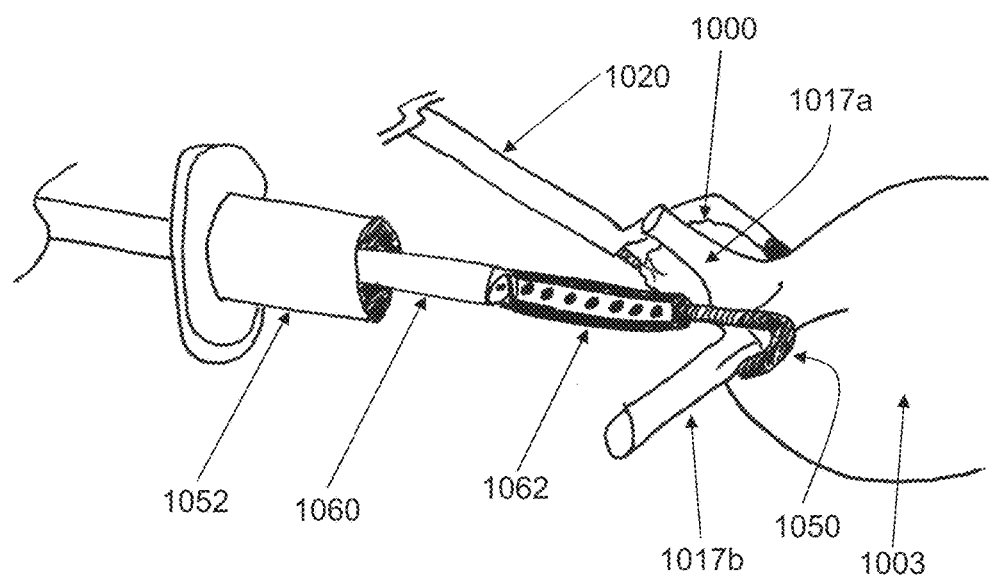
Figure 10L:
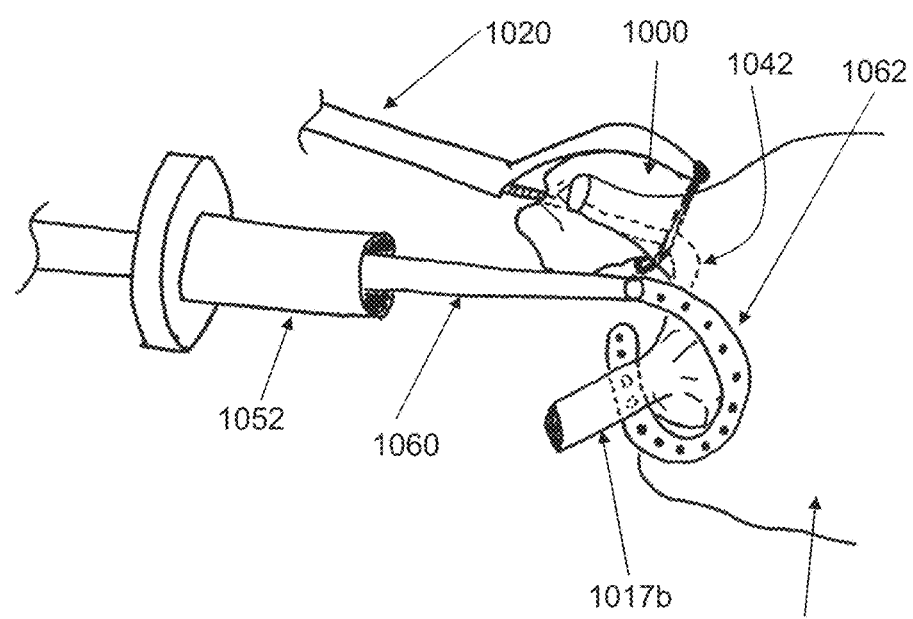
Figure 10M:
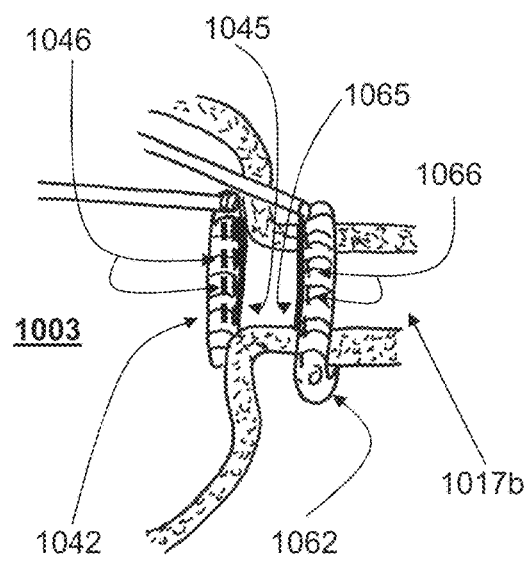
FIGS. 10M-10N depict the alignment of endocardial and epicardial arrays using magnetic components.
Figure 10N:
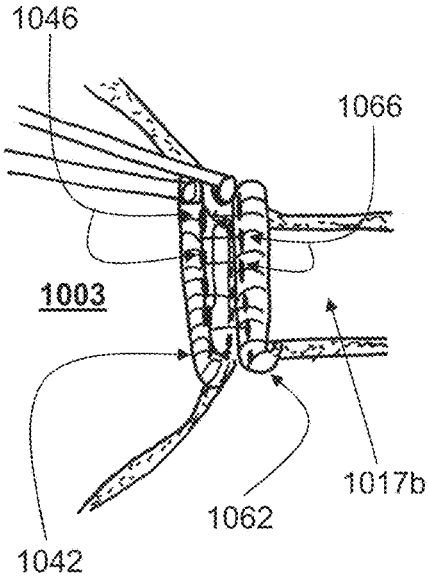
Figure 10O:
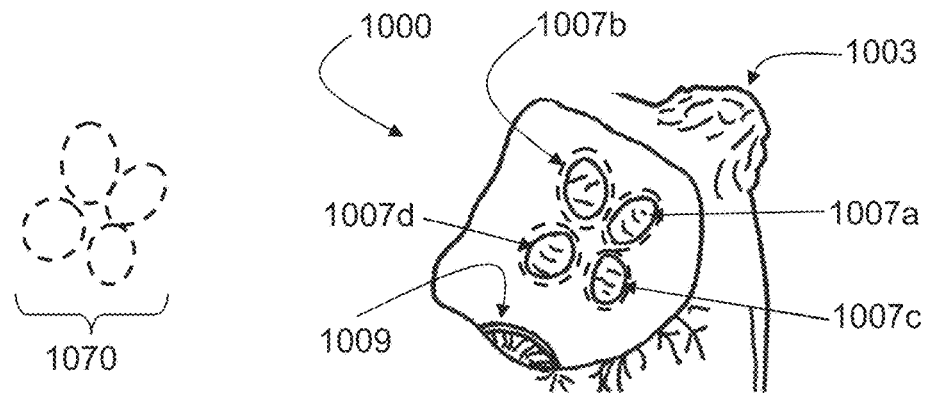
FIGS. 10O-10Q depict examples of ablation profiles that may form lesions that electrically isolate the tissue at or around or within the pulmonary veins.
Figure 10P:
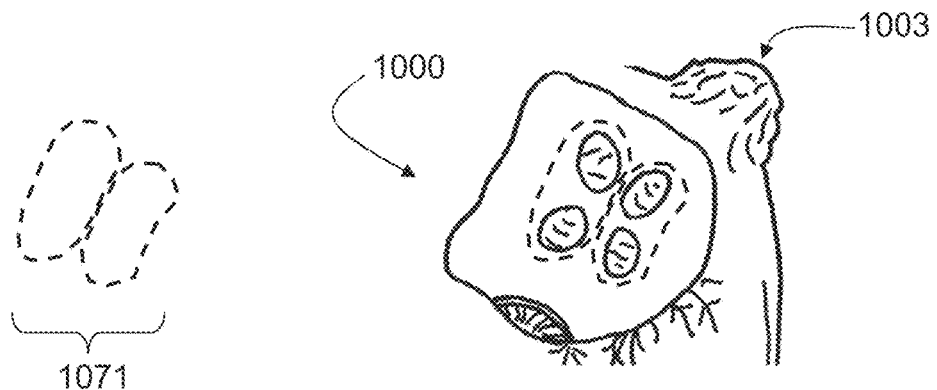
Figure 10Q:
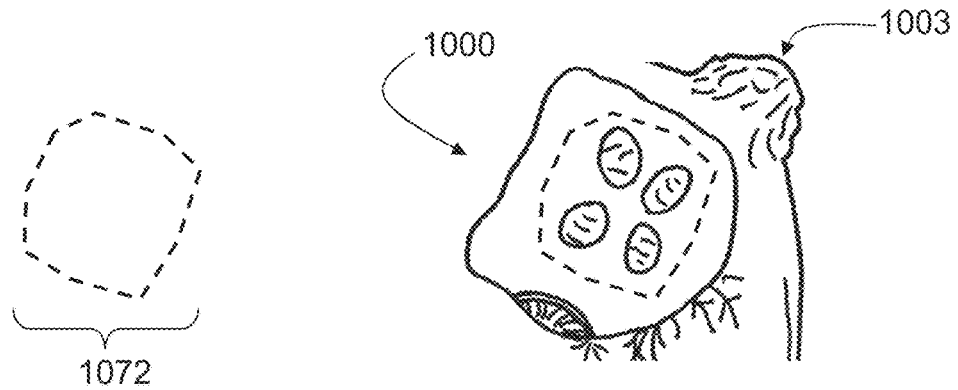
Figure 10R:
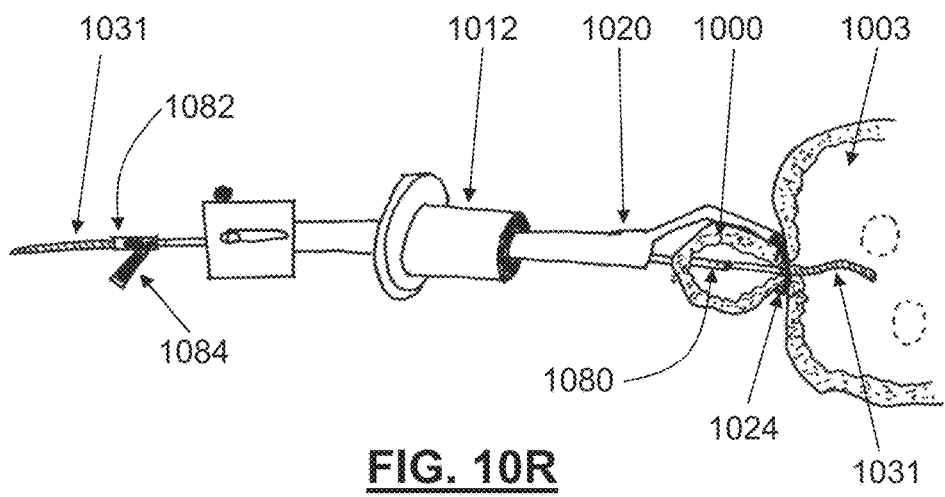
Figure 10S:
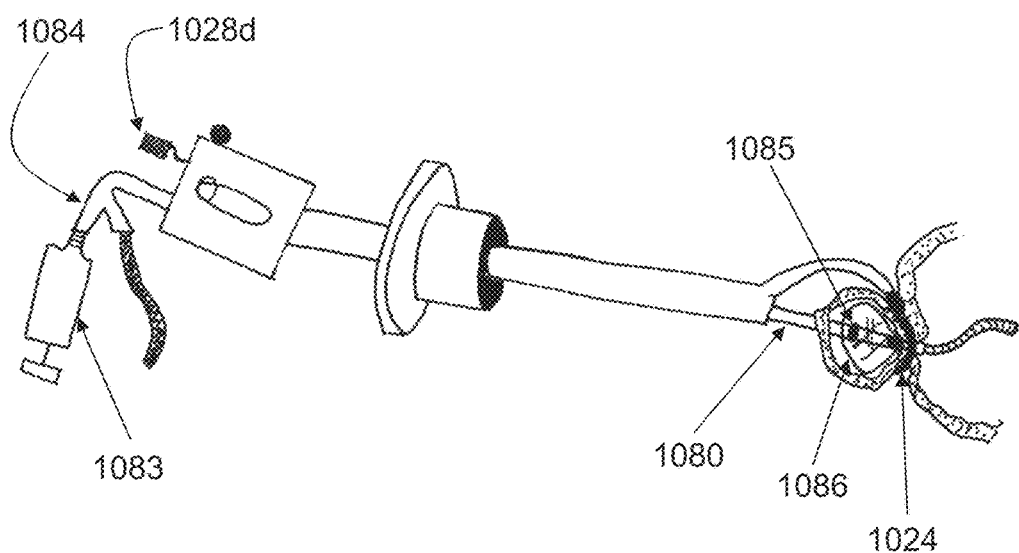

One variation of a method for ablating tissue from both the endocardial and epicardial surfaces is depicted in FIGS. 10A-10S. Access to the pericardial space may be attained in a variety of ways, some examples of which are shown in FIG. 10A. Additional examples are described in U.S. Provisional Patent Application No. 61/323,801 filed Apr. 13, 2010, which was previously incorporated by reference in its entirety, and U.S. application Ser. No. 13/086,328, filed on Apr. 13, 2011, entitled "Methods and Devices for Pericardial Access," which is hereby incorporated by reference in its entirety. As shown in FIG. 10A, a pericardial sac (1002) encases the heart and LAA (1000). Access to the LAA (1000) may be obtained from an initial site located in between ribs, or below the rib cage (1004). For example, the pericardium may be accessed through a right intercostal site (1006), a left intercostal site (1008), or a sub-thoracic site (1010), below the costal cartilages. The pericardium may also be accessed from below the diaphragm. In some procedures, the pericardium may be accessed from multiple sites, for example, from both right intercostal (1006) and left intercostal (1008) sites, the right intercostal (1006) and sub-thoracic (1010) sites, and the left intercostal (1008) and sub-thoracic (1010) sites. Depending on the location of the tissue targeted by one or more of the devices described herein, the access sites may be selected such that the target tissue region may be readily accessed. For example, an access site may be chosen for a particular target tissue region such that the tissue region may be reached by an ablation device without acute bending of the device, and/or excessive device maneuvering, manipulating, bending, torquing, etc. In some variations, an access site may be selected to reduce the path length between the initial entry site and the target tissue. Pericardial access may be monitored and/or confirmed using one or more imaging techniques, for example, fluoroscopy, echocardiography, and endoscopy. Once access to the pericardium has been established and confirmed, an incision or needle puncture may be made in the pericardial sac (1002), where an incision size may be based in part on the size of the device used for entry (e.g., guide wire, cannula, or any of the devices described here). In some variations, a small incision or puncture may be initially made and subsequently expanded by dilators to enable entry of other devices. Entry of any device(s) into the pericardial sac (1002) may also be monitored and confirmed using one or more imaging techniques as described above.

Various devices may be introduced into the epicardial space via an incision or puncture in the pericardium. FIG. 10B depicts a side view of the LAA (1000) and the left atrium (1003), encased by the epicardium (1001), myocardium (1005), and pericardial sac (1002). Within the cavity of the left atrium (1003), the bases of two pulmonary veins (1007*a*) and (1007*b*) may be seen. Devices may be advanced towards the LAA (1000) by inserting guide wire (1014) into a pericardial sac incision (1011). A guide cannula (1012) may be advanced over the guide wire (1014). A guide cannula (1012) and a guide wire (1014) may be steerable and/or pre-shaped according to a desired access route, for example, an access route that enables the penetration of LAA (1000) from between or under the rib cage. In some variations, one or more dilators may be used to insert and position the guide cannula (1012), after which the one or more dilators may be removed. In some variations, the guide wire (1014) may be removed after the guide cannula is positioned. Once in place, the guide cannula (1112) may provide navigational support and guidance to a LAA device, such as the LAA closure device (200) shown in FIG. 2. One method of localizing and stabilizing the LAA (1000) is depicted in FIG. 10C, where a LAA stabilizing device (1020) may be advanced via the guide cannula (1012) towards the LAA to contact the LAA. One variation of a LAA stabilizing device (1020) may contact the LAA (1000) by advancing a vacuum device (1022) through a looped closure assembly (1024). In this variation, the vacuum device (1022) may apply negative pressure which may draw a portion of the LAA (1000) into a collector, for example, one or more lumens, a basket, any woven semi-rigid structure, or a cup (1023), thereby securing the LAA. Some variations of the LAA stabilizing device (1020) may also comprise graspers. Graspers may be advanced through the looped closure assembly (1024) and such that they may secure the wall of the LAA (1000). Optionally, graspers may penetrate or pierce through the LAA wall. After the desired level of LAA stability is attained by activating the vacuum device (1022) and/or graspers, the looped closure assembly (1024) may be advanced over the LAA, and closed over the LAA. In some variations, the looped closure assembly may comprise a snare loop and a suture loop releasably coupled to the snare loop, where the snare loop and the suture loop may be separately tightened, and/or tightened in a coordinated fashion. The suture loop may be released and/or disengaged from the snare loop after the suture loop has been tightened over the neck of left atrial appendage. In some variations, the suture loop may be released from the LAA stabilizing device (1020) after being closed and locked around the LAA. In some variations, the looped closure assembly (1024) may be closed to secure/locate the LAA, and then may be opened to allow devices to be advanced therethrough, and then closed to secure/locate the LAA. The opening and closing of the looped closure assembly (1024) may help to maintain hemostasis during the procedure. Examples of a looped closure assembly and other stabilization and closure devices that may be used with the LAA stabilization device (1020), along with other devices and methods for ensnaring a LAA, are described in U.S. patent application Ser. No. 12/055,213 (published as U.S. 2008/0243183 A1), which was previously incorporated herein by reference in its entirety.

FIG. 10D illustrates the proximal portion of the LAA stabilizing device (1020), which may comprise one or more ports, for example, a vacuum source port (1021) and a needle port (1030), and actuators (1028a) and (1028b). The vacuum source port (1021) and the needle port (1030) may comprise valves to regulate the passage of devices or fluids through the ports. Actuators (1028a) and (1028b) may activate the looped closure assembly (1024) and the vacuum device (1022), respectively. While the vacuum device (1022) is activated (e.g. applying negative or positive pressure), an access needle (1032) may be inserted into the needle port (1030). The LAA access device (300) as described above and depicted in FIG. 3 may be used here. As seen in FIG. 10E, an access needle (1032) may be advanced through the needle port (1030), through the LAA stabilizing device, and through the vacuum device (1022) to puncture and enter the LAA (1000). Optionally, before or after the LAA is punctured by the access needle, looped closure assembly (1024) may be adjusted, e.g. closed or opened, to control bleeding and/or provide endocardial access to devices. Other hemostatic devices (e.g., valves, plugs, etc.) may be used at or near the needle puncture to control and/or limit bleeding. Once access needle (1032) has penetrated the LAA, a standard guide wire (1031) may be advanced into the LAA, and the access needle may be withdrawn. In some variations, the access needle (1032) may remain in the LAA and left atrium, to maintain the puncture in the LAA and/or left atrium. After the guide wire (1031) is inserted into the LAA and/or left atrium, the vacuum device (1022) may be removed, as shown in FIG. 10F.

Optionally, LAA stabilizing devices may comprise additional LAA attachment features that may further secure the LAA after it has been stabilized, for example, as depicted in FIG. 10G. As shown there, a distal segment of a LAA stabilizing device (1020') may comprise a looped closure assembly (1024') and apertures (1025) through which positive or negative pressure may be applied. Negative pressure may be applied through apertures (1025) to draw the LAA towards the device, further securing and stabilizing it. In this variation, negative pressure may be applied to apertures (1025) after looped closure assembly (1024') has effectively encircled the LAA, which may help ensure that the LAA is fully stabilized prior to the insertion of access needle (1032). The position of looped closure assembly (1024') after it has encircled the LAA may be adjusted by applying positive pressure to the apertures (to release the LAA) and negative pressure (to secure the LAA). Alternatively, a distal segment (1019) of the LAA stabilizing device (1020') may be adapted to help looped closure assembly (1024') to engage and encircle the LAA. For example, the distal segment (1019) may be advanced towards the LAA. The looped closure assembly (1024') may then engage a tip portion of the LAA, after which negative pressure is applied to the distal-most aperture, while the remaining apertures remain pressure-neutral. Then, the distal segment (1019) may be advanced towards the LAA, and then the negative pressure in the distal-most aperture is released, immediately followed by the application of negative pressure on the second distal-most aperture. These steps may be repeated, where distal segment (1019) may effectively advance in a step-wise fashion across the LAA by sequentially applying and then releasing negative pressure on each of the apertures (starting from the distal-most aperture and moving proximally), until the looped closure assembly (1024') reaches the ostium of the LAA. Once the looped closure assembly (1024') reaches the ostium of the LAA, it may be cinched to secure the LAA, and optionally, negative pressure may be applied on all apertures (1025) to further secure the LAA.

Various devices may be advanced over the guide wire (1031) to access the internal portion of LAA (1000) and left atrium (1003). The guide wire (1031) may be navigated and controlled by actuator (1028c). Ablation devices may be advanced over the guide wire (1031) to ablate asynchronous tissue for the treatment of atrial fibrillation. FIG. 10H depicts one variation of an endocardial ablation device (1040) as it is advanced over guide wire (1031), through the wall of the LAA and into the left atrium. For example, the endocardial ablation device (400) as described above and depicted in FIG. 4 may be used here. In some variations, an endocardial ablation device may be advanced through the LAA to access the left pulmonary veins. Optionally, an endocardial ablation device may be advanced via an intravascular antegrade transseptal approach to access the right pulmonary veins. As described previously, an ablation device such as the endocardial ablation device (1040) may utilize any tissue-affecting mechanism to create a lesion in the target tissue. Examples of tissue-affecting mechanisms include cryo-ablation, radiofrequency (RF), ultrasound, microwave, laser, any suitable type of photo-ablation using light-activated agents that may trigger cellular apoptosis, heat, localized delivery of chemical or biological agents, and the like. In some variations of an endocardial ablation device, a source (1044) may be a reservoir of one or more cryogenic, chemical, or biological agents, and/or may be an energy source (e.g., laser light source, pulse generator, ultrasonic source, etc.) and may be located a proximal portion of the ablation device (1040). A conductive structure (1041) may provide a conduit for conveying the ablation energy from the source (1044) to the distal portion of ablation device (1040). For instance, the conductive structure (1041) may be a wire, fiber optic cable, lumen, channel, microfluidic channel, etc.

Ablation array (1042) of the endocardial ablation device (1040) may be integrally formed with the proximal portion of the ablation device (1040), or may be attached via an articulating hinge (1043). In some variations, an ablation array may comprise ablation elements and/or magnetic elements, as previously described above. The endocardial ablation device (1040) may have a first delivery configuration, where the ablation array (1042) has a narrow profile (as shown in FIG. 10H), and a second deployed configuration, where the ablation array (1042) assumes a wider profile (as shown in FIG. 10I). In the delivery configuration, the ablation array (1042) may have a substantially straight linear geometry. In the deployed configuration, the ablation array (1042) may be expanded to have a curved shape, such as a semi-circular shape, to circumscribe the base of pulmonary vein (1007b). The deployed configuration of the ablation array may have any shape that may be configured to accommodate the anatomy of the target tissue to achieve a desired ablation profile. For example, the ablation array may have any of the shapes previously described and depicted in FIGS. 6A-6F.

Once the ablation array (1042) of the endocardial ablation device is positioned at a region of tissue in the left atrium, e.g. around the base of pulmonary vein (1007b), an epicardial ablation device may be aligned and placed on the epicardial surface of the atrium (1003). A second guide cannula (1052) may be inserted in any of the access sites previously described and depicted in FIG. 10A, and may use the same or different access point from the first guide cannula (1012). The guide cannula (1052) may be advanced to the pericardial space as described previously, and once positioned and stabilized, the guide wire (1050) may be advanced through guide cannula (1052) to track around a target tissue region, e.g. the tissue region directly across where the endocardial ablation array (1042) is positioned, as shown in FIG. 10J. Guide cannula (1052) may have one or more curves, and may vary in length, as suitable for the access site(s) used. Guide wire (1050) may comprise a magnetic component at its distal tip (not shown). The magnetic component may be of any suitable type, size, and shape, for example, the magnet may be a rare-earth, electro-activated, or a multi-alloy (e.g. iron, boron, neodymium) magnet. A guide wire with a magnetic distal tip may facilitate the navigation of the guide wire to the magnetic component(s) of the positioned endocardial ablation device. The epicardial ablation device may be navigated over the guide wire (1050) and through the guide cannula (1052) to the target site, e.g. at or around pulmonary vein (1017b) which is directly across from the base (1007b). In some variations, the epicardial ablation device (500) as described above and depicted in FIG. 5, may be used here. As with the endocardial ablation device, an ablation array (1062) may be attached to the distal portion of the epicardial ablation device (1060), as shown in FIGS. 10K and 10L. In some variations, an ablation array may comprise ablation elements and/or magnetic elements, as previously described with respect to ablation array (508). Similar to the endocardial ablation device (1040), the epicardial ablation device (1060) may have a delivery configuration that has a substantially narrow profile, as seen in FIG. 10K, and a second deployed configuration, where ablation array (1062) assumes a wider profile, as seen in FIG. 10L. In the delivery configuration, the ablation array (1062) may have a substantially straight linear geometry. In the deployed configuration, the ablation array (1062) may have a curved shape, such as a semi-circular shape to circumscribe the trunk of the pulmonary vein (1017b), however, may be any shape to accommodate the anatomy of the target tissue to achieve a desired ablation profile. In the variation of method described here, the tissue around the pulmonary veins may be ablated both epicardially and endocardially. According to this variation, the shape of the deployed configuration of the epicardial ablation device corresponds with the shape of the deployed configuration of the endocardial ablation device, e.g., mirror-symmetric. Once the epicardial ablation device has assumed its deployed configuration, the guide wire (1050) may be withdrawn.

Endocardial and epicardial ablation devices may comprise alignment features, which may help ensure a particular orientation of one ablation device with respect to another, and may also create an intimate contact between the ablation devices and the tissue to be ablated. In the variation of the ablation devices described here, the attractive forces between the magnets on one or both of the epicardial and endocardial ablation devices may align the devices to one another. FIGS. 10M and 10N show enlarged cross-sectional views of the endocardial ablation array (1042) and the epicardial ablation array (1062) positioned across each other, where the endocardial ablation array may circumscribe the base of a pulmonary vein within the cavity of the left atrium, and the epicardial ablation array may circumscribe the trunk of the same pulmonary vein on the outer surface of the left atrium. As shown in FIG. 10M, the epicardial ablation device may be advanced such that the epicardial ablation array (1062) is positioned approximately opposite the endocardial ablation array (1042), i.e. around the pulmonary vein (1017b) of the left atrium (1003), such as a left pulmonary vein. Endocardial magnetic components (1045) and epicardial magnetic components (1065) may attract each other, drawing the ablation arrays towards each other to form a stable contact with the wall of the left atrium, as shown in FIG. 10N. The magnetic attraction between the ablation arrays may compress the wall of the left atrium against the ablation arrays, which may improve the efficacy of lesion formation in the atrial wall, which may reduce the magnitude of the energy (or the quantity of fluid) needed to ablate the tissue between the ablation arrays. In some cases, arranging the ablation arrays on both sides of the atrial wall may help form a transmural lesion that spans the entire thickness of the wall between the arrays.

While the devices and methods above are directed towards ablating tissue endocardially and epicardially to form an ablation pattern that circumscribes the base of a pulmonary vein, other ablation patterns and profiles may be also be used for the treatment of atrial fibrillation. Examples of other ablation patterns are schematically illustrated in FIGS. 10O-10P. A cutaway of left atrium (1003) and LAA (1000) reveals the four pulmonary veins (1007*a*), (1007*b*), (1007*c*), and (1007*d*). FIG. 10O depicts one variation of an ablation pattern (1070) where each of the pulmonary veins are individually circumscribed. FIG. 10P depicts another ablation pattern (1071) where pairs of pulmonary veins are circumscribed, i.e., (1007*a*) and (1007*c*) are circumscribed by one lesion, and (1007*b*) and (1007*d*) are circumscribed by another lesion. Different pairs of pulmonary veins may be circumscribed together, depending on the profile of electrical isolation that is needed. The shape (e.g., number of curves, radii of curves, etc.) of the endocardial and epicardial ablation arrays may be adjusted such that ablation pattern (1071) may be obtained. For example, the endocardial and epicardial ablation arrays may have an elongated elliptical shape (e.g., where the length is substantially greater than the width) to attain the ablation pattern of FIG. 10P. FIG. 10Q depicts yet another ablation pattern (1072) where all pulmonary veins are circumscribed by a single lesion. In this variation, the endocardial and epicardial ablation arrays may be sized and shaped to circumscribe all of the pulmonary veins. In addition to the lesion patterns described in FIGS. 10O-10Q for pulmonary vein isolation, the endocardial and/or epicardial ablation arrays may be used to create linear lesions through tissue of the left atrium (LA) including: the LA roof line (e.g., along the connection between the right superior pulmonary vein (1007*b*) and the left superior pulmonary vein (1007*a*)), the mitral valve isthmis line (e.g., along the connection between left inferior pulmonary vein (1007*c*) to the mitral valve annulus (1009)), and the posterior LA line (e.g., along the connection between both sets of pulmonary veins across the posterior LA). Other ablation patterns and lesion geometries may be used to obtain a desired degree and profile of electrical isolation. While these ablation patterns have been described in the context of simultaneous ablation of tissue from both the endocardial and epicardial surfaces, it should be understood that these ablation patterns may also be attained by ablating either the endocardial surface or the epicardial surface. In general, any appropriate ablation profile may be achieved for any target tissue by adjusting the size and shape of the ablation arrays on the ablation devices. For example, to ablate a larger volume and/or area of tissue, a smaller ablation array (e.g. an array that ablates a volume of tissue smaller than the desired ablation pattern) may apply the ablation energy multiple times at different tissue regions. Alternatively, a larger volume and/or area of tissue may be ablated by an ablation array that is comparably sized with the desired ablation volume/area, and may be shaped according to the target tissue. In this variation, the ablation energy may only need to be applied once. While the ablation regions around the pulmonary veins have been described, additional ablation targets for the treatment of atrial fibrillation may include other anatomical regions. For example, other tissue regions that may be suitable non-pulmonary vein ablation targets may include the superior vena cava (SVC), LA posterior wall, crista terminalis, coronary sinus (CS), ligament of Marshall, intrarterial septum, and/or any other tissue regions that may trigger atrial fibrillation.

During and/or after tissue ablation, the progress of the ablation and the lesion size may be monitored and verified. Lesion formation may be monitored functionally and/or anatomically. For example, lesion formation may be monitored by heat transfer measurements, electrocardiography mapping, ejection fraction, local electrogram amplitude reduction and mapping, impedance tomography, ultrasound, fluoroscopy, and other suitable functional metrics or imaging modalities. Based on these measurements and images, the rate, size, and other characteristics of lesion formation may be modified, e.g., by adjusting power and wavelength of the ablation energy, to achieve the desired degree of electrical isolation. In some variations, lesion formation may be measured in terms of the change in the tissue temperature across the thickness of the tissue. For example, endocardial and epicardial ablation arrays may each comprise temperature sensors as previously described may be pressed into the atrial wall tissue to measure the temperature on either side of the atrial wall. In some variations, either the endocardial or the epicardial ablation array has a temperature probe, so that the heat transfer front from the other ablation array may be measured. The temperature probe may also be a separate device that is advanced to the desire target tissue region.

Once the desired portion of tissue has been ablated (e.g., verified that a lesion of a desired size and shape has been formed), the ablation devices and positioning catheters may be removed. The alignment feature that couples the endocardial ablation array (1042) with the epicardial ablation array (1062) may be deactivated, either mechanically (e.g., by applying a force stronger than, and opposite to, the coupling force) or electrically (e.g., by turning off the electro-magnet). The endocardial ablation device (1040) and the epicardial ablation device (1060) may be removed sequentially or simultaneously, as may be appropriate. The endocardial guide wire (1031) may be kept in place to facilitate the navigation of any additional devices to the left atrium and/or LAA, however, in other variations, the guide wire (1031) may be removed.

Optionally, a method for the electrical isolation of tissue in the LAA and/or left atrium may comprise a step that electrically isolates the LAA. FIG. 10R depicts an occlusion device (1080) that may be advanced over the guide wire (1031) via a guide wire port (1082) and through a working channel of the LAA stabilizing device (1020) to access the internal portion of the LAA (1000). For example, the occlusion device (700) as described previously and depicted in FIG. 7 may be used here. In some variations, an occlusion device may be configured to deliver contrast and/or therapeutic agents through the guide wire port or an infusion lumen that may extend along the occlusion device from the proximal portion to distal portion. The looped closure assembly (1024) may remain in a closed configuration to stabilize and localize the LAA. The distal portion of the occlusion device (1080) may comprise an expandable member (1086) which may have a collapsed delivery configuration (shown in FIG. 10R) and an expanded deployed configuration (shown in FIG. 10S). Optionally, the distal portion of the occlusion device (1080) may also comprise radioopaque and/or echogenic markers (1085) so that the position of the occlusion device may be detected by imaging. Some variations of an occlusion device may comprise side apertures that provide for the infusion of a contrast agent to enhance visualization of the occlusion device, or the infusion of other agents, including therapeutic agents such as heparin or other anticoagulants, saline, etc. The expandable member (1086) may be expanded by introducing a fluid, e.g. liquid or gas, via a fluid lumen (1084), from a pressurized fluid reservoir (1083). Alternatively or additionally, in other variations of an occlusion device, the expandable member may be mechanically dilated, e.g., by actuating struts. During or after the expansion of the expandable member (1086), the looped closure assembly (1024) may be further tightened around the LAA by actuating tab (1028*d*). Tightening the looped closure assembly (1024) around the neck of LAA (1000) may block the exchange of any substances between the LAA cavity and the left atrial cavity. In some variations, tightening the looped closure assembly may sever the LAA entirely, such that it is excluded from the left atrium. For example, a releasable suture loop and a snare loop of the looped closure assembly may be tightened to exclude the LAA, and the snare loop may be proximally withdrawn from the suture loop, e.g., after the suture loop is released from the looped closure assembly by further pulling on tab (1028d). The LAA may be extracted from the body by any suitable method, for example, by using negative pressure to secure the LAA into a collector or tubular member, which is then retracted out of the body. Optionally, a debrider may be used to break the excised LAA into smaller portions prior to extraction, which may be suitable for use with a minimally invasive procedure. In some variations, a chemical or enzyme agent may used prior to extraction to break down or soften the LAA for removal.

As described above, the neck of LAA may be encircled and cinched by a suture snare, however, other mechanisms may be included to close and/or occlude the LAA cavity. As shown in FIGS. 11A-11C, a clip (1100) may be used to close the LAA. Clip (1100) may be advanced through a guide cannula and encircled around a LAA or LAA neck. Subsequently, a mandrel (1104) may be advanced through the guide cannula in the direction of arrow (1006) to urge a collet (1102) onto a clip neck (1103), as shown in FIG. 11A. FIG. 11B depicts that the collet (1102) may continue to be urged in the direction of arrow (1108), until it is completely secured onto the clip (1100), and the LAA enclosed by the clip is tightened. The collet (1102) may be engaged onto the clip (1100) by snap-fit, press-fit, or friction-fit. In some variations, alternate closure mechanisms may be used, such as a cable tie with a ratchet mechanism, a Nitinol cable or loop, and the like. The clip (1100) may be made of shape memory material, such as a nickel titanium alloy, where in the unconstrained configuration, the neck (1103) naturally springs open, and the spring force engages and secures collet (1102). After the collet has secured and closed the clip, the mandrel (1104) may be removed.

A variety of expandable members may be used to occlude and/or exclude the LAA. For example, an inflatable expandable member, such as a balloon similar to the expandable member (1086), may be used to occupy the LAA cavity, preventing the escape of, or continuing development of, thrombi in the LAA. In another variation shown in FIG. 12A, expandable member (1200) in LAA (1000) may be filled with a hardening material (1202), such as thermal polymers, hydrogels, epoxy, and any suitable hardening materials. The hardening material may initially be a liquid or gel that may be delivered through a lumen (1204) in the occlusion device, and may solidify after being deposited in the expandable member (1200) within the LAA (1000). Alternatively or additionally, an expandable member may be self-expanding, as depicted in FIG. 12B. As shown there, an expandable element (1210) may be an ostial occluder that automatically expands once urged by mandrel (1212) into the LAA cavity. The expandable member may be made of one or more polymeric materials, for instance, polypropylene, polyurethane, polyethylene, polytetrafluoroethylene, and in some variations, may alternatively or additionally include one or more metal alloys such as nitinol, stainless steel, etc., or any shape-memory material. A self-expanding expandable member may be an enclosed structure, such as a balloon, or a mesh-like structure. Mechanisms of self-expansion include shape-memory, thermal expansion, spring-action, and the like.

Endocardial Ablation

Figure 13A:
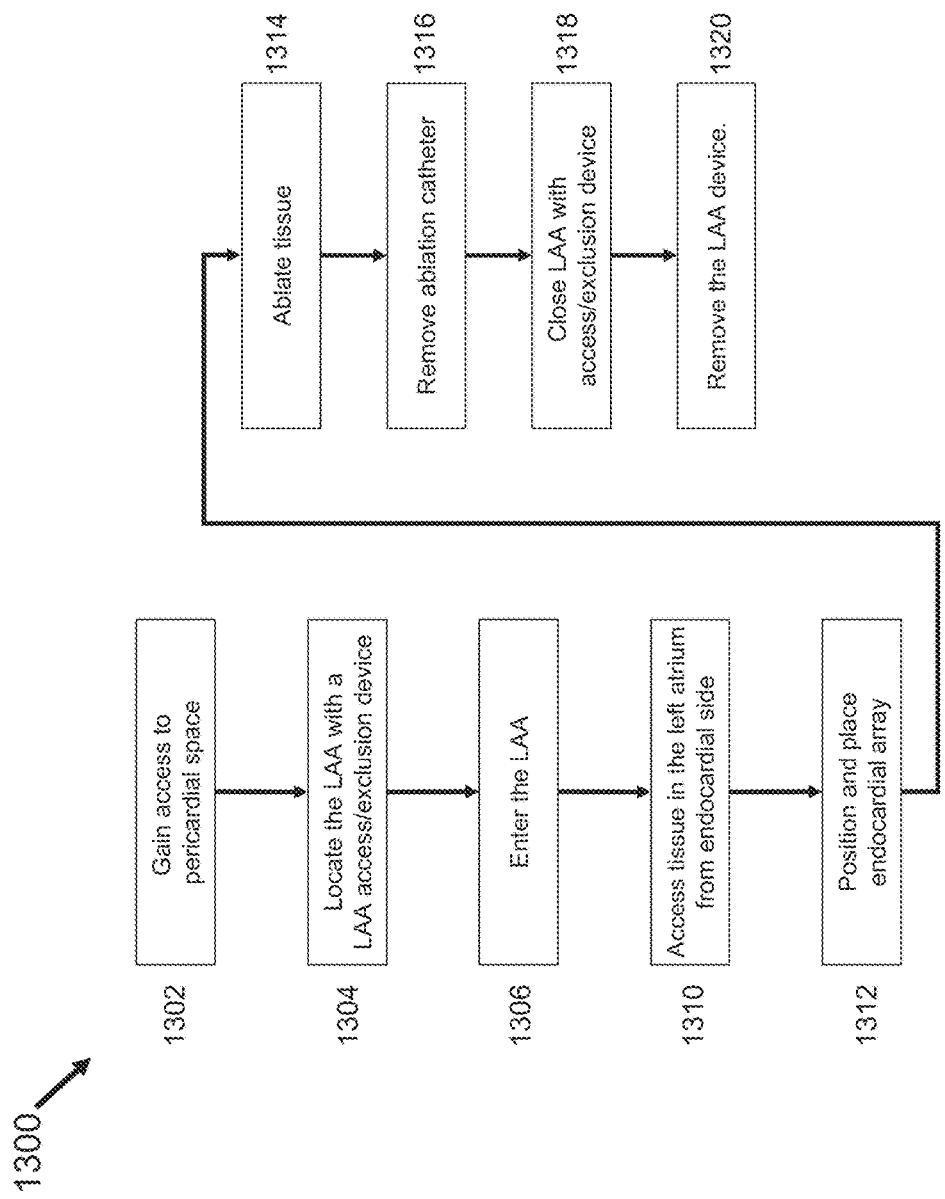
FIG. 13A depicts a flowchart that represents one variation of a method for ablating atrial wall tissue from an endocardial surface.

While some methods for the treatment of atrial fibrillation may ablate tissue in the left atrium both endocardially and epicardially, other variations of ablating tissue in the left atrium, and subsequently occluding and/or excising the LAA may be used. One example of a method that ablates an endocardial surface of a left atrium is shown in FIG. 13A. Method (1300) may be used to ablate tissue from an endocardial surface using surgical, intravascular and/or other minimally invasive techniques (e.g., percutaneous, small incisions or ports), and may be used in stopped heart or beating heart procedures. The method (1300) may comprise accessing the pericardial space (1302). Optionally, a device may be used to locate and stabilize the LAA (1304), for example, the closure device (200) as described above and shown in FIG. 2. Once access into the pericardial space and to the LAA has been established, a device may enter the LAA (1306) by creating a puncture in the LAA. Access to various tissue regions in the left atrium (e.g., atrial wall tissue, tissue at or around the base of the pulmonary veins, tissue within the pulmonary veins, etc.) from an endocardial side may be established (1310). An endocardial ablation array may be positioned and placed along an endocardial surface of the left atrium (1312). For example, the endocardial ablation array may circumscribe the pulmonary veins to obtain a particular ablation pattern. The endocardial ablation array may then be activated (1314). After the desired tissue has been ablated (e.g., atrial wall tissue, tissue at or around the base of the pulmonary veins, tissue within the pulmonary veins, etc.), the ablation devices may be removed (1316), and the LAA may be occluded, closed, and/or removed (1318). Once the LAA has been decoupled from the remainder of the left atrium, all devices may be retracted from the surgical site (1320). In some variations of methods for ablating tissue in the left atrium, the endocardial ablation device may be advanced intravascularly (e.g., from a retrograde approach, or an antegrade transseptal approach, etc.). Access to the left atrium may be accessed by any method or approach as may be suitable for contacting the targeted tissue region.

Figure 13B:
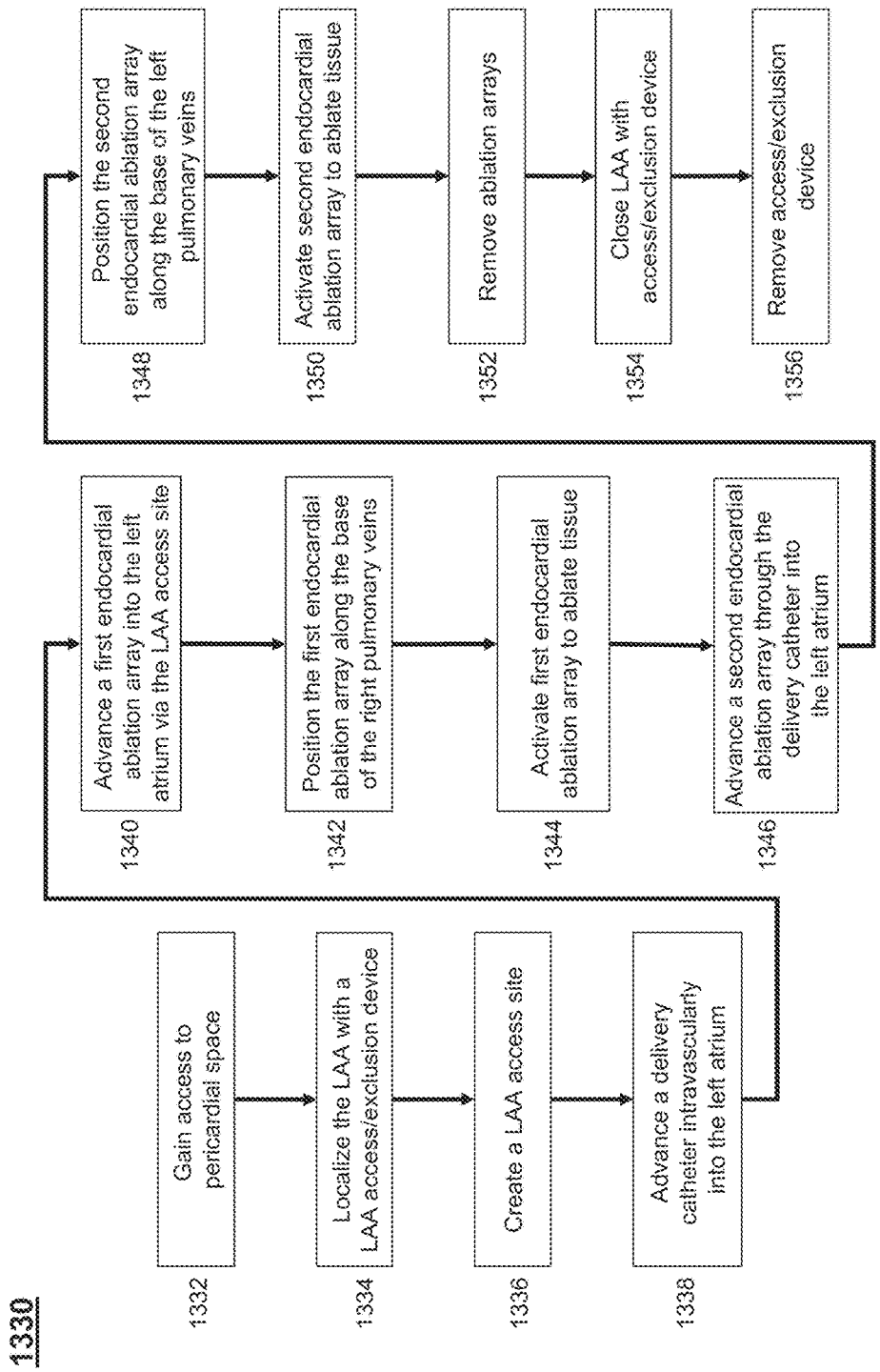
FIG. 13B depicts a flowchart that represents another variation of a method for ablating tissue from an endocardial surface.

While the method described above uses one endocardial ablation array for ablating the tissue of the left atrium from an endocardial side, other methods may use two endocardial ablation arrays. One example of a method that uses two endocardial ablation arrays for ablating atrial tissue on an endocardial side is depicted in FIG. 13B. As previously described, an access pathway is created to the pericardial space (1332). A LAA access/exclusion device may be used to locate and stabilize the LAA (1334). Once access into the pericardial space and to the LAA has been established, a device may be used to create a puncture in the LAA (1336), which may allow a device to access the left atrium through the LAA. An intravascular pathway to the left atrium may also be attained by advancing a delivery catheter through the vasculature into the left atrium (1338), e.g., using a retrograde or an antegrade transseptal approach. Once the intravascular and/or LAA access pathways into the left atrium have been established, a first endocardial ablation array may be advanced into the left atrium through the LAA (1340). The first endocardial ablation array may be positioned at any desired tissue region (e.g., atrial wall tissue, tissue at or around the base of the pulmonary veins, tissue within the pulmonary veins, etc.), such as along tissue at or around the bases of the right pulmonary veins (1342). The first endocardial ablation array may be activated to ablate tissue (1344). A second endocardial ablation array may be advanced intravascularly through the delivery catheter into the left atrium (1346). The second endocardial ablation array may be positioned along tissue at or around the bases of the left pulmonary veins (1348). The second endocardial ablation array may be activated to ablate tissue (1350). The positioning and activation of the first and second endocardial ablation arrays may be repeated as desired. After ablating the desired tissue regions, the ablation arrays may be removed (1352). The LAA may be closed with the access/exclusion device (1354), and then the access/exclusion device may be removed (1356).

While the steps of the method (1330) have been described in the sequence as depicted in FIG. 13B, it should be understood that the steps may take place in an alternate sequence, and certain steps may take place substantially simultaneously. For example, the delivery catheter may be advanced intravascularly into the left atrium (1338) before or after the LAA access site is created (1336). In some variations, the second ablation array may be advanced through the delivery catheter into the left atrium (1346) before the first endocardial ablation array is advanced through the LAA into the left atrium. The activation of the ablation arrays may occur sequentially or simultaneously. For example, the first or second endocardial ablation array may be activated simultaneously or sequentially.

Figure 14A:
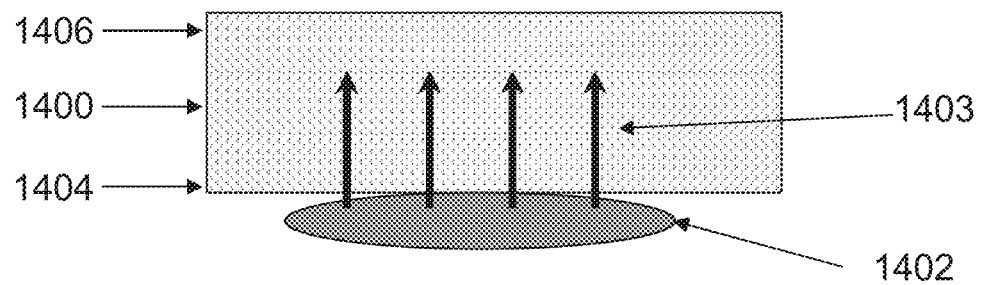
FIGS. 14A and 14B depict ablation patterns that may be formed by endocardial ablation of atrial wall tissue.
Figure 14B:
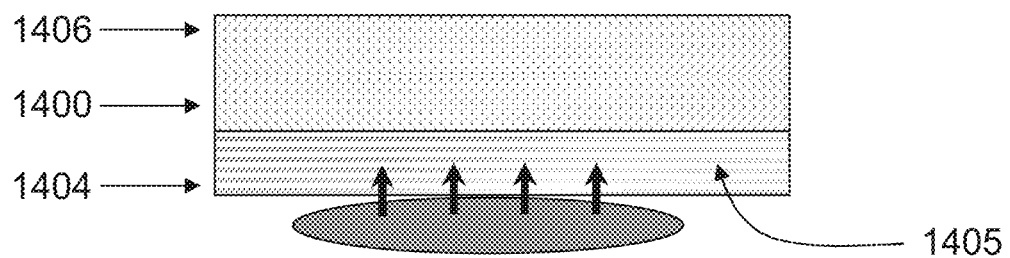

Examples of ablation patterns that may be formed by endocardial ablation method (1300) are shown in FIGS. 14A and 14B. Ablation array (1402) is positioned against atrial wall (1400) on the endocardial side (1404). The ablation energy (1403) may be any mechanism of tissue ablation, as described previously. As depicted in FIG. 14B, the portion of the atrial wall (1405) that is closest to ablation array may be ablated relatively quickly, while the portion of the atrial wall further from the ablation array, e.g. tissue near the epicardial side (1406), may not be ablated. To ablate tissue furthest from the ablation array (1402), a longer exposure to a greater quantity of ablation energy (1403) may be needed. For example, to ablate tissue closest to the epicardial side (1406), radiofrequency or cryogenic delivery may need to be increased, and laser energy and heat may need to be more intense. Additionally or alternatively, the ablation of tissue further from the ablation array (1402) may involve increasing the exposure time of tissue (1400) to the ablation energy (1403). The ablation depth achieved an ablation array may be regulated by adjusting more of the above-described factors, as may be desirable. For example, the depth of tissue that is ablated may be 5%, 10%, 25%, 40%, 50%, 60%, 75%, 80%, 95%, etc. of the thickness of the tissue wall. In some variations, closed system or open system irrigation may be included during the delivery of the energy source to regulate the ablation of tissue adjacent to the ablation array. As described previously a temperature probe may be used to measure temperature changes that may arise from tissue ablation, which may help to regulate the amount of ablation applied to a tissue region.

Epicardial Ablation

Figure 15:
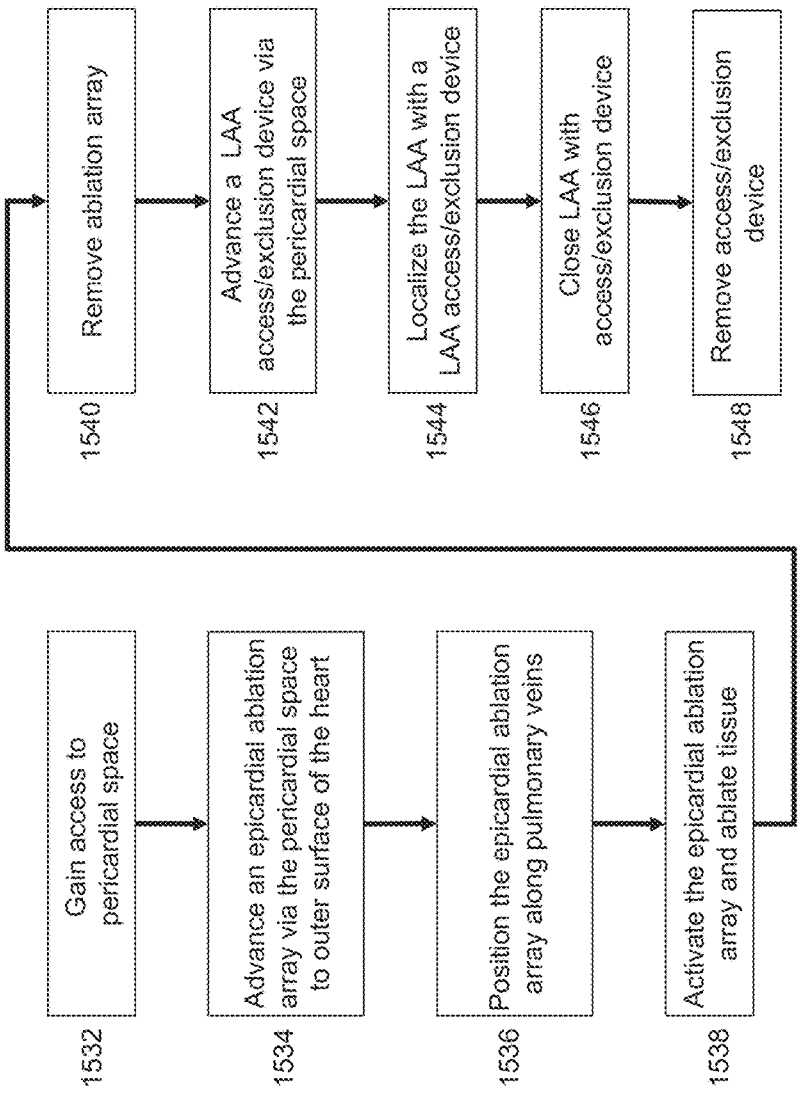
FIG. 15 depicts a flowchart that represents one variation of a method for ablating atrial wall tissue from an epicardial surface, comprising a procedure to close, and/or occlude, and/or remove the left atrial appendage.

Ablation of tissue of the LAA and left atrium may be achieved by epicardial ablation. An example of a method (1500) for epicardial ablation is shown in FIG. 15. Method (1500) may be used to ablate tissue using surgical techniques or intravascular techniques, and may be used in stopped heart or beating heart procedures. As previously described, an access pathway may be created to the pericardial space (1532). An epicardial ablation array may be advanced via the pericardial space to the outer surface of the heart (1534). The epicardial ablation array may be positioned along tissue at or near the trunk of the pulmonary veins (1536). The epicardial ablation array may be activated to ablate tissue (1538). Optionally, the epicardial ablation array may be positioned and activated at different locations on the outer surface of the heart, as may be desirable. After ablating the desired tissue regions, the ablation arrays may be removed (1540). Optionally, a LAA access/exclusion device may be advanced to the LAA via the pericardial space (1542). The access/exclusion device may be used to locate and stabilize the LAA (1544). The LAA may be occluded or excised by the access/exclusion device (1546), and then the access/exclusion device may be removed (1548). Decoupling the LAA from the remainder of the left atrium may help reduce the risk of thrombosis or stroke that may occur in atrial fibrillation.

FIGS. 19A-19F depict another variation of an access device and method that may be used to position a device on an epicardial surface of the heart, e.g., around a tissue structure such as a blood vessel or the LAA. Access device (1900) or a similar device may be used to place a guide element (1902) or other device around a tissue structure (1904), such as a blood vessel or the left atrial appendage. As shown there, access device (1900) may comprise a cannula (1906), a first guide (1908), and a second guide (1910). First (1908) and second (1910) guides each may comprise a lumen (1912) extending therethrough, and may further comprise a magnetic alignment element (1914) at a distal end thereof. First (1908) and second (1910) guides may be at least partially housed inside cannula (1906), and may be configured to be advanced out of a distal end of the cannula (1906). In some variations, first (1908) and second (1910) guides may be housed in a single lumen (not shown) of cannula (1906). In other variations, first (1908) and second (1910) guides may be housed in separate lumens (e.g., a first lumen and a second lumen, respectively). It should be appreciated that cannula (1906) may comprise any suitable number of lumens (e.g., one, two, or three or more).

Figure 19A:
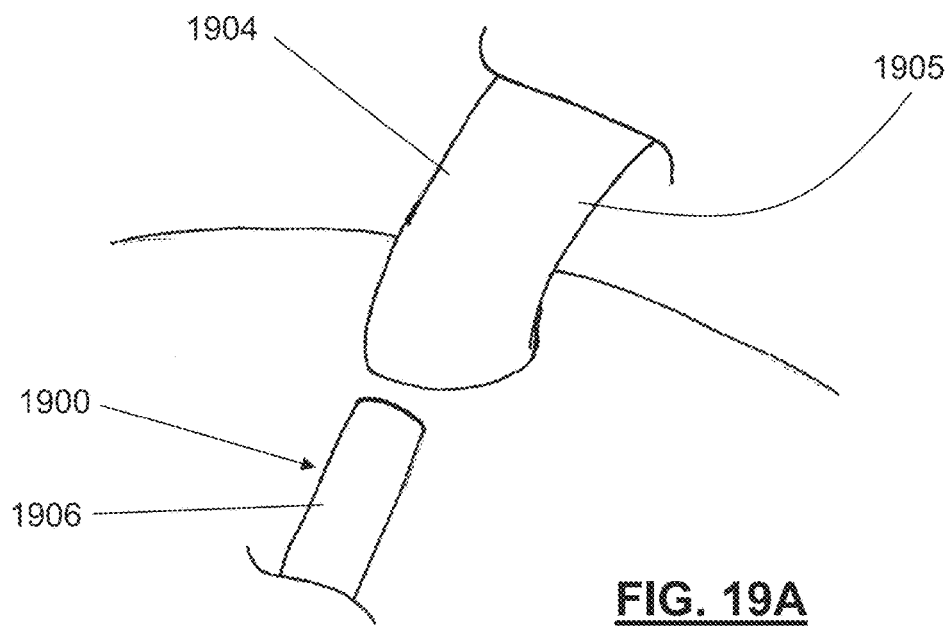
FIGS. 19A-19F another example of devices and methods that may be used to place a device at or around a tissue structure.

Returning to the figures, cannula (1906) may be advanced to tissue structure (1904), as shown in FIG. 19A. In some variations, the tissue structure (1904) may be the right atrial appendage. Cannula (1906) may be advanced in any suitable manner. In some variations, cannula (1906) may be advanced over a guidewire (e.g., via one or more lumens of the cannula (1906). Additionally or alternatively, one or more portions of the cannula (1906) may be steerable. While shown in FIGS. 19A-19F as being a blood vessel (1905), tissue structure (1904) may be any suitable anatomical structure. In some variations, tissue structure (1904) may be the left atrial appendage.

Figure 19B:
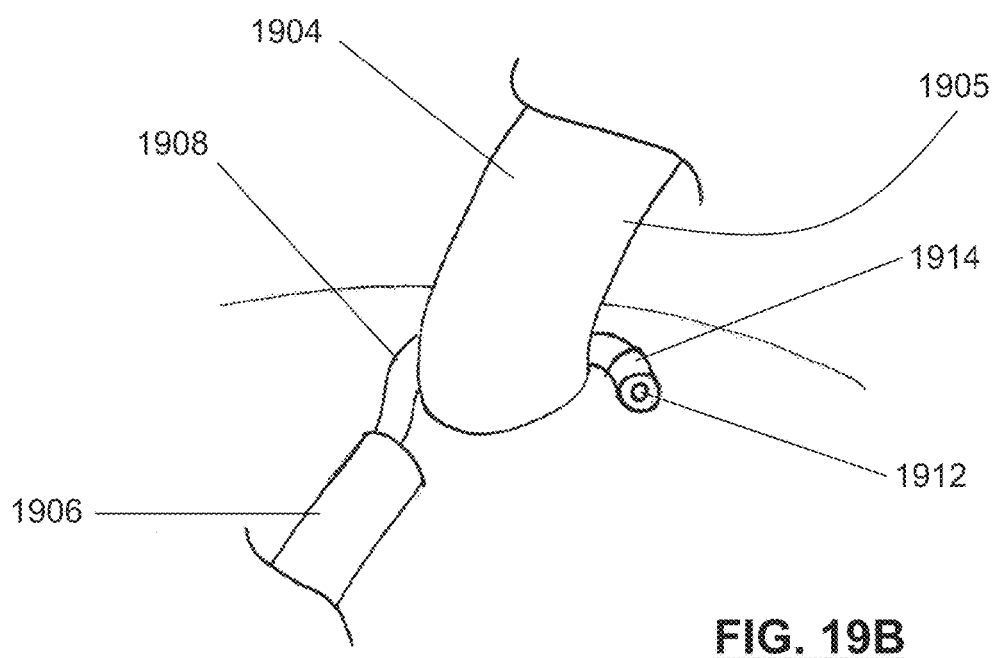

Once cannula (1906) is positioned at or near the tissue structure (1904), first guide (1908) may be advanced out of the distal end of cannula (1906), as shown in FIG. 19B. As first guide (1908) is advanced out of the distal end of cannula (1906), it may take on a curved configuration. In some variations, the first guide (1908) has a pre-shaped curved configuration, which may be constrained when it is housed within cannula (1906). In other variations, the first guide (1908) may be steered or otherwise actuated to take on the curved configuration. The first guide (1908) may be advanced such that a distal portion of the guide (1908) curves at least partially around the tissue structure (1904), as depicted in FIG. 19B.

Figure 19C:
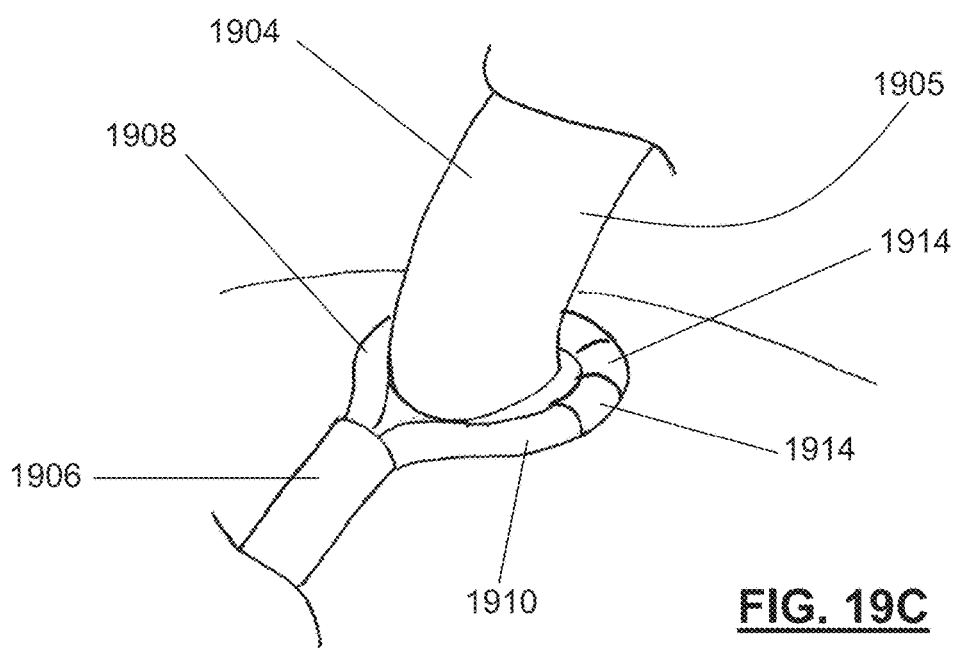

The second guide (1910) may then be advanced from the distal end of cannula (1906), as depicted in FIG. 19C. As shown there, the second guide (1910) may be advanced toward and may engage the first guide (1908). For example, in variations where the first (1908) and second (1910) guides each comprise a magnetic alignment element (1914), the magnetic alignment elements (1914) of the first (1908) and second (1910) guides may attract each other and hold the distal ends of the two guides in place relative to each other.

In some variations, the distal ends of first (1908) and second (1910) guides may be positioned such that the lumens (1912) of the two guides are aligned. In some of these variations, the magnetic alignment elements (1914) of each of the first (1908) and second (1910) guides may hold the lumens (1912) of the two guides in alignment.

Figure 19D:
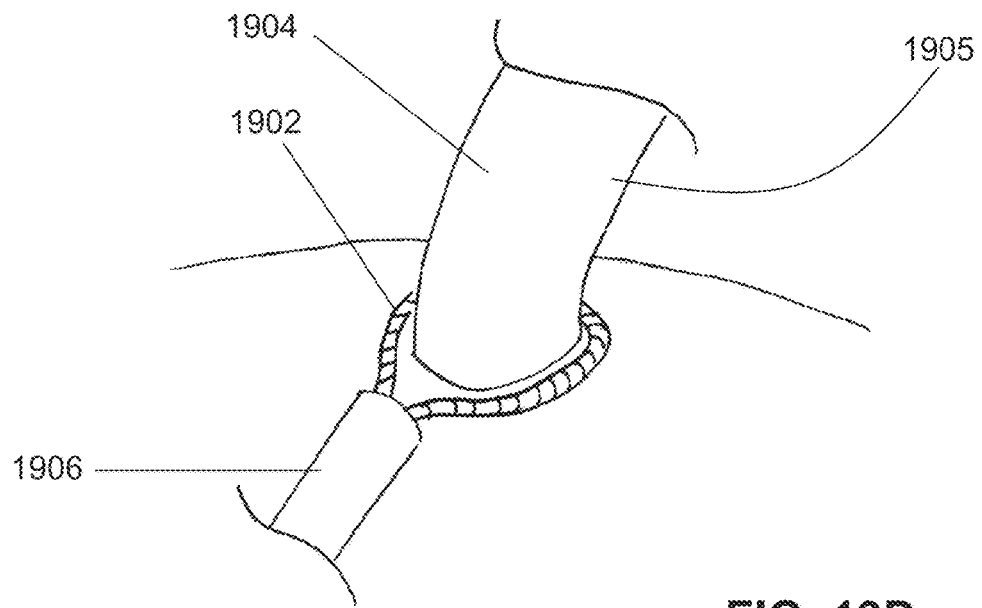

Once the lumens (1912) of the first (1908) and second (1910) guides are aligned, a guide element (1902) may be advanced through the lumen (1910) of first guide (1908) such that it exits the distal end of first guide (1908) and enters the lumen of the second guide (1910) (or vice versa). The guide element (1902) may then be advanced through the second guide (1910) (or the first guide (1908)) and the first (1908) and second (1910) guides may be withdrawn through the cannula, as shown in FIG. 19D. In some instances, both ends (not shown) of the guide element (1902) may extend out from a proximal end of the cannula and/or may extend outside of the body. In these variations, guide element (1902) may be a wire, a suture, yarn, strand, or the like. While FIGS. 19A-19D depict advancing a guide element (1902) through lumens (1912) of the first (1908) and second (1910) guides, it should be appreciated that in some variations, a tube or catheter may be advanced over the first (1908) and second (1910) guides to place the tube or catheter around the tissue structure (1904).

Figure 19E:
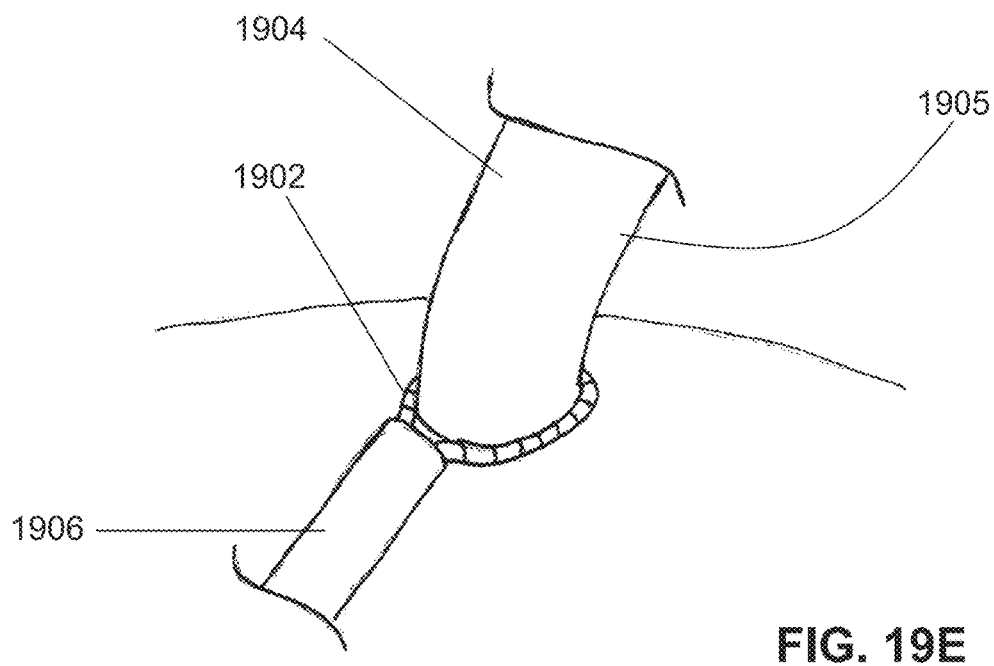
Figure 19F:
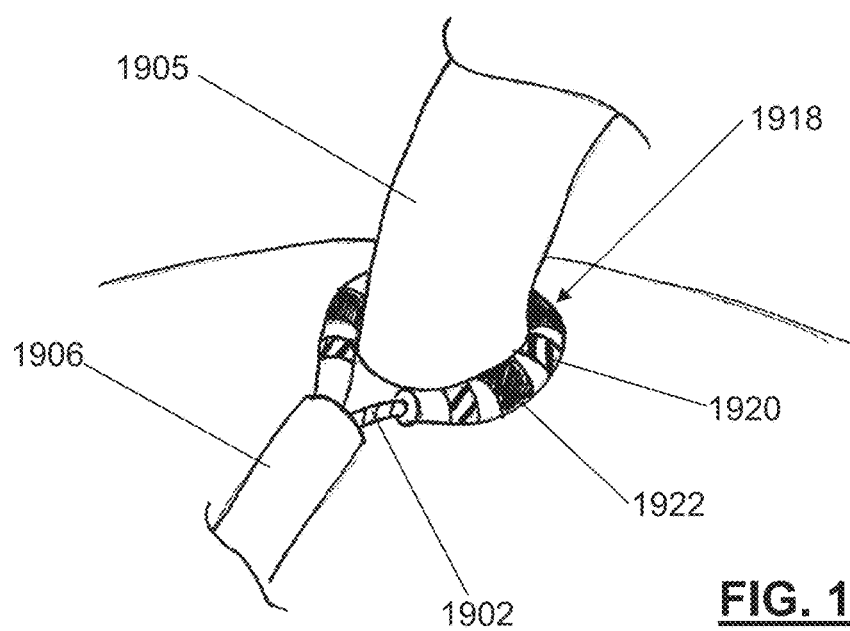

In some variations, the ends of the guide element (1902) may be pulled proximally to cinch the distal exposed portion of guide element (1902) (e.g., the portion of guide element extending from the distal end of cannula (1906)) around the tissue structure (1904), as shown in FIG. 19E. In variations where tissue structure (1904) is the left atrial appendage (not shown), cinching guide element (1902) around the left atrial appendage may act to close the left atrial appendage (temporarily or permanently). In variations where the left atrial appendage is used as an access port into the interior of the heart, as described hereinthroughout, guide element (1902) may be used to help provide hemostasis by temporarily closing the left atrial appendage around one or more devices placed through tissue of the left atrial appendage. Additionally or alternatively, in some variations, a knot, clip, or clamping structure (not shown) may be advanced over a portion of the guide element (1902) to hold the guide element in place around the tissue structure (1904). In variations where the guide element (1902) is placed around the left atrial appendage, the guide element (1902) may be used to close the left atrial appendage (as described immediately above). For example, a knot, clip, or clamping structure may be advanced over the guide element (1902) to hold it in place such that the left atrial appendage is held in a closed configuration. In some variations, the guide element may comprise a releasable suture loop, where cinching the guide element around the tissue structure (1904) likewise cinches the suture loop around the tissue structure (1905). Once the desired level of tightening is achieved, the suture loop may be released from the guide element, and the guide element may be retracted proximally. To secure the tension in the suture loop, a knot, clip or other clamping structure may be advanced through the cannula to lock the suture loop. In some variations, a suture-cutter or the like may be advanced over a portion the guide element (1902) or suture loop to sever at least a portion of the guide element (1902) or suture loop (e.g., the portions of guide element located proximal to the knot, clip, or clamping structure.)

Additionally or alternatively, one or more devices may be advanced over the guide element (1902) to place the device at or around the tissue structure (1904). In some variations, one or more ablation devices may be advanced over the guide element, such as ablation device (1918) shown in FIG. 19F. As shown there, ablation device (1918) may comprise one or more ablation elements (1920) and one or more magnetic elements (1922), and may be any of the ablation devices previously described. Additionally or alternatively, access device (1900) may also be used to place measurement electrodes, temperature sensors, and the like at or around the pulmonary veins, the LAA, and/or any tissue structure on the epicardial surface of the heart. The devices and methods depicted in FIGS. 19A-19F may be used in combination with any of the devices and methods previously described (e.g., in combination with the methods depicted in FIGS. 8A and 8B, FIG. 15, etc.).

Figure 16A:
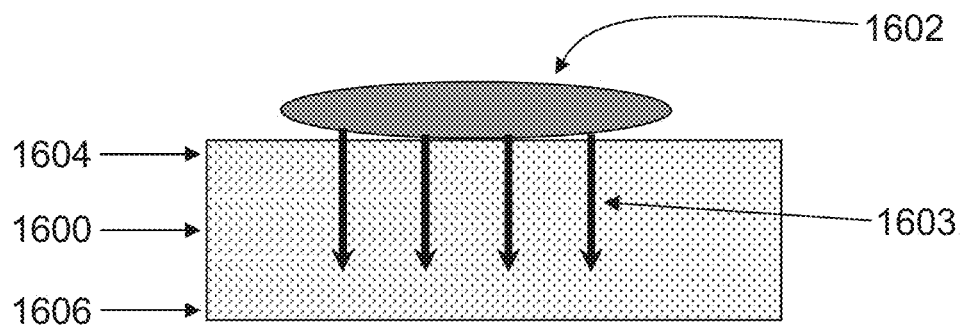
FIGS. 16A and 16B depict ablation patterns that may be formed by epicardial ablation of atrial wall tissue.
Figure 16B:
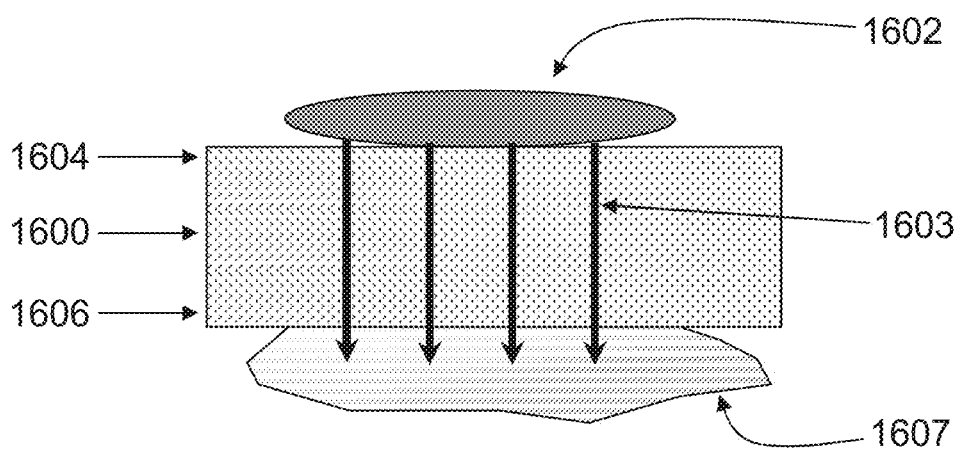

Examples of ablation patterns that may be formed by epicardial ablation method (1500) are shown in FIGS. 16A and 16B. Ablation array (1602) is positioned against an atrial wall (1600) on the epicardial side (1604). The ablation energy (1603) may be any mechanism of tissue ablation, as described above. The portion of atrial wall tissue (1600) that is closest to ablation array (1602) may be ablated relatively quickly, while tissue further from the ablation array, e.g. tissue near the endocardial side (1606), may not be ablated. To ablate a targeted tissue furthest from ablation array (1602), such as targeted tissue (1607) depicted in FIG. 16B, a longer exposure to a greater quantity of ablation energy (1603) may be needed. For example, to ablate tissue closest to the endocardial side (1606), ultrasound and radio frequencies may need to be increased, and laser energy and heat may need to be more intense. Additionally or alternatively, the ablation of tissue further from ablation array (1602) may involve increasing the exposure time of atrial wall (1600) to the ablation energy (1603). Depending on the type of ablation energy (1603) and/or the quality of the tissue (e.g., thermal energy conductivity, etc.), greater quantities of ablation energy may successfully ablate the targeted tissue (1607) without burning, charring, and/or coagulation of the tissue closest to the ablation array. For example, ultrasound ablation may be shaped and focused such that more energy is delivered to the targeted tissue (1607) than to the tissue on the epicardial side (1604). In some variations, closed system or open system irrigation may be included during the delivery of the energy source to limit the heating of tissue adjacent to the ablation array, while delivering larger quantities of energy to tissue further away from the ablation array. As described previously a temperature probe may be used to measure temperature changes that may arise from tissue ablation, which may help to regulate the amount of ablation applied to a tissue region.

IV. Systems

Also described herein are systems for affecting tissue within a body to form a lesion. In general, the systems may comprise devices that have one or more tissue-affecting elements, together with additional components that help to locate and secure the target tissue. For example, the system may comprise a first and second device, where each of the devices comprises an elongate member and one or more tissue-affecting elements. The first and second devices may be separate from each other, but have corresponding geometries and sizes so that operating the tissue-affecting elements may form a lesion in the tissue between them. These devices may have any geometry (e.g., size, number of curves, radii of curvature, etc.), one or more configurations (e.g., a delivery configuration and a deployed configuration) and may apply a variety of tissue-affecting mechanisms (e.g., cryogenic substances, lasers, high intensity focused ultrasound, radiofrequency energy, heat, microwave, etc.). The tissue-affecting elements for a given device may deliver a combination of one or more types of tissue-affecting mechanisms. The tissue-affecting elements may be any of the ablation elements previously described. Some devices may also comprise magnetic components so that the attractive force between the magnets may cause the first and second devices to be positioned in a certain orientation with respect to each other, e.g. opposite one another. Systems may also include actuators and controllers that regulate the application of the tissue-affecting mechanisms. For example, tissue-affecting elements may be configured to be operated simultaneously, and/or apply energy to the tissue in a pre-programmed manner. A controller may be coupled to the tissue-affecting elements to synchronize their operation temporally (e.g., to affect tissue in-phase or out-of-phase, synchronously or asynchronously) and spatially (e.g., to affect one region of tissue without affecting another, to affect one region of tissue from more than one surface, etc.). In some variations, a controller may be configured to receive temperature data measured at the target tissue site to regulate the operation of the tissue-affecting elements.

Some systems for affecting tissue within a body may include devices that aid in accessing and securing the tissue, as well as positioning the tissue-affecting elements with respect to the tissue. For example, some systems may comprise a closure device (such as described above) may be included to locate and secure target tissue, a piercing member, one or more guide cannulas, and one or more guide wires. These devices may be configured to be inserted through, or advanced over, each other, which may be desirable for minimally invasive procedures.

Although the foregoing invention has, for the purposes of clarity and understanding been described in some detail by way of illustration and example, it will be apparent that certain changes and modifications may be practiced, and are intended to fall within the scope of the appended claims.

What is claimed as new and desired to be protected by Letters Patent of the United States is:

1. A method of affecting tissue within a body comprising:
   advancing a first device comprising tissue-affecting elements to an endocardial surface of a left atrium, wherein the first device comprises a linear delivery configuration and a semi-circular deployed configuration;
   advancing a second device comprising tissue-affecting elements to an epicardial surface of the left atrium, wherein the second device comprises a linear delivery configuration and a semi-circular deployed configuration, and wherein the second device is configured to align with the first device;
   positioning the first device in the deployed configuration so that the tissue-affecting elements at least partially circumferentially surround a base of a pulmonary vein on the endocardial surface of the left atrium;
   positioning the second device in the deployed configuration so that the tissue-affecting elements at least partially circumferentially surround a trunk of the pulmonary vein on the epicardial surface of the left atrium;
   activating the first device such that the tissue-affecting elements form a lesion in the left atrium around the pulmonary vein from the endocardial surface; and
   activating the second device such that the tissue-affecting elements form a lesion in the left atrium around the pulmonary vein from the epicardial surface.

2. The method of claim 1, wherein the first and second devices are activated simultaneously.

3. The method of claim 1, wherein the first and second devices are activated sequentially and the method further comprises deactivating the first device before activating the second device.

4. The method of claim 3, further comprising deactivating the second device and re-activating the first device.

5. The method of claim 1, wherein advancing the first device comprises inserting a curved sheath at a location beneath a sternum and advancing the first device through the sheath.

6. The method of claim 1, wherein the second device is configured to align with the first device using one or more magnetic components.

7. The method of claim 1, further comprising verifying that the lesion is transmural.

8. The method of claim 7, wherein the verifying step comprises assessing the lesion using electrical impedance tomography.

9. The method of claim 7, wherein the verifying step comprises assessing the lesion using thermal imaging techniques.

10. The method of claim 1, wherein advancing the first device comprises advancing a first guide wire through a puncture in a left atrial appendage into the left atrium, and advancing the first device over the first guide wire.

11. The method of claim 10, wherein advancing the second device comprises advancing a second guide wire pericardially to the epicardial surface of the left atrium, and advancing the second device over the second guide wire.

12. The method of claim 11, wherein the second guide wire comprises a magnetic component at its distal tip configured to align the second guide wire and the first device.

13. The method of claim 10, further comprising stabilizing the left atrial appendage using a looped closure assembly.

14. The method of claim 13, wherein the looped closure assembly comprises a snare loop and a suture loop.

15. The method of claim 1, wherein the tissue-affecting elements of the first and second devices deliver at least one of the following: a cryogenic substance, high intensity focused ultrasound, heat energy, microwave energy, and radiofrequency energy.

16. The method of claim 1, wherein the first and second devices each further comprise a temperature sensor.

17. The method of claim 1, wherein the first and second devices are separate devices.

18. The method of claim 1, wherein the first device comprises a first ablation array and the second device comprises a second ablation array, wherein the first and second ablation arrays each comprise tissue-affecting elements and magnetic components.

19. The method of claim 18, wherein the first and second ablation arrays are configured to compress tissue against the ablation arrays to improve the efficacy of lesion formation.

20. The method of claim 18, wherein the first and second ablation arrays further comprise a shape-memory material.

21. The method of claim 18, wherein the ablation arrays are configured to position the tissue-affecting elements of the first device across from the tissue-affecting elements of the second device.

* * * * *